US011352389B2

(12) United States Patent
Griffioen et al.

(10) Patent No.: US 11,352,389 B2
(45) Date of Patent: Jun. 7, 2022

(54) TREATMENT OF HAEMATOLOGICAL MALIGNANCIES

(71) Applicant: ACADEMISCH ZIEKENHUIS LEIDEN (H.O.D.N. LEIDS UNIVERSITAIR MEDISCH CENTRUM), Leiden (NL)

(72) Inventors: Marieke Griffioen, Leiden (NL); J. H. Frederik Falkenburg, Leiden (NL)

(73) Assignee: Academisch Ziekenhuis Leiden (h.o.d.n. Leids Universitair Medisch Centrum), Leiden (NL)

( * ) Notice: Subject to any disclaimer, the term of this patent is extended or adjusted under 35 U.S.C. 154(b) by 0 days.

(21) Appl. No.: 16/627,230

(22) PCT Filed: Jun. 28, 2018

(86) PCT No.: PCT/NL2018/050421
§ 371 (c)(1),
(2) Date: Dec. 27, 2019

(87) PCT Pub. No.: WO2019/004831
PCT Pub. Date: Jan. 3, 2019

(65) Prior Publication Data
US 2020/0123200 A1    Apr. 23, 2020

(30) Foreign Application Priority Data

Jun. 30, 2017 (NL) ...................................... 2019156
Mar. 16, 2018 (NL) ...................................... 2020602

(51) Int. Cl.
| | |
|---|---|
| *C07K 7/06* | (2006.01) |
| *A61P 35/02* | (2006.01) |
| *A61K 35/17* | (2015.01) |
| *A61K 35/761* | (2015.01) |
| *C07K 14/47* | (2006.01) |
| *C07K 14/725* | (2006.01) |
| *C12N 15/86* | (2006.01) |
| *A61K 39/00* | (2006.01) |

(52) U.S. Cl.
CPC ............... *C07K 7/06* (2013.01); *A61K 35/17* (2013.01); *A61K 35/761* (2013.01); *A61P 35/02* (2018.01); *C07K 14/4748* (2013.01); *C07K 14/7051* (2013.01); *C12N 15/86* (2013.01); *A61K 2039/5154* (2013.01); *A61K 2039/525* (2013.01); *A61K 2039/53* (2013.01); *A61K 2039/572* (2013.01); *A61K 2039/585* (2013.01); *A61K 2039/6006* (2013.01)

(58) Field of Classification Search
CPC ............ C07K 7/06; A61P 35/02; A61K 35/17
See application file for complete search history.

(56) References Cited

U.S. PATENT DOCUMENTS

| | | | |
|---|---|---|---|
| 6,750,325 B1 | 6/2004 | Jolliffe et al. | |
| 2004/0202657 A1 | 10/2004 | Bolt et al. | |
| 2008/0292549 A1* | 11/2008 | Jakobsen | ................ A61P 31/00 424/1.69 |
| 2013/0273647 A1* | 10/2013 | Sahin | ............... C07K 14/70503 435/325 |

FOREIGN PATENT DOCUMENTS

| | | | | |
|---|---|---|---|---|
| CN | 102775495 | * | 11/2012 | ............. C07K 19/00 |
| WO | 2004106380 | | 12/2004 | |
| WO | 2006046270 | | 5/2006 | |
| WO | WO 2015/163778 | * | 10/2015 | ............... C12N 1/68 |
| WO | 2016022400 | | 2/2016 | |
| WO | 2016071758 | | 5/2016 | |
| WO | 2016187508 | | 1/2017 | |

OTHER PUBLICATIONS

Van der Lee et al., 2019, Mutated nucleophosmin 1 as immunotherapy target in acute myeloid leukemia, The Journal of Clinical Investigation, 129(2): 774-785.*
Greiner et al., Immune Response against the Mutated Region of Cytoplasmic NPM1 Might Contribute to the Favorable Clinical Outcome of AML Patients with NPM1 Mutations (NPM1 mut), Blood, XP002775981, vol. 122, No. 6, Aug. 8, 2013, 3 pages.
Greiner et al., Mutated Regions of Nucleophosmin 1 Elicit Both Cd4+ and Cd8+ T-cell Responses in Patients with Acute Myeloid Leukemia, Blood, vol. 120, No. 6, Aug. 9, 2012, 9 pages.
Gruszka et al., A Monoclonal Antibody against Mutated Nucleophosmin 1 for the Molecular Diagnosis of Acute Myeloid Leukemias, Blood, vol. 116, No. 12, Sep. 23, 2010, 8 pages.
Kuzelova et al., Altered HLA Class I Profile Associated with Type AID Nucleophosmin Mutation Points to Possible Anti-Nucleophosmin Immune Response in Acute Myeloid Leukemia, PLoS One, vol. 10, No. 5, May 20, 2015, 12 pages.
Liso et al., Nucleophosmin Leukaemic Mutants Contain C-Terminus Peptides that Bind HLA Class I Molecules, Leukemia, vol. 22, No. 2, Mar. 2008, pp. 424-426.
Sun et al., Mutated Regions of Nucleophosmin 1 Elicit CD8+ T-Cell Responses in Patients with Acute Myeloid Leukemia, vol. 100, No. 1, PB1627, May 31, 2015, 1 page.
International Application No. PCT/NL2018/050421, International Search Report and Written Opinion dated Oct. 16, 2018, 15 pages.
Netherland Application No. 2019156, Search Report and Written Opinion dated Nov. 24, 2017, 16 pages.
Altschul et al., Basic Local Alignment Search Tool, Journal of Molecular Biology, vol. 215, No. 3, Oct. 5, 1990, pp. 403-410.
Altschul et al., Gapped BLAST and PSI-BLAST: A New Generation of Protein Database Search Programs, Nucleic Acids Research, vol. 25, No. 17, Sep. 1, 1997, pp. 3389-3402.

(Continued)

*Primary Examiner* — Amber D Steele
(74) *Attorney, Agent, or Firm* — Kilpatrick Townsend & Stockton LLP

(57) ABSTRACT

Novel nucleic acid sequences, vectors, modified cells, peptides and pharmaceutical compositions are provided that are useful in the treatment of human subjects having a ΔNPM1 positive haematological malignancy. Corresponding methods and uses are also provided.

15 Claims, 17 Drawing Sheets

Specification includes a Sequence Listing.

(56) References Cited

OTHER PUBLICATIONS

Bassani-Sternberg & Coukos, Mass Spectrometry-Based Antigen Discovery for Cancer Immunotherapy, Curr. Opin. Immunol., vol. 41, Aug. 2016, pp. 9-17.
Blankenstein et al., Targeting Cancer-Specific Mutations by T Cell Receptor Gene Therapy, Curr. Opin. Immunol., vol. 33, Apr. 2015, pp. 112-119.
Burrows et al., Peptide-MHC Class I Tetrameric Complexes Display Exquisite Ligand Specificity, J. Immunol., vol. 165, No. 11, Dec. 1, 2000, pp. 6229-6234.
Cohen et al., Nonchromosomal Antibiotic Resistance in Bacteria: Genetic Transformation of *Escherichia coli* by R-Factor DNA, Proc. Nat. Acad. Sci., vol. 69, No. 8, Aug. 1972, pp. 2110-2114.
Coren et al., Production of Retroviral Constructs for Effective Transfer and Expression of T-Cell Receptor Genes Using Golden Gate Cloning, BioTechniques, vol. 58, No. 3, Mar. 2015, pp. 135-139.
Dohner et al., Acute Myeloid Leukemia, N. Engl. J. Med., vol. 373, No. 12, Sep. 17, 2015, pp. 1136-1152.
Dohner et al., Diagnosis and Management of Acute Myeloid Leukemia in Adults: Recommendations from an International Expert Panel, on Behalf of the European Leukemianet, Blood, vol. 115, No. 3, Jan. 21, 2010, pp. 453-474.
Falini et al., Cytoplasmic Nucleophosmin in Acute Myelogenous Leukemia with a Normal Karyotype, N. Engl. J. Med., vol. 352, No. 3, Jan. 20, 2005, pp. 254-266.
Heemskerk et al., Redirection of Antileukemic Reactivity of Peripheral T Lymphocytes Using Gene Transfer of Minor Histocompatibility Antigen HA-2-Specific T-Cell Receptor Complexes Expressing a Conserved Alpha Joining Region, Blood, vol. 102, No. 10, Nov. 15, 2003, 43 pages.
Ivey et al., Assessment of Minimal Residual Disease in Standard-Risk AML, N. Engl. J. Med., vol. 374, No. 5, Feb. 4, 2016, pp. 422-433.
Jahn et al., TCR-Based Therapy for Multiple Myeloma and Other B-Cell Malignancies Targeting Intracellular Transcription Factor BOB1, Blood, vol. 129, No. 10, Mar. 9, 2017, pp. 1284-1295.
Jones et al., Improving the Safety of Cell Therapy Products by Suicide Gene Transfer, Frontiers in Pharmacology, Mini Review Article, vol. 5, Article 254, Nov. 27, 2014, 8 pages.
Jones et al., Lentiviral Vector Design for Optimal T Cell Receptor Gene Expression in the Transduction of Peripheral Blood Lymphocytes and Tumor-Infiltrating Lymphocytes, Human Gene Therapy, vol. 20, Jun. 2009, pp. 630-640.
Lefranc et al., IMGT, The International Immunogenetics Database, Nucleic Acids Research, vol. 27, No. 1, Jan. 1, 1999, pp. 209-212.
Linnemann et al., High-Throughput Identification of Antigen-Specific TCRs by TCR Gene Capture, Nat. Med., vol. 19, No. 11, Nov. 2013, pp. 1534-1541.
Luchansky et al., Application of Electroporation for Transfer of Plasmid DNA to Lactobacillus, Lactococcus, Leuconostoc, Listeria, Pediococcus, Bacillus, Staphylococcus, Enterococcus and Propionibacterium, Molecular Microbiology, vol. 2, No. 5, Sep. 1988, pp. 637-646.
Meiring et al., Nanoscale LC MS$^{(n)}$: Technical Design and Applications to Peptide and Protein Analysis, J. Sep. Sci., vol. 25, 2002, pp. 557-568.
Monjezi et al., Enhanced Car T-Cell Engineering Using Non-Viral Sleeping Beauty Transposition from Minicircle Vectors, Leukemia, vol. 31, No. 1, Jan. 2017, pp. 186-194.
Myers et al., Optimal Alignments in Linear Space, Computer Applications in the Biosciences, vol. 4, No. 1, Mar. 1, 1988, pp. 11-17.
Needleman et al., A General Method Applicable to the Search for Similarities in the Amino Acid Sequence of Two Proteins, J. Mol. Biol., vol. 48, No. 3, Mar. 1970, pp. 443-453.
Papaemmanuil et al., Genomic Classification and Prognosis in Acute Myeloid Leukemia, N. Engl. J. Med., vol. 374, 23, Jun. 9, 2016, pp. 2209-2221.
Rodenko et al., Generation of Peptide-MHC Class I Complexes Through UV-Mediated Ligand Exchange, Nature Protocols, vol. 1, No. 3, 2006, pp. 1120-1132.
Schumacher et al., Neoantigens in Cancer Immunotherapy, Science, vol. 348, No. 6230, Apr. 3, 2015, pp. 69-74.
Szymczak et al., Correction of Multi-Gene Deficiency In vivo Using a Single 'Self-Cleaving' 2A Peptide-based Retroviral Vector, Nature Biotech., vol. 22, No. 5, May 2004, pp. 589-594.
Tran et al., Cancer Immunotherapy Based on Mutation-Specific CD4+ T Cells in a Patient with Epithelial Cancer, Science, vol. 344, No. 6184, May 9, 2014, pp. 641-645.
Tran et al., 'Final Common Pathway' of Human Cancer Immunotherapy: Targeting Random Somatic Mutations, Nat. Immunol., vol. 18, No. 3, Feb. 15, 2017, pp. 255-262.
Tran et al., T-Cell Transfer Therapy Targeting Mutant KRAS in Cancer, N. Engl. J. Med., vol. 375, No. 23, Dec. 8, 2016, pp. 2255-2262.
Turtle et al., CD19 CAR-T Cells of Defined CD4+:CD8+ Composition in Adult B Cell All Patients, J. Clin. Invest., vol. 126, No. 6, Jun. 1, 2016, pp. 2123-2138.
Turtle et al., Immunotherapy of Non-Hodgkin's Lymphoma with a Defined Ratio of CD8+ and CD4+ CD19-specific Chimeric Antigen Receptor-Modified T-Cells, Sci. Transl. Med., vol. 8, No. 355, 355ra116, Sep. 7, 2016, 13 pages.
Versluis et al., Comparative Value of Post-Remission Treatment in Cytogenetically Normal AML Subclassified by NPM1 and FLT3-ITD Allelic Ratio, Leukemia, vol. 31, No. 1, Jan. 2017, pp. 26-33.
Willemsen et al., Grafting Primary Human T Lymphocytes with Cancer-Specific Chimeric Single Chain and Two Chain TCR, Cell-Based Therapy, Gene Therapy, vol. 7, No. 16, Aug. 2000, pp. 1369-1377.

* cited by examiner

FIG. 8 - SEQ ID NO:1 – immunogenic peptide amino acid sequence

CLAVEEVSL

FIG. 9 - SEQ ID NO:2 – amino acid sequence of CDR3 (TCR α chain)

CAVTGARLMF

FIG. 10 - SEQ ID NO:3 – non-optimised nucleic acid sequence encoding CDR3 (TCR α chain)

TGTGCCGTTACGGGGGCCAGACTCATGTTT

FIG. 11 - SEQ ID NO:4 – optimised nucleic acid sequence encoding CDR3 (TCR α chain)

TGCGCAGTGACAGGAGCAAGGCTGATGTTC

FIG. 12 - SEQ ID NO:5 – amino acid sequence of CDR3 (TCR β chain)

CASSPGGLSNEQF

FIG. 13 - SEQ ID NO:6 – non-optimised nucleic acid sequence encoding CDR3 (TCR β chain)

TGCGCCAGCAGCCCTGGCGGCTTGTCCAATGAGCAGTTC

FIG. 14 - SEQ ID NO:7 – optimised nucleic acid sequence encoding CDR3 (TCR β chain)

TGCGCAAGCTCCCCAGGAGGCCTGTCCAACGAGCAGTTC

FIG. 15 - SEQ ID NO: 8 – amino acid sequence of α chain variable region

MKSLRVLLVILWLQLSWVWSQQKEVEQNSGPLSVPEGAIASLNCTYSDRGSQSFFWYR
QYSGKSPELIMFIYSNGDKEDGRFTAQLNKASQYVSLLIRDSQPSDSATYL**CAVTGARL
MF**GDGTQLVVKP

FIG. 16 - SEQ ID NO: 9 – non-optimised nucleic acid sequence encoding α chain variable region ATGAAATCCTTGAGAGTTTTACTAGTGATCCTGTGGCTTCAGTTGAGCTGGGTTTGG
AGCCAACAGAAGGAGGTGGAGCAGAATTCTGGACCCCTCAGTGTTCCAGAGGGAGC
CATTGCCTCTCTCAACTGCACTTACAGTGACCGAGGTTCCCAGTCCTTCTTCTGGTA
CAGACAATATTCTGGGAAAAGCCCTGAGTTGATAATGTTCATATACTCCAATGGTGAC
AAAGAAGATGGAAGGTTTACAGCACAGCTCAATAAAGCCAGCCAGTATGTTTCTCTG

FIG. 16 (cont.) -

CTCATCAGAGACTCCCAGCCCAGTGATTCAGCCACCTACCTCTGTGCCGTTACGGG GGCCAGACTCATGTTTGGAGATGGAACTCAGCTGGTGGTGAAGCCC

FIG. 17 - SEQ ID NO: 10 - optimised nucleic acid sequence encoding α chain variable region ATGAAATCCTTGAGAGTTTTACTAGTGATCCTGTGGCTTCAATTGAGCTGGGTGTGG TCCCAGCAGAAGGAGGTGGAGCAGAACTCTGGACCACTGAGCGTGCCAGAGGGAG CCATCGCCAGCCTGAATTGCACCTACTCCGACCGGGGCAGCCAGTCCTTCTTTTGG TACAGACAGTATTCCGGCAAGTCTCCCGAGCTGATCATGTTCATCTATTCTAACGGC GACAAGGAGGATGGCAGGTTTACAGCCCAGCTGAATAAGGCCTCCCAGTACGTGTC TCTGCTGATCCGCGACTCCCAGCCTTCTGATAGCGCCACCTACCTGTGCGCAGTGA CAGGAGCAAGGCTGATGTTCGGCGACGGAACCCAGCTGGTGGTGAAGCCA

FIG. 18 - SEQ ID NO: 11 – amino acid sequence of β chain variable region

MGSRLLCWVLLCLLGAGPVKAGVTQTPRYLIKTRGQQVTLSCSPISGHRSVSWYQQTP GQGLQFLFEYFSETQRNKGNFPGRFSGRQFSNSRSEMNVSTLELGDSALYLCASSPGG LSNEQFFGPGTRLTVL

FIG. 19 - SEQ ID NO: 12 – non- optimised nucleic acid sequence encoding β chain variable region ATGGGCTCCAGGCTGCTCTGTTGGGTGCTGCTTTGTCTCCTGGGAGCAGGCCCAGT AAAGGCTGGAGTCACTCAAACTCCAAGATATCTGATCAAAACGAGAGGACAGCAAGT GACACTGAGCTGCTCCCCTATCTCTGGGCATAGGAGTGTATCCTGGTACCAACAGA CCCCAGGACAGGGCCTTCAGTTCCTCTTTGAATACTTCAGTGAGACACAGAGAAACA AAGGAAACTTCCCTGGTCGATTCTCAGGGCGCCAGTTCTCTAACTCTCGCTCTGAGA TGAATGTGAGCACCTTGGAGCTGGGGGACTCGGCCCTTTATCTTTGCGCCAGCAGC CCTGGCGGCTTGTCCAATGAGCAGTTCTTCGGGCCAGGGACACGGCTCACCGTGC TA

FIG. 20 - SEQ ID NO: 13 - optimised nucleic acid sequence encoding β chain variable region ATGGGCTCCAGGCTGCTGTGCTGGGTGCTGCTGTGCCTGCTGGGAGCAGGACCAG TGAAGGCAGGCGTGACCCAGACACCTAGGTACCTGATCAAGACCCGCGGCCAGCA GGTGACACTGTCTTGCAGCCCTATCTCTGGCCACCGCTCCGTGTCTTGGTACCAGC AGACCCCAGGACAGGGCCTGCAGTTCCTGTTTGAGTATTTCTCTGAGACACAGCGG AACAAGGGCAATTTCCCCGGCCGGTTTAGCGGCAGACAGTTTAGCAACTCCAGATC TGAGATGAATGTGAGCACCCTGGAGCTGGGCGACTCCGCCCTGTACCTGTGCGCAA GCTCCCCAGGAGGCCTGTCCAACGAGCAGTTCTTTGGACCAGGAACCAGGCTGAC AGTGCTG

FIG. 21 - SEQ ID NO: 14 – amino acid sequence of CDR1 (TCR α chain)

SDRGSQS

FIG. 22 - SEQ ID NO: 15 – amino acid sequence of CDR2 (TCR α chain)

FIYSNGD

FIG. 23 - SEQ ID NO: 16 – amino acid sequence of CDR1 (TCR β chain)

SGHRS

FIG. 24 - SEQ ID NO: 17 – amino acid sequence of CDR2 (TCR β chain)

EYFSETQRNKGNF

FIG. 25 – SEQ ID NO: 18 - non-optimised nucleic acid sequence encoding CDR1 (TCR α chain)

AGTGACCGAGGTTCCCAGTCC

FIG. 26 – SEQ ID NO: 19 - optimised nucleic acid sequence encoding CDR1 (TCR α chain)

TCCGACCGGGGCAGCCAGTCC

FIG. 27 – SEQ ID NO: 20 – non-optimised nucleic acid sequence encoding CDR2 (TCR α chain)

TTCATATACTCCAATGGTGAC

FIG. 28 – SEQ ID NO: 21 – optimised nucleic acid sequence encoding CDR2 (TCR α chain)

TTCATCTATTCTAACGGCGAC

FIG. 29 – SEQ ID NO: 22 – non-optimised nucleic acid sequence encoding CDR1 (TCR β chain)

TCTGGGCATAGGAGT

FIG. 30 – SEQ ID NO: 23 – optimised nucleic acid sequence encoding CDR1 (TCR β chain)

TCTGGCCACCGCTCC

FIG. 31 – SEQ ID NO: 24 – non-optimised nucleic acid sequence encoding CDR2 (TCR β chain) GAATACTTCAGTGAGACACAGAGAAACAAAGGAAACTTC FIG. 32 – SEQ ID NO: 25 – optimised nucleic acid sequence encoding CDR2 (TCR β chain)
GAGTATTTCTCTGAGACACAGCGGAACAAGGGCAATTTC FIG. 33 – SEQ ID NO: 26 - immunogenic peptide amino acid sequence
AVEEVSLRK FIG. 34 – SEQ ID NO: 27 – immunogenic peptide amino acid sequence
CLAVEEVSLRK FIG. 35 – SEQ ID NO:28 - immunogenic peptide amino acid sequence
VEEVSLRK FIG. 36 – SEQ ID NO:29 - immunogenic peptide amino acid sequence
AVEEVSLR

TREATMENT OF HAEMATOLOGICAL MALIGNANCIES

Novel nucleic acid sequences, vectors, modified cells, peptides and pharmaceutical compositions are provided that are useful in the treatment of human subjects having a ΔNPM1 positive haematological malignancy. Corresponding methods and uses are also provided.

BACKGROUND

Haematological malignancies are cancers that affect the blood and lymph system. The cancer may begin in blood-forming tissue (e.g. bone marrow), or in the cells of the immune system. Examples of haematological malignancies include myeloid malignancies such as acute myeloid leukemia (AML).

Acute myeloid leukemia is a malignant disease of the bone marrow characterized by accumulation of myeloid precursor cells that are arrested in differentiation. Currently, standard therapy consists of induction chemotherapy followed by intensive consolidation chemotherapy or high dose therapy in combination with autologous or allogeneic hematopoietic stem cell transplantation (alloSCT), resulting in 5-year survival rates of 40-45% in patients 65 years and only 10% in patients >65 years. [1-2] AlloSCT is associated with low relapse rates, but this benefit is limited by high toxicity. Therefore, treatment with alloSCT is restricted to patients with good performance status, but poor prognosis based on adverse cytogenetic or molecular abnormalities or detectable persistent or relapsed disease after chemotherapy. In the majority of patients, relapses occur within 3 years after start of chemotherapy, indicating the pressing need for new targeted therapies with high efficacy and no or limited toxicity to treat and improve survival of patients with AML.[2]

Molecular characterization of AML has accelerated over the last decades. Whole genome and exome sequencing demonstrated that AML has a low mutational load with an average of 13 coding mutations per patient. For cancer types with a high mutational load, such as melanoma and lung carcinoma, it has been shown that a small fraction of somatic mutations encode neoantigens.[3] Neoantigens are peptides arising from tumor-specific DNA mutations that can be recognized by specific T cells when presented in the context of HLA on the tumor cell. The formation of these antigens is a probabilistic process in which each additional mutation increases the chance that a neoantigen is created. Since mutational load in AML is low, the number of neoantigens is expected to be limited.[3]

Neoantigens can serve as cancer rejection antigens in vivo after therapy with checkpoint inhibitors or adoptive transfer of in vitro expanded tumor-infiltrating lymphocytes (TILs).[3-4] Checkpoint inhibitors are antibodies that block inhibitory signals on T cells mediated by CTLA-4 (ipilimumab) or PD-1 (pembrolizumab and nivolumab), thereby stimulating the immune system to target neoantigens. Checkpoint inhibitors and TIL therapy have proven successful for tumors with high mutational load, but are ineffective for tumors with low mutational load. However, although overall mutational load in AML is low, somatic abnormalities often occur in a limited number of driver genes that are recurrently mutated in multiple patients.[5] As a result, neoantigens arising from recurrent mutations in AML are relevant for development of targeted immunotherapy.

There is a need for novel immunotherapies for treating haematological malignancies, including myeloid malignancies such as AML.

BRIEF SUMMARY OF THE DISCLOSURE

The inventors have recognized that a mutated form of nucleophosmin (ΔNPM1 or NPM1$^{mut}$) is an ideal target for immunotherapy of haematological malignancies such as myeloid malignancies (particularly AML) as the formation of the mutated protein is restricted to malignant hematopoietic cells.

Nucleophosmin (NPM1) is a driver gene that is frequently mutated in approximately 30% of patients with AML.[5] Mutated NPM1 has also been observed in other types of haematological malignancies (e.g. other myeloid malignancies), although frequencies in tumours other than AML are much lower. Patients with mutated NPM1 (ΔNPM1, or NPM1$^{mut}$) carry a characteristic 4 base pair (4-bp) frameshift insertion in exon 12 of the gene. The resulting ΔNPM1 protein is 4 amino acids (AA) longer than the wild type counterpart and its C-terminal 11 AA are translated in an alternative reading frame (CLAVEEVSLRK (SEQ ID NO: 27)). As a result, the ΔNPM1 protein is dislocated from the nucleolus, where it functions as a nucleocytoplasmic shuttle protein, to the cytoplasm.[6] The ΔNPM1 protein is thus localized intracellularly. However, HLA-restricted ΔNPM1-derived peptides are accessible on the cell surface to T cell receptors, and thus can be recognized by T cells.

By studying the HLA class I ligandome of primary AML the inventors have identified five peptides encoded by the alternative reading frame of ΔNPM1 that are presented by HLA class I. The five identified peptides are CLAVEEVSL (SEQ ID NO:1), AVEEVSLRK (SEQ ID NO:26), CLAVEEVSLRK (SEQ ID NO: 27), VEEVSLRK (SEQ ID NO:28) and AVEEVSLR (SEQ ID NO:29). These peptides can be used as therapeutic agents (e.g. vaccines) to treat or prevent ΔNPM1 positive AML [23]. Alternatively, they can be used as a target antigen for treatment of such patients with modified cells described herein (e.g. peripheral blood lymphocytes or tumour-infiltrating lymphocytes (TILs)) having T cell receptors that specifically recognize one of the specified peptides).

Advantageously, T cells expressing TCRs specific for a peptide selected from CLAVEEVSL (SEQ ID NO:1), AVEEVSLRK (SEQ ID NO:26), CLAVEEVSLRK (SEQ ID NO: 27), VEEVSLRK (SEQ ID NO:28) and AVEEVSLR (SEQ ID NO:29) can be used as an effective immunotherapy in the treatment of ΔNPM1 positive AML. TCR gene transfer approaches using these peptide-specific TCRs can therefore bring novel treatment modalities for patients with ΔNPM1 positive AML.

The inventors have shown, for the first time, that CLAVEEVSL (SEQ ID NO:1) is presented on the surface of primary AML cells isolated from HLA-A*02:01 positive patients with AML. Advantageously, the peptide can therefore be used as a therapeutic agent (e.g. vaccine) to treat or prevent ΔNPM1 positive AML in a HLA-A*02:01 positive human patient. Alternatively, it can be used as a target antigen for treatment of such patients with modified cells described herein (e.g. peripheral blood lymphocytes or tumour-infiltrating lymphocytes (TILs)) having T cell receptors that specifically recognize CLAVEEVSL (SEQ ID NO:1)).

To investigate whether T cells with T cell receptors (TCRs) specific for CLAVEEVSL (SEQ ID NO:1) presented in the context of HLA-A*02:01 are present in the T cell repertoire from healthy individuals, HLA-A*02:01 tetramers were produced for CLAVEEVSL (SEQ ID NO:1) and its cysteinylated variant and tetramer positive CD8 T cells were isolated from peripheral blood mononuclear cells (PBMC) from healthy individuals. Several tetramer positive T cell clones were tested and only two showed specific binding to CLAVEEVSL (SEQ ID NO:1) and recognition of HLA-A*02:01 and ΔNPM1 positive AML. The T cell receptor of the most reactive clone (1A2) was sequenced and introduced into CD8⁺ and CD4⁺ T cells, which demonstrated specific recognition and lysis of HLA-A*02:01 positive primary AML with ΔNPM1 in a co-receptor independent fashion.

The inventors have therefore identified a TCR that specifically binds to the neoantigen CLAVEEVSL (SEQ ID NO:1).

Advantageously, T cells expressing TCRs specific to CLAVEEVSL (SEQ ID NO:1) can therefore be used as an effective immunotherapy in the treatment of HLA-A*02:01 positive patients having a ΔNPM1 positive AML. TCR gene transfer approaches using CLAVEEVSL (SEQ ID NO:1)-specific TCRs can therefore bring novel treatment modalities for HLA-A*02:01 positive patients with ΔNPM1 positive AML.

Furthermore, the peptide CLAVEEVSL (SEQ ID NO:1) (and specifically its cysteinylated form i.e. C*LAVEEVSL (SEQ ID NO:1 in cysteinylated form)) can be used as a therapeutic agent (e.g. a vaccine) to treat or prevent ΔNPM1 positive AML in HLA-A*02:01 positive patients. The peptide itself therefore also has utility e.g. in isolated form, or when formulated as a pharmaceutical composition.

By studying the HLA class I ligandome of primary AML the inventors have also identified a distinct 9-mer peptide and 11-mer peptide encoded by the alternative reading frame of ΔNPM1 (AVEEVSLRK (SEQ ID NO:26) and CLAVEEVSLRK (SEQ ID NO: 27) respectively). Binding of each of AVEEVSLRK (SEQ ID NO:26) and CLAVEEVSLRK (SEQ ID NO: 27) to HLA-A*03:01 and HLA-A*11:01 was confirmed by monomer folding for tetramer production (as described herein in detail for the CLAVEEVSL (SEQ ID NO:1) peptide). Accordingly, each of the AVEEVSLRK (SEQ ID NO:26) and CLAVEEVSLRK (SEQ ID NO: 27) peptides can be used as a therapeutic agent (e.g. vaccine) to treat or prevent ΔNPM1 positive AML in a HLA-A*03:01 or HLA-A*11:01 positive human patient. Alternatively, each of these peptides can be used as a target antigen for treatment of such patients with modified cells described herein (e.g. peripheral blood lymphocytes or tumour-infiltrating lymphocytes (TILs)) having T cell receptors that specifically recognize AVEEVSLRK (SEQ ID NO:26) or CLAVEEVSLRK (SEQ ID NO: 27) respectively).

Monomer folding for tetramer production has also been successfully shown for AVEEVSLRK (SEQ ID NO:26) with HLA-A*01:01 (as described herein in detail for the CLAVEEVSL (SEQ ID NO:1) peptide). The capacity of AVEEVSLRK (SEQ ID NO:26) to bind HLA-A*01:01 has therefore been confirmed. AVEEVSLRK (SEQ ID NO:26) has also been identified in the HLA class I ligandome from a HLA-A*01:01 positive AML subject (AML4443) which lacks HLA-A*03:01 and HLA-A*11:01 (see FIG. 2). Accordingly, the AVEEVSLRK (SEQ ID NO:26) peptide can also be used as a therapeutic agent (e.g. vaccine) to treat or prevent ΔNPM1 positive AML in a HLA-A*01:01 positive human patient. Alternatively, this peptide can be used as a target antigen for treatment of such patients with modified cells described herein (e.g. peripheral blood lymphocytes or tumour-infiltrating lymphocytes (TILs)) having T cell receptors that specifically recognize AVEEVSLRK (SEQ ID NO:26)).

To investigate whether T cells with T cell receptors (TCRs) specific for AVEEVSLRK (SEQ ID NO:26) presented in the context of HLA-A*03:01 or HLA-A*11:01 are present in the T cell repertoire from healthy individuals, HLA-A*03:01 tetramers and HLA-A*11:01 tetramers were produced for AVEEVSLRK (SEQ ID NO:26) and tetramer positive CD8 T cells were isolated from peripheral blood mononuclear cells (PBMC) from healthy individuals. Several tetramer positive T cell clones were tested and one was identified as having specific binding to AVEEVSLRK (SEQ ID NO:26) in the context of HLA-A*03:01 (reactive clone (3B3); FIG. 37). Furthermore, one T cell clone was identified as having specific binding to AVEEVSLRK (SEQ ID NO:26) in the context of HLA-A*11:01 (reactive clone (6F11); FIG. 37). The reactivity of each of these clones (6F11 and 3B3) was also tested (FIGS. 38 and 39), wherein cytokine release was demonstrated by each clone when presented with ΔNPM1 peptide in the context of the appropriate HLA-A only.

The inventors have therefore identified two TCRs that specifically bind to the neoantigen AVEEVSLRK (SEQ ID NO:26) in the context of HLA-A*03:01 (the TCR from clone 3B3) or HLA-A*11:01 (the TCR from clone 6F11).

Advantageously, T cells expressing TCRs specific to AVEEVSLRK (SEQ ID NO:26) can therefore be used as an effective immunotherapy in the treatment of HLA-A*03:01, HLA-A*11:01 or HLA-A*01:01 positive patients having a ΔNPM1 positive AML. TCR gene transfer approaches using AVEEVSLRK (SEQ ID NO:26)-specific TCRs can therefore bring novel treatment modalities for HLA-A*03:01, HLA-A*11:01 or HLA-A*01:01 positive patients having a ΔNPM1 positive AML.

Furthermore, the peptide AVEEVSLRK (SEQ ID NO:26) can be used as a therapeutic agent (e.g. a vaccine) to treat or prevent ΔNPM1 positive AML in HLA-A*03:01, HLA-A*11:01 or HLA-A*01:01 positive patients. The peptide itself therefore also has utility e.g. in isolated form or when formulated as a pharmaceutical composition.

The inventors have shown that the peptide CLAVEEVSLRK (SEQ ID NO:27) is presented by HLA-A*03:01 or HLA-A*11:01. Therefore, specific binding to any one of the peptide may occur in the context of the appropriate HLA (i.e. specific binding to the peptide may occur only when it is presented by the appropriate HLA, as described above).

To investigate whether T cells with T cell receptors (TCRs) specific for CLAVEEVSLRK (SEQ ID NO: 27) presented in the context of HLA-A*03:01 are present in the T cell repertoire from healthy individuals, HLA-A*03:01 tetramers were produced for CLAVEEVSLRK (SEQ ID NO: 27) and its cysteinylated variant and tetramer positive CD8 T cells were isolated from peripheral blood mononuclear cells (PBMC) from healthy individuals. Several tetramer positive T cell clones were tested and one was identified as having specific binding to C*LAVEEVSLRK (SEQ ID NO:27 in cysteinylated form) in the context of HLA-A*03:01 (reactive clone (1F2); FIG. 37).

The inventors have therefore identified a TCR that specifically binds to the neoantigen C*LAVEEVSLRK (SEQ ID NO:27 in cysteinylated form) in the context of HLA-A*03:01 (the TCR from clone 1F2).

Advantageously, T cells expressing TCRs specific to CLAVEEVSLRK (SEQ ID NO: 27) (and specifically to the cysteinylated form of SEQ ID NO:27, i.e.

C*LAVEEVSLRK (SEQ ID NO:27 in cysteinylated form)) can therefore be used as an effective immunotherapy in the treatment of HLA-A*03:01 or HLA-A*11:01 positive patients having a ΔNPM1 positive AML. TCR gene transfer approaches using CLAVEEVSLRK (SEQ ID NO: 27)-specific TCRs (and specifically C*LAVEEVSLRK (SEQ ID NO:27 in cysteinylated form)) can therefore bring novel treatment modalities for HLA-A*03:01 and HLA-A*11:01 positive patients having a ΔNPM1 positive AML.

Furthermore, the peptide CLAVEEVSLRK (SEQ ID NO: 27) (and specifically its cysteinylated form i.e. C*LAVEEVSLRK (SEQ ID NO:27 in cysteinylated form)) can be used as a therapeutic agent (e.g. a vaccine) to treat or prevent ΔNPM1 positive AML in HLA-A*03:01 or HLA-A*11:01 positive patients. The peptide itself therefore also has utility e.g. in isolated form or when formulated as a pharmaceutical composition.

The invention has specific application in the treatment of patients having a ΔNPM1 positive AML. However, ΔNPM1 is also present in a subset of patients with other forms of haematological malignancy, particularly myeloid malignancies. The invention therefore applies equally to patients having ΔNPM1 positive haematological malignancies such as, but not limited to, myeloid malignancies (e.g. AML).

Accordingly, in one aspect the invention provides an isolated nucleic acid sequence encoding:
(a) a polypeptide comprising a CDR3 of a TCR α chain polypeptide that specifically binds to a peptide selected from CLAVEEVSL (SEQ ID NO:1), AVEEVSLRK (SEQ ID NO:26), CLAVEEVSLRK (SEQ ID NO:27), VEEVSLRK (SEQ ID NO:28) and AVEEVSLR (SEQ ID NO:29); and/or
(b) a polypeptide comprising a CDR3 of a TCR β chain polypeptide that specifically binds to a peptide selected from CLAVEEVSL (SEQ ID NO:1), AVEEVSLRK (SEQ ID NO:26), CLAVEEVSLRK (SEQ ID NO:27), VEEVSLRK (SEQ ID NO:28) and AVEEVSLR (SEQ ID NO:29).

The nucleic acid sequence may encode both (a) and (b), wherein (a) and (b) together specifically bind to the peptide selected from CLAVEEVSL (SEQ ID NO:1), AVEEVSLRK (SEQ ID NO:26), CLAVEEVSLRK (SEQ ID NO:27), VEEVSLRK (SEQ ID NO:28) and AVEEVSLR (SEQ ID NO:29).

The encoded polypeptide(s) may specifically bind to CLAVEEVSL (SEQ ID NO:1). The peptide may be in cysteinylated form. The encoded polypeptide(s) may therefore specifically bind C*LAVEEVSL (SEQ ID NO:1 in cysteinylated form) only.

Alternatively, the encoded polypeptide(s) may specifically bind to AVEEVSLRK (SEQ ID NO:26).

Alternatively, the encoded polypeptide(s) may specifically bind to CLAVEEVSLRK (SEQ ID NO:27). The peptide may be in cysteinylated form. The encoded polypeptide(s) may therefore specifically bind C*LAVEEVSLRK (SEQ ID NO:27 in cysteinylated form) only. The CDR3 of (a) may have an amino acid sequence having at least 90% sequence identity to CAVTGARLMF (SEQ ID NO:2). Optionally, the CDR3 of (a) is encoded by the nucleic acid sequence of SEQ ID NO: 3 or SEQ ID NO:4, or a genetically degenerate sequence thereof (i.e. other nucleic acid sequences that encode the same protein as a result of the degeneracy of the genetic code).

The CDR3 of (b) may have an amino acid sequence having at least 90% sequence identity to CASSPGGLSNEQF (SEQ ID NO:5). Optionally, the CDR3 of (b) is encoded by the nucleic acid sequence of SEQ ID NO: 6 or SEQ ID NO:7, or a genetically degenerate sequence thereof (i.e. other nucleic acid sequences that encode the same protein as a result of the degeneracy of the genetic code).

The CDR3 of (a) may be within a TCR α chain variable region that specifically binds to the selected peptide (i.e. SEQ ID NO:1, SEQ ID NO:26, SEQ ID NO:27, SEQ ID NO:28 or SEQ ID NO:29).

(a) may further comprise a TCR α chain constant region. In other words, polypeptide of (a) may comprise a full length TCR α chain variable region that specifically binds to the selected peptide and a full length TCR α chain constant region.

The TCR α chain variable region may have an amino acid sequence having at least 90% sequence identity to SEQ ID NO:8. Optionally, the TCR α chain variable region of (a) is encoded by the nucleic acid sequence of SEQ ID NO: 9 or SEQ ID NO:10, or a genetically degenerate sequence thereof (i.e. other nucleic acid sequences that encode the same protein as a result of the degeneracy of the genetic code).

The CDR3 of (b) may be within a TCR β chain variable region that specifically binds to the selected peptide (i.e. SEQ ID NO:1, SEQ ID NO:26, SEQ ID NO:27, SEQ ID NO:28 or SEQ ID NO:29).

(b) may further comprise a TCR β chain constant region. In other words, polypeptide of (b) may comprise a full length TCR α chain variable region that specifically binds to the selected peptide and a full length TCR α chain constant region.

The TCR β chain variable region of (b) may have an amino acid sequence having at least 90% sequence identity to SEQ ID NO:11. Optionally, the TCR β chain variable region of (b) is encoded by the nucleic acid sequence of SEQ ID NO: 12 or SEQ ID NO:13, or a genetically degenerate sequence thereof (i.e. other nucleic acid sequences that encode the same protein as a result of the degeneracy of the genetic code).

The CDR3 of (a) may be within a TCR α chain variable region having at least 90% sequence identity to SEQ ID NO:8, wherein the CDR3 has an amino acid sequence of SEQ ID NO: 2. Optionally (a) comprises a TCR α chain constant region.

In any of the embodiments described herein, the TCR α chain variable region CDR1 may have an amino acid sequence of SEQ ID NO:14 and the TCR α chain variable region CDR2 may have an amino acid sequence of SEQ ID NO:15.

The CDR3 of (b) may be within a TCR β chain variable region having at least 90% sequence identity to SEQ ID NO:11, wherein the CDR3 has an amino acid sequence of SEQ ID NO: 5. Optionally, (b) comprises a TCR β chain constant region.

In any of the embodiments described herein, the TCR β chain variable region CDR1 may have an amino acid sequence of SEQ ID NO:16 and the TCR β chain variable region CDR2 may have an amino acid sequence of SEQ ID NO:17.

The selected peptide CLAVEEVSL (SEQ ID NO:1) may be cysteinylated.

The selected peptide CLAVEEVSLRK (SEQ ID NO:27) may be cysteinylated.

The nucleic acid sequence may encode a T cell receptor.

For the avoidance of doubt, the inventors have identified that the peptide CLAVEEVSL (SEQ ID NO:1) is presented by HLA-A*02:01 (i.e. is HLA-A*02:01 restricted). Furthermore, the inventors have identified that the peptides AVEEVSLRK (SEQ ID NO:26) and CLAVEEVSLRK (SEQ ID NO: 27) are each presented by HLA-A*03:01 or HLA-A*11:01, and that AVEEVSLRK (SEQ ID NO:26) is also presented by HLA-A*01:01. Therefore, specific binding to any one of these peptides may occur in the context of the appropriate HLA (i.e. specific binding to the peptide may occur only when it is presented by the appropriate HLA, as described above).

The nucleic acid sequence of the invention may be a non-naturally occurring nucleic acid sequence (e.g. it may be that the entire sequence does not occur in its entirety in nature. For example, the nucleic acid sequence of the invention may be operably linked to a promoter, wherein the promoter is not naturally associated with equivalent human nucleic acid sequences in nature (e.g. human TCR sequences or fragments thereof); i.e. it is not the entire promoter that is naturally associated with the nucleic acid in its natural environment. In this context, such promoters may be considered exogenous promoters. Examples of appropriate promoters are described elsewhere.

In a further aspect, the invention provides a vector comprising a nucleic acid sequence of the invention.

The vector may be a plasmid or a viral vector. Optionally, the vector is selected from the group consisting of an adenovirus, adeno-associated virus, vaccinia virus, canary poxvirus, herpes virus, minicircle vector and synthetic DNA or RNA. Optionally the vector includes a promoter to which the nucleic acid sequence is operably linked, as described above.

In a further aspect, the invention provides a modified cell transfected or transduced with a nucleic acid sequence of the invention, or a vector of the invention.

The transfected or transduced nucleic acid sequence of the invention, or vector of the invention, may be operably linked to a promoter, as described above.

The modified cell may be selected from the group consisting of a CD8 T cell, a CD4 T cell, an NK cell, an NKT cell, a gamma-delta T cell, a hematopoietic stem cell, a progenitor cell, a T cell line or a NK-92 cell line.

The modified cell may be a human cell.

In a further aspect, the invention provides an isolated peptide comprising an amino acid sequence selected from:
(i) CLAVEEVSL (SEQ ID NO:1), wherein the cysteine amino acid may or may not be cysteinylated;
(ii) AVEEVSLRK (SEQ ID NO:26);
(iii) CLAVEEVSLRK (SEQ ID NO:27); wherein the cysteine amino acid may or may not be cysteinylated;
(iv) VEEVSLRK (SEQ ID NO:28); and
(v) AVEEVSLR (SEQ ID NO:29).

In a specific embodiment, the cysteine amino acid of SEQ ID NO:1 is cysteinylated.

In a specific embodiment, the cysteine amino acid of SEQ ID NO:27 is cysteinylated.

The peptide may have no more than 20 amino acids.

The peptide may consist of a sequence selected from:
(i) SEQ ID NO:1, wherein the cysteine amino acid may or may not be cysteinylated;
(ii) SEQ ID NO:26;
(iii) SEQ ID NO:27; wherein the cysteine amino acid may or may not be cysteinylated;
(iv) SEQ ID NO:28; and
(v) SEQ ID NO:29.

In a specific embodiment, the peptide may consist of the sequence of SEQ ID NO:1, wherein the cysteine amino acid of SEQ ID NO:1 is cysteinylated.

In a specific embodiment, the peptide may consist of the sequence of SEQ ID NO:27, wherein the cysteine amino acid of SEQ ID NO:27 is cysteinylated.

In a further aspect, the invention provides an isolated nucleic acid sequence encoding the peptide of the invention.

In a further aspect, the invention provides a vector comprising the nucleic acid sequence of the invention.

In a further aspect, the invention provides a pharmaceutical composition comprising a nucleic acid sequence of the invention, a vector of the invention, a modified cell of the invention, or an isolated peptide of the invention, and a pharmaceutically acceptable excipient, adjuvant, diluent and/or carrier.

The pharmaceutical composition may be formulated as a vaccine when the composition comprises an isolated peptide according to the invention (or a nucleic acid or vector encoding said isolated peptide). Suitable vaccine formulations for peptides and nucleic acids are well known in the art.

In a further aspect, the invention provides a method of treating or preventing a ΔNPM1 positive haematological malignancy in a human subject, the method comprising administering to the subject a therapeutically effective amount of a pharmaceutical composition of the invention.

The method of treating or preventing a ΔNPM1 positive haematological malignancy in a human subject may comprise administering to the subject a therapeutically effective amount of a peptide described herein (or a nucleic acid (e.g. RNA or DNA), or vector, encoding the peptide).

As an example, an isolated peptide comprising or consisting of an amino acid sequence selected from:
(i) CLAVEEVSL (SEQ ID NO:1), wherein the cysteine amino acid may or may not be cysteinylated;
(ii) AVEEVSLRK (SEQ ID NO:26);
(iii) CLAVEEVSLRK (SEQ ID NO:27); wherein the cysteine amino acid may or may not be cysteinylated;
(iv) VEEVSLRK (SEQ ID NO:28); and
(v) AVEEVSLR (SEQ ID NO:29)
may be administered as an immunotherapy (e.g. as a vaccine).

In a specific embodiment, the cysteine amino acid of SEQ ID NO:1 is cysteinylated.

In a specific embodiment, the cysteine amino acid of SEQ ID NO:27 is cysteinylated.

The haematological malignancy may be a myeloid malignancy.

The myeloid malignancy may be acute myeloid leukemia.

The method may induce or enhance a cell mediated immune response in the subject.

For the avoidance of doubt, the inventors have identified that the peptide CLAVEEVSL (SEQ ID NO:1) is HLA-A*02:01 restricted. Furthermore, the inventors have identified that the peptides AVEEVSLRK (SEQ ID NO:26) and CLAVEEVSLRK (SEQ ID NO: 27) are each presented by any one of HLA-A*03:01 and HLA-A*11:01, and that AVEEVSLRK (SEQ ID NO:26) is also presented by HLA-A*01:01. CLAVEEVSL (SEQ ID NO:1) and/or CLAVEEVSLRK (SEQ ID NO: 27) may specifically be in cysteinylated form.

Therefore, methods of treating or preventing a ΔNPM1 positive haematological malignancy in a HLA-A*02:01 positive human subject may preferentially use a pharmaceutical composition comprising a nucleic acid sequence encoding a polypeptide with specific binding to CLAVEEVSL (SEQ ID NO:1), a vector encoding such nucleic acid sequences, modified cells comprising such nucleic acid sequences or vectors, or a nucleic acid encoding CLAVEEVSL (SEQ ID NO:1), a vector encoding such nucleic acid sequences or a protein or peptide comprising the sequence CLAVEEVSL (SEQ ID NO:1) (all of which are described elsewhere herein in more detail). CLAVEEVSL (SEQ ID NO:1) may specifically be in cysteinylated form.

Similarly, methods of treating or preventing a ΔNPM1 positive haematological malignancy in a human subject that is positive for HLA-A*03:01 or HLA-A*11:01 may preferentially use a pharmaceutical composition comprising a nucleic acid sequence encoding a polypeptide with specific binding to AVEEVSLRK (SEQ ID NO:26) or CLAVEEVSLRK (SEQ ID NO: 27), a vector encoding such nucleic acid sequences, modified cells comprising such nucleic acid sequences or vectors, or a nucleic acid encoding AVEEVSLRK (SEQ ID NO:26) or CLAVEEVSLRK (SEQ ID NO: 27), a vector encoding such nucleic acid sequences or a protein or peptide comprising the sequence AVEEVSLRK (SEQ ID NO:26) or CLAVEEVSLRK (SEQ ID NO: 27) (all of which are described elsewhere herein in more detail).

Furthermore, methods of treating or preventing a ΔNPM1 positive haematological malignancy in a human subject that is positive for HLA-A*01:01 may preferentially use a pharmaceutical composition comprising a nucleic acid sequence encoding a polypeptide with specific binding to AVEEVSLRK (SEQ ID NO:26), a vector encoding such nucleic acid sequences, modified cells comprising such nucleic acid sequences or vectors, or a nucleic acid encoding AVEEVSLRK (SEQ ID NO:26), a vector encoding such nucleic acid sequences or a protein or peptide comprising the sequence AVEEVSLRK (SEQ ID NO:26) (all of which are described elsewhere herein in more detail).

CLAVEEVSLRK (SEQ ID NO: 27) may specifically be in cysteinylated form.

In a further aspect, the invention provides a pharmaceutical composition of the invention for use in treating or preventing a ΔNPM1 positive haematological malignancy in a human subject.

The pharmaceutical composition of the invention for use in treating or preventing a ΔNPM1 positive haematological malignancy in a human subject may comprise a therapeutically effective amount of a peptide described herein (or a nucleic acid (e.g. RNA or DNA), or vector, encoding the peptide).

As an example, the pharmaceutical composition may comprise an isolated peptide comprising or consisting of an amino acid sequence selected from:
(i) CLAVEEVSL (SEQ ID NO:1), wherein the cysteine amino acid may or may not be cysteinylated;
(ii) AVEEVSLRK (SEQ ID NO:26);
(iii) CLAVEEVSLRK (SEQ ID NO:27); wherein the cysteine amino acid may or may not be cysteinylated;
(iv) VEEVSLRK (SEQ ID NO:28); and
(v) AVEEVSLR (SEQ ID NO:29).

The pharmaceutical composition may be for use as an immunotherapy (e.g. as a vaccine).

In a specific embodiment, the cysteine amino acid of SEQ ID NO:1 is cysteinylated.

In a specific embodiment, the cysteine amino acid of SEQ ID NO:27 is cysteinylated.

The haematological malignancy may be a myeloid malignancy.

The myeloid malignancy may be acute myeloid leukemia.

The pharmaceutical composition may be for use in inducing or enhancing a cell mediated immune response in the subject.

As stated previously, the inventors have identified that the peptide CLAVEEVSL (SEQ ID NO:1) is HLA-A*02:01 restricted. Furthermore, the inventors have identified that the peptides AVEEVSLRK (SEQ ID NO:26) and CLAVEEVSLRK (SEQ ID NO: 27) are each presented by HLA-A*03:01 and HLA-A*11:01, and that AVEEVSLRK (SEQ ID NO:26) is also presented by HLA-A*01:01.

CLAVEEVSL (SEQ ID NO:1) and/or CLAVEEVSLRK (SEQ ID NO: 27) may specifically be in cysteinylated form.

Therefore, a pharmaceutical composition comprising a nucleic acid sequence encoding a polypeptide with specific binding to CLAVEEVSL (SEQ ID NO:1), a vector encoding such nucleic acid sequences, modified cells comprising such nucleic acid sequences or vectors, or a nucleic acid encoding CLAVEEVSL (SEQ ID NO:1), a vector encoding such nucleic acid sequences or a protein or peptide comprising the sequence CLAVEEVSL (SEQ ID NO:1) (all of which are described elsewhere herein in more detail) may be preferentially used when treating or preventing a ΔNPM1 positive haematological malignancy in a HLA-A*02:01 positive human subject. CLAVEEVSL (SEQ ID NO:1) may specifically be in cysteinylated form.

Similarly, a pharmaceutical composition comprising a nucleic acid sequence encoding a polypeptide with specific binding to AVEEVSLRK (SEQ ID NO:26) or CLAVEEVSLRK (SEQ ID NO: 27), a vector encoding such nucleic acid sequences, modified cells comprising such nucleic acid sequences or vectors, or a nucleic acid encoding AVEEVSLRK (SEQ ID NO:26) or CLAVEEVSLRK (SEQ ID NO: 27), a vector encoding such nucleic acid sequences or a protein or peptide comprising the sequence AVEEVSLRK (SEQ ID NO:26) or CLAVEEVSLRK (SEQ ID NO: 27) (all of which are described elsewhere herein in more detail) may be preferentially used when treating or preventing a ΔNPM1 positive haematological malignancy in a human subject that is positive for HLA-A*03:01 or HLA-A*11:01.

Furthermore, a pharmaceutical composition comprising a nucleic acid sequence encoding a polypeptide with specific binding to AVEEVSLRK (SEQ ID NO:26), a vector encoding such nucleic acid sequences, modified cells comprising such nucleic acid sequences or vectors, or a nucleic acid encoding AVEEVSLRK (SEQ ID NO:26), a vector encoding such nucleic acid sequences or a protein or peptide comprising the sequence AVEEVSLRK (SEQ ID NO:26) (all of which are described elsewhere herein in more detail) may be preferentially used when treating or preventing a ΔNPM1 positive haematological malignancy in a human subject that is positive for HLA-A*01:01.

CLAVEEVSLRK (SEQ ID NO: 27) may specifically be in cysteinylated form.

In a further aspect, the invention provides for the use of a pharmaceutical composition of the invention in the manufacture of a medicament for treating or preventing a ΔNPM1 positive haematological malignancy in a human subject.

The pharmaceutical composition may comprise a therapeutically effective amount of a peptide described herein (or a nucleic acid (e.g. RNA or DNA), or vector, encoding the peptide).

As an example, the pharmaceutical composition may comprise an isolated peptide comprising or consisting of an amino acid sequence selected from:
(i) CLAVEEVSL (SEQ ID NO:1), wherein the cysteine amino acid may or may not be cysteinylated;
(ii) AVEEVSLRK (SEQ ID NO:26);
(iii) CLAVEEVSLRK (SEQ ID NO:27); wherein the cysteine amino acid may or may not be cysteinylated;
(iv) VEEVSLRK (SEQ ID NO:28); and
(v) AVEEVSLR (SEQ ID NO:29).

The pharmaceutical composition may be for use as an immunotherapy (e.g. as a vaccine).

In a specific embodiment, the cysteine amino acid of SEQ ID NO:1 is cysteinylated.

In a specific embodiment, the cysteine amino acid of SEQ ID NO:27 is cysteinylated.

The haematological malignancy may be a myeloid malignancy.

The myeloid malignancy may be acute myeloid leukemia.

As mentioned elsewhere herein, the inventors have identified that the peptide CLAVEEVSL (SEQ ID NO:1) is HLA-A*02:01 restricted. Furthermore, the inventors have identified that the peptides AVEEVSLRK (SEQ ID NO:26) and CLAVEEVSLRK (SEQ ID NO: 27) are each presented by HLA-A*03:01 and HLA-A*11:01, and that AVEEVSLRK (SEQ ID NO:26) is also presented by HLA-A*01:01. CLAVEEVSL (SEQ ID NO:1) and/or CLAVEEVSLRK (SEQ ID NO: 27) may specifically be in cysteinylated form.

Therefore, a pharmaceutical composition comprising a nucleic acid sequence encoding a polypeptide with specific binding to CLAVEEVSL (SEQ ID NO:1), a vector encoding such nucleic acid sequences, modified cells comprising such nucleic acid sequences or vectors, or an isolated peptide comprising the sequence CLAVEEVSL (SEQ ID NO:1) (all of which are described elsewhere herein in more detail) may be preferentially used in the manufacture of a medicament for treating or preventing a ΔNPM1 positive haematological malignancy in a HLA-A*02:01 positive human subject. CLAVEEVSL (SEQ ID NO:1) may specifically be in cysteinylated form.

Similarly, a pharmaceutical composition comprising a nucleic acid sequence encoding a polypeptide with specific binding to AVEEVSLRK (SEQ ID NO:26) or CLAVEEVSLRK (SEQ ID NO: 27), a vector encoding such nucleic acid sequences, modified cells comprising such nucleic acid sequences or vectors, or an isolated peptide comprising the sequence AVEEVSLRK (SEQ ID NO:26) or CLAVEEVSLRK (SEQ ID NO: 27) (all of which are described elsewhere herein in more detail) may be preferentially used in the manufacture of a medicament for treating or preventing a ΔNPM1 positive haematological malignancy in a human subject that is positive for HLA-A*03:01 or HLA-A*11:01.

Furthermore, a pharmaceutical composition comprising a nucleic acid sequence encoding a polypeptide with specific binding to AVEEVSLRK (SEQ ID NO:26), a vector encoding such nucleic acid sequences, modified cells comprising such nucleic acid sequences or vectors, or an isolated peptide comprising the sequence AVEEVSLRK (SEQ ID NO:26) (all of which are described elsewhere herein in more detail) may be preferentially used in the manufacture of a medicament for treating or preventing a ΔNPM1 positive haematological malignancy in a human subject that is positive for HLA-A*01:01.

CLAVEEVSLRK (SEQ ID NO: 27) may specifically be in cysteinylated form.

In a further aspect, the invention provides a method of generating a T cell receptor, comprising contacting a nucleic acid sequence of the invention with a cell under conditions in which the nucleic acid sequence is incorporated and expressed by the cell to generate the T cell receptor that specifically binds to a peptide selected from SEQ ID NO:1, SEQ ID NO:26, SEQ ID NO:27, SEQ ID NO:28 and SEQ ID NO:29.

The method may be ex vivo.

As stated above, specific binding to any one of CLAVEEVSL (SEQ ID NO:1), AVEEVSLRK (SEQ ID NO:26) and CLAVEEVSLRK (SEQ ID NO: 27) may occur in the context of the appropriate HLA (e.g. specific binding to the peptide may only occur when it is presented by the appropriate HLA, as described above).

In a further aspect, the invention provides for the use of a peptide as a biomarker for a ΔNPM1 positive haematological malignancy in a human subject, wherein the peptide is selected from:
(i) CLAVEEVSL (SEQ ID NO:1), wherein the cysteine amino acid may or may not be cysteinylated;
(ii) AVEEVSLRK (SEQ ID NO:26);
(iii) CLAVEEVSLRK (SEQ ID NO:27); wherein the cysteine amino acid may or may not be cysteinylated;
(iv) VEEVSLRK (SEQ ID NO:28); and
(v) AVEEVSLR (SEQ ID NO:29).

In a specific embodiment, the cysteine amino acid of SEQ ID NO:1 is cysteinylated.

In a specific embodiment, the cysteine amino acid of SEQ ID NO:27 is cysteinylated.

In a further aspect, the invention provides a method of diagnosing a ΔNPM1 positive haematological malignancy in a human subject comprising:
determining the presence of a peptide in a sample isolated from the subject, wherein the peptide is selected from: (i) CLAVEEVSL (SEQ ID NO:1), wherein the cysteine amino acid may or may not be cysteinylated; (ii) AVEEVSLRK (SEQ ID NO:26); (iii) CLAVEEVSLRK (SEQ ID NO:27), wherein the cysteine amino acid may or may not be cysteinylated; (iv) VEEVSLRK (SEQ ID NO:28); and AVEEVSLR (SEQ ID NO:29),
wherein the presence of the peptide in the sample identifies the subject as having a ΔNPM1 positive haematological malignancy and wherein the absence of the peptide in the sample identifies the subject as not having a ΔNPM1 positive haematological malignancy.

In a specific embodiment, the cysteine amino acid of SEQ ID NO:1 is cysteinylated.

In a specific embodiment, the cysteine amino acid of SEQ ID NO:27 is cysteinylated.

In a further aspect, the invention provides a method of treating or preventing a ΔNPM1 positive haematological malignancy in a human subject, the method comprising: (i) determining the presence of a peptide in a sample isolated from the subject, wherein the peptide is selected from CLAVEEVSL (SEQ ID NO:1) wherein the cysteine amino acid may or may not be cysteinylated, AVEEVSLRK (SEQ ID NO:26), CLAVEEVSLRK (SEQ ID NO:27) wherein the cysteine amino acid may or may not be cysteinylated; VEEVSLRK (SEQ ID NO:28); and AVEEVSLR (SEQ ID NO:29); and (ii) administering to the subject a therapeutically effective amount of a pharmaceutical composition of the invention.

In a specific embodiment, the cysteine amino acid of SEQ ID NO:1 is cysteinylated.

In a specific embodiment, the cysteine amino acid of SEQ ID NO:27 is cysteinylated.

The statements provided previously in respect of each of the peptides and their HLA-restriction properties (and specifically in the context of the appropriate pharmaceutical compositions to use in methods of treating or preventing ΔNPM1 positive haematological malignancy in subjects with specific HLA status) apply equally here.

In a further aspect, the invention provides a pharmaceutical composition of the invention for use in treating or preventing a ΔNPM1 positive haematological malignancy in a human subject, wherein the subject has been identified as having a ΔNPM1 positive haematological malignancy by the presence of a peptide in a sample isolated from the subject, wherein the peptide is selected from:
(i) CLAVEEVSL (SEQ ID NO:1), wherein the cysteine residue may or may not be cysteinylated;
(ii) AVEEVSLRK (SEQ ID NO:26);
(iii) CLAVEEVSLRK (SEQ ID NO:27), wherein the cysteine residue may or may not be cysteinylated;
(iv) VEEVSLRK (SEQ ID NO:28); and
(v) AVEEVSLR (SEQ ID NO:29).

In this aspect, a subject that has been identified as having a ΔNPM1 positive haematological malignancy is a subject that has already been diagnosed as having a ΔNPM1 positive haematological malignancy prior to treatment due to the presence of a peptide in a sample isolated from the subject, wherein the peptide is selected from:
(i) CLAVEEVSL (SEQ ID NO:1), wherein the cysteine residue may or may not be cysteinylated;
(ii) AVEEVSLRK (SEQ ID NO:26);
(iii) CLAVEEVSLRK (SEQ ID NO:27), wherein the cysteine residue may or may not be cysteinylated;
(iv) VEEVSLRK (SEQ ID NO:28); and
(v) AVEEVSLR (SEQ ID NO:29).

In a specific embodiment, the cysteine amino acid of SEQ ID NO:1 is cysteinylated.

In a specific embodiment, the cysteine amino acid of SEQ ID NO:27 is cysteinylated.

The statements provided previously in respect of each of the peptides and their HLA-restriction properties (and specifically in the context of the appropriate pharmaceutical compositions to use when treating or preventing ΔNPM1 positive haematological malignancy in subjects with specific HLA status) apply equally here.

Throughout the description and claims of this specification, the words "comprise" and "contain" and variations of them mean "including but not limited to", and they are not intended to (and do not) exclude other moieties, additives, components, integers or steps.

Throughout the description and claims of this specification, the singular encompasses the plural unless the context otherwise requires. In particular, where the indefinite article is used, the specification is to be understood as contemplating plurality as well as singularity, unless the context requires otherwise.

Features, integers, characteristics, compounds, chemical moieties or groups described in conjunction with a particular aspect, embodiment or example of the invention are to be understood to be applicable to any other aspect, embodiment or example described herein unless incompatible therewith.

The patent, scientific and technical literature referred to herein establish knowledge that was available to those skilled in the art at the time of filing. The entire disclosures of the issued patents, published and pending patent applications, and other publications that are cited herein are hereby incorporated by reference to the same extent as if each was specifically and individually indicated to be incorporated by reference. In the case of any inconsistencies, the present disclosure will prevail.

Various aspects of the invention are described in further detail below.

BRIEF DESCRIPTION OF THE DRAWINGS

Embodiments of the invention are further described hereinafter with reference to the accompanying drawings, in which:

FIG. 8 shows the immunogenic peptide amino acid sequence of SEQ ID NO:1. It is noted that the cysteine amino acid of SEQ ID NO:1 may or may not be cysteinylated.

FIG. 9 shows an amino acid sequence of CDR3 (TCR α chain) (SEQ ID NO:2).

FIG. 10 shows a non-optimised nucleic acid sequence encoding CDR3 (TCR α chain) (SEQ ID NO:3).

FIG. 11 shows an optimised nucleic acid sequence encoding CDR3 (TCR α chain) (SEQ ID NO:4).

FIG. 12 shows an amino acid sequence of CDR3 (TCR β chain) (SEQ ID NO:5).

FIG. 13 shows a non-optimised nucleic acid sequence encoding CDR3 (TCR β chain) (SEQ ID NO:6).

FIG. 14 shows an optimised nucleic acid sequence encoding CDR3 (TCR β chain) (SEQ ID NO:7).

FIG. 15 shows an amino acid sequence of α chain variable region (SEQ ID NO: 8) (CDR3 underlined)

FIG. 16 shows a non-optimised nucleic acid sequence encoding α chain variable region (SEQ ID NO: 9) (CDR3 underlined).

FIG. 17 shows an optimised nucleic acid sequence encoding α chain variable region (SEQ ID NO: 10) (CDR3 underlined).

FIG. 18 shows an amino acid sequence of β chain variable region (SEQ ID NO: 11) (CDR3 underlined).

FIG. 19 shows a non-optimised nucleic acid sequence encoding β chain variable region (SEQ ID NO: 12) (CDR3 underlined).

FIG. 20 shows an optimised nucleic acid sequence encoding β chain variable region (SEQ ID NO: 13) (CDR3 underlined).

FIG. 21 shows an amino acid sequence of CDR1 (TCR α chain) (SEQ ID NO: 14).

FIG. 22 shows an amino acid sequence of CDR2 (TCR α chain) (SEQ ID NO: 15).

FIG. 23 shows an amino acid sequence of CDR1 (TCR β chain) (SEQ ID NO: 16).

FIG. 24 shows an amino acid sequence of CDR2 (TCR β chain) (SEQ ID NO: 17).

FIG. 25 shows a non-optimised nucleic acid sequence encoding CDR1 (TCR α chain) (SEQ ID NO:18).

FIG. 26 shows an optimised nucleic acid sequence encoding CDR1 (TCR α chain) (SEQ ID NO:19).

FIG. 27 shows a non-optimised nucleic acid sequence encoding CDR2 (TCR α chain) (SEQ ID NO:20).

FIG. 28 shows an optimised nucleic acid sequence encoding CDR2 (TCR α chain) (SEQ ID NO:21).

FIG. 29 shows a non-optimised nucleic acid sequence encoding CDR1 (TCR β chain) (SEQ ID NO:22).

FIG. 30 shows an optimised nucleic acid sequence encoding CDR1 (TCR β chain) (SEQ ID NO:23).

FIG. 31 shows a non-optimised nucleic acid sequence encoding CDR2 (TCR β chain) (SEQ ID NO:24).

FIG. 32 shows an optimised nucleic acid sequence encoding CDR2 (TCR β chain) (SEQ ID NO:25).

FIG. 33 shows the immunogenic peptide amino acid sequence of SEQ ID NO:26.

FIG. 34 shows the immunogenic peptide amino acid sequence of SEQ ID NO:27. It is noted that the cysteine amino acid of SEQ ID NO:27 may or may not be cysteinylated.

FIG. 35 shows the immunogenic peptide amino acid sequence of SEQ ID NO:28.

FIG. 36 shows the immunogenic peptide amino acid sequence of SEQ ID NO:29.

FIG. 37 shows T-cell clones binding to PE-conjugated HLA-A*03:01 UV-C*LA (clone 1F2; left), A*03:01 AVE (clone 3B3; middle) and A*11:01 AVE (clone 6F11; right) tetramers are shown.

FIG. 38 shows T-cell clone 3B3 (left) was tested for reactivity against T2 cells transduced with HLA-A*03:01 that were exogenously pulsed with titrated concentrations of ΔNPM1 peptides AVEEVSLRK (SEQ ID NO:26) (triangles), CLAVEEVSLRK (SEQ ID NO:27) (circles) or C*LAVEEVSLRK (SEQ ID NO:27 in cysteinylated form) (squares). Indicated is the release of GM-CSF (ng/ml) at different peptide concentrations (nM). T-cell clone 6F11 (right) was tested for reactivity against T2 cells transduced with HLA-A*11:01 that were exogenously pulsed with titrated concentrations of ΔNPM1 peptide AVEEVSLRK (SEQ ID NO:26) (triangles). Indicated is the release of IFN-γ (ng/ml) at different peptide concentrations (nM).

FIG. 39 shows T-cell clones 3B3 (left) and 6F11 (right) were tested for reactivity against K562 cells, K562 transduced with HLA-A*03:01 or A*11:01, K562 transduced with HLA-A*03:01 or A*11:01 as well as the genes encoding full-length wildtype or ΔNPM1, and the OCI-AML2 and OCI-AML3 cell lines endogenously expressing wildtype and ΔNPM1, respectively, transduced with A*03:01 or A*11:01. Indicated is the release of GM-CSF (clone 3B3) or IFN-γ (clone 6F11) in ng/ml.

DETAILED DESCRIPTION

Figure 1:
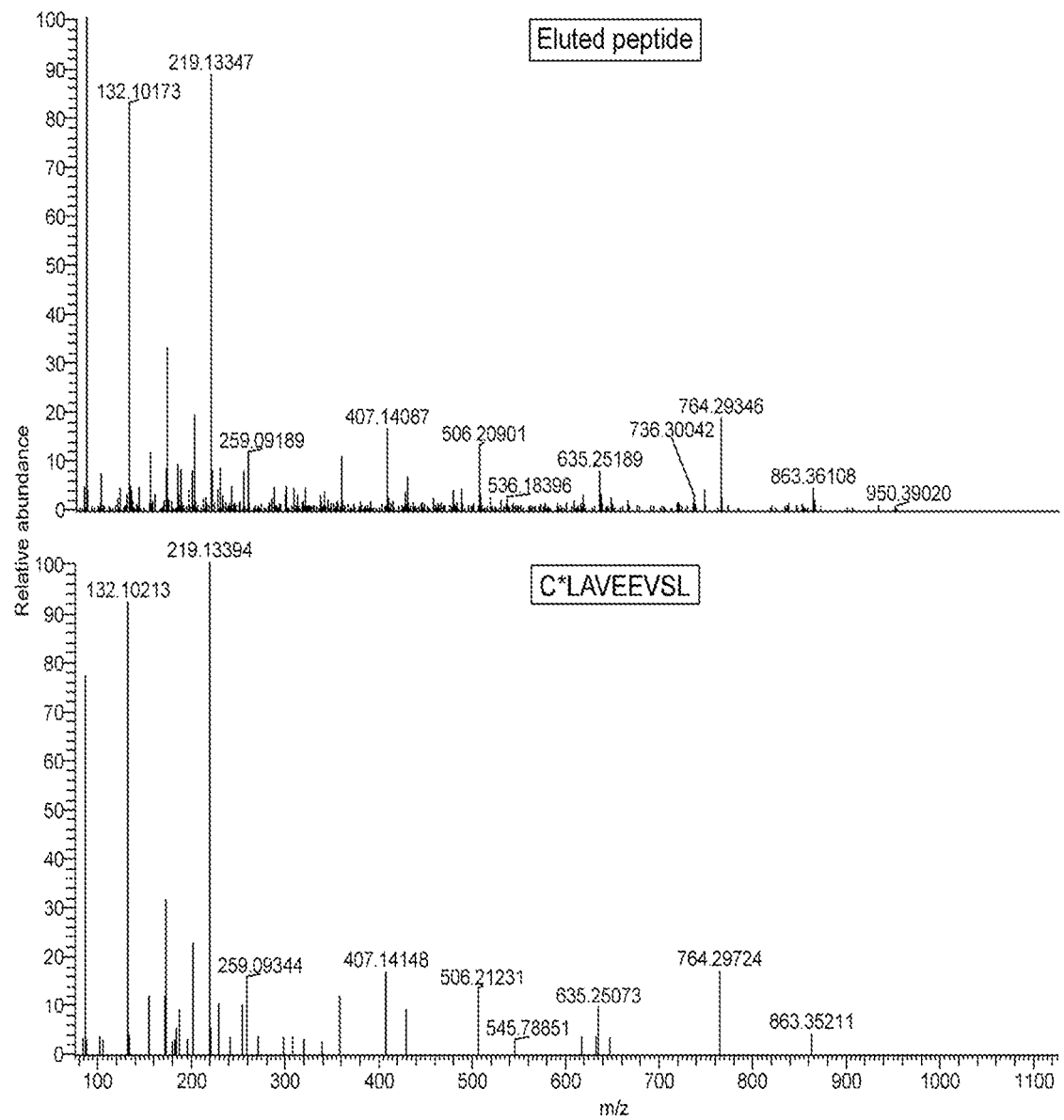
FIG. 1 provides validation of C*LAVEEVSL (SEQ ID NO:1 in cysteinylated form) as peptide eluted from HLA-A*02:01 positive AML with ΔNPM1. Mass spectra are shown for the eluted peptide from HLA-A*02:01 positive AML10197 with ΔNPM1 (top) and the synthetic peptide C*LAVEEVSL (SEQ ID NO:1 in cysteinylated form) after cysteinylation of the first residue (bottom). The data show a complete match between the mass spectra of both peptides.
Figure 2A:
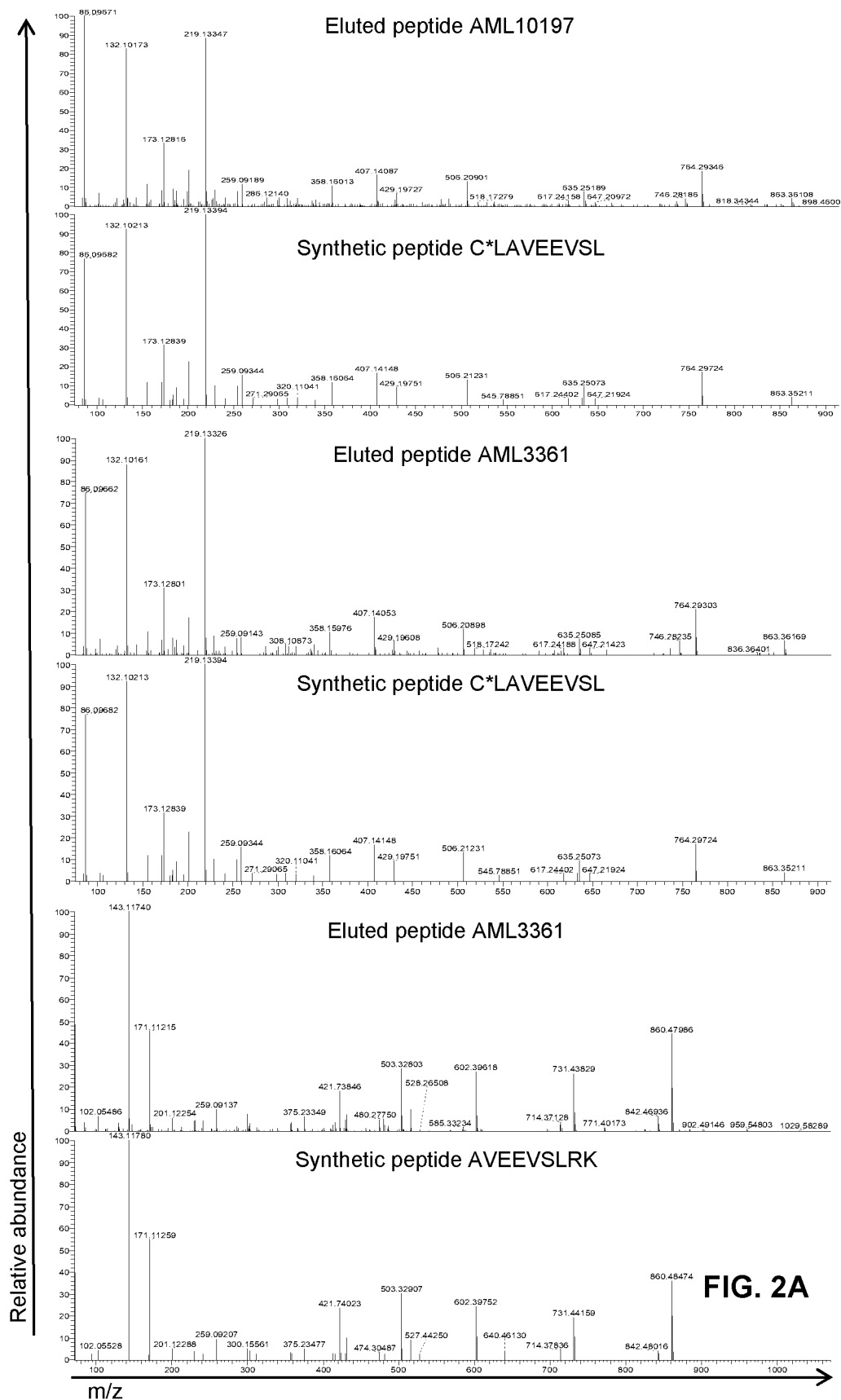
FIG. 2 provides validation of ΔNPM1 peptides eluted from primary AML. Tandem mass spectra are shown for eluted peptides from AML (upper) and synthetic peptides (lower). C*=cysteinylation of the Cys-residue. (A) Tandem mass spectra for eluted peptides from AML10197 (upper) and AML 3361 (middle) and synthetic peptide C*LAVEEVSL (SEQ ID NO:1 in cysteinylated form) and an eluted peptide from AML3361 and synthetic peptide AVEEVSLRK (SEQ ID NO:26) (lower). (B) Tandem mass spectra for eluted peptides from AML9448 (upper), AML5444 (middle) and AML5518 (lower) and synthetic peptide AVEEVSLRK (SEQ ID NO:26). (C) Tandem mass spectra for eluted peptides from AML6498 (upper) and AML4443 (middle) and synthetic peptide AVEEVSLRK (SEQ ID NO:26) and an eluted peptide from AML9448 and synthetic peptide C*LAVEEVSLRK (SEQ ID NO:27 in cysteinylated form) (lower). (D) Tandem mass spectra for an eluted peptide from AML6498 and synthetic peptide C*LAVEEVSLRK (SEQ ID NO:27 in cysteinylated form) (upper), an eluted peptide from AML3361 and synthetic peptide VEEVSLRK (SEQ ID NO:28) (middle) and an eluted peptide from AML5518 and synthetic peptide AVEEVSLR (SEQ ID NO:29) (lower).
Figure 2B:
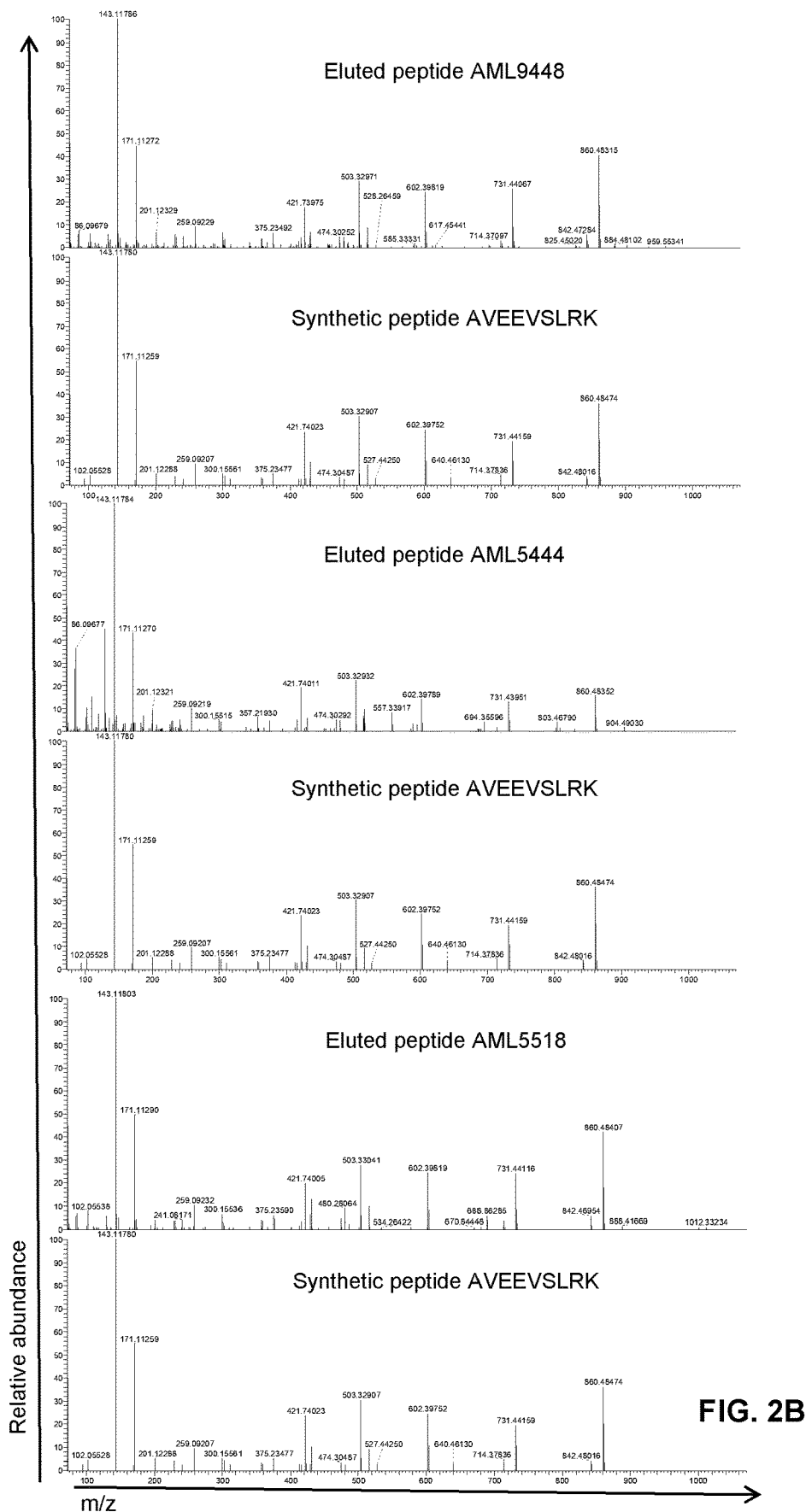
Figure 2C:
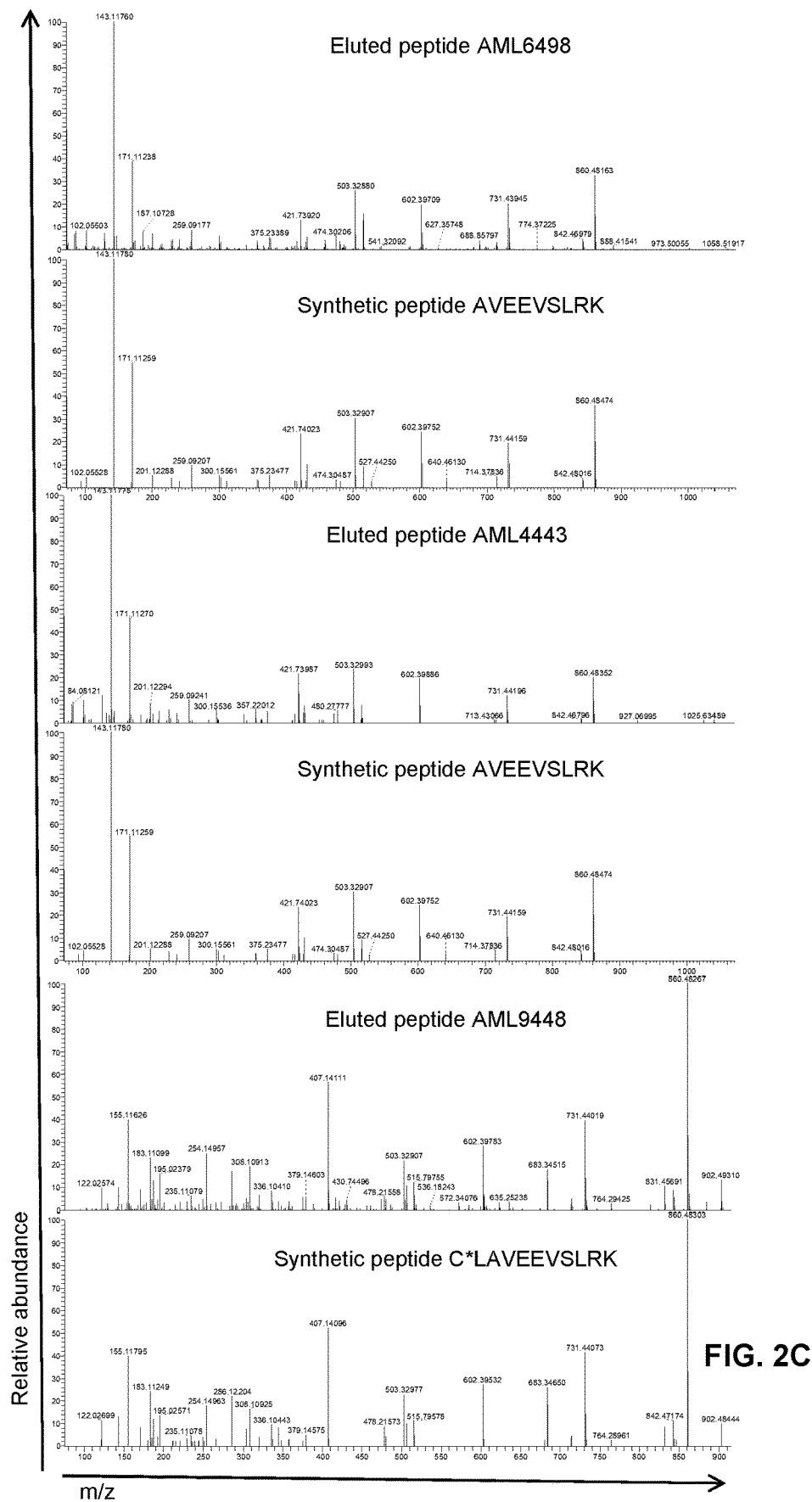
Figure 2D:
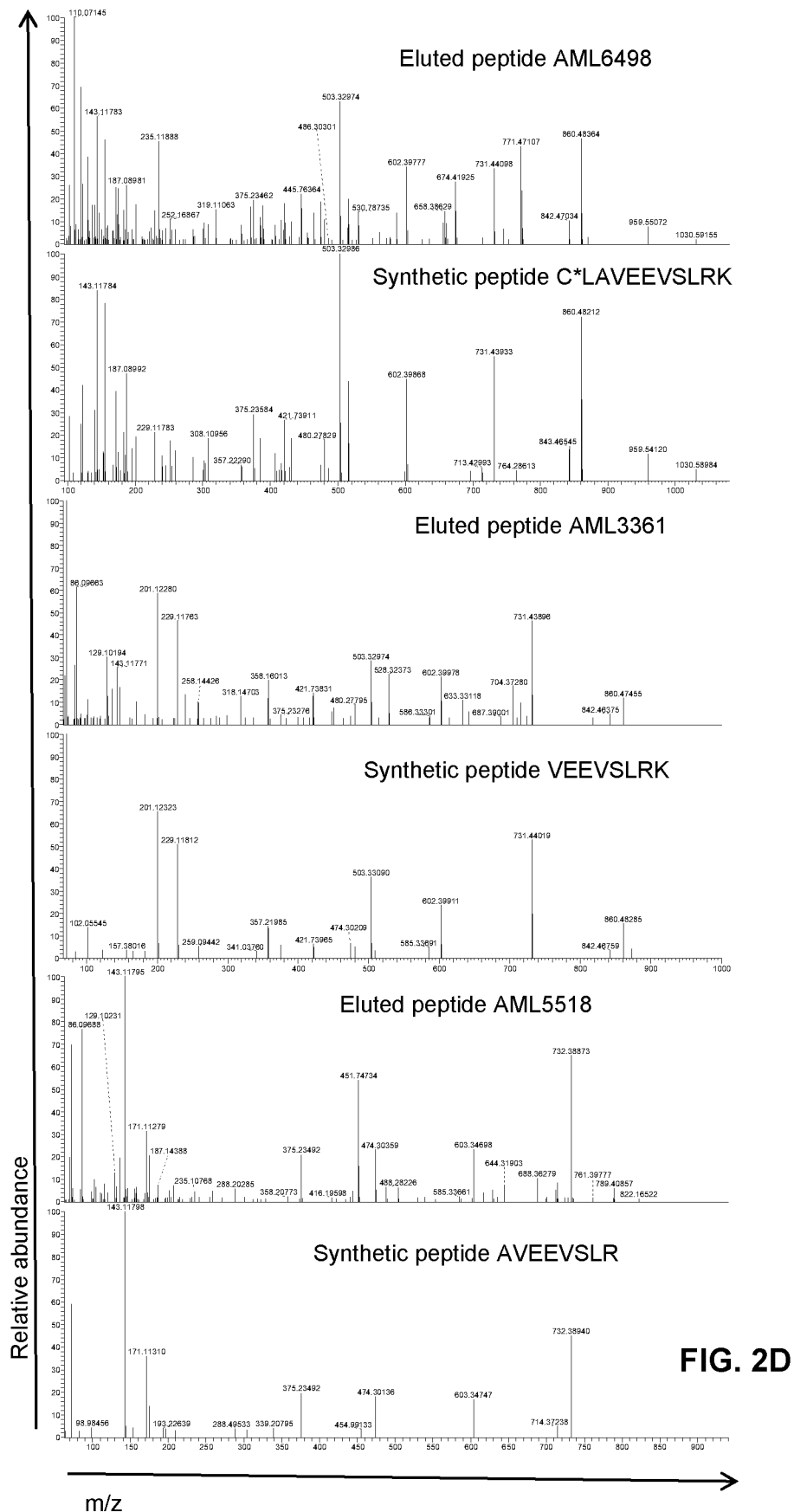

The immunogenicity of peptides derived from mutant NPM1 (ΔNPM1) has previously been studied [14] wherein an in silico screen of the entire amino acid sequence of ΔNPM1 was used to predict which peptides may be presented by HLA-A*02:01. Peptides with predicted HLA-A*02:01 binding were produced synthetically, including CLAVEEVSL (SEQ ID NO:1). CD8+ T cells isolated from healthy individuals and ΔNPM1 AML patients were stimulated with the peptides and T cell response was measured. Only two of the tested peptides (AIQDLCLAV (SEQ ID NO:32) and AIQDLCVAV (SEQ ID NO:33)) were found to elicit an immune response in vitro. These peptides were therefore considered to be most significant epitopes of ΔNPM1, and thus were used for further study.

The inventors have now identified five different peptides that are present in the HLA class I ligandome of ΔNPM1 positive primary AML (namely CLAVEEVSL (SEQ ID NO:1), AVEEVSLRK (SEQ ID NO:26), CLAVEEVSLRK (SEQ ID NO: 27), VEEVSLRK (SEQ ID NO:28) and AVEEVSLR (SEQ ID NO:29)).

The inventors have now also surprisingly shown that of all the possible peptides within ΔNPM1, it is the CLAVEEVSL (SEQ ID NO:1) peptide that is presented on the surface of primary ΔNPM1 AML cells isolated from HLA-A*02:01 cancer patients, and furthermore that the peptide is found in cysteinylated form on the surface of the isolated primary AML cells.

The inventors have now also surprisingly found that ΔNPM1-derived peptides AVEEVSLRK (SEQ ID NO:26) and CLAVEEVSLRK (SEQ ID NO: 27) are each presented by HLA-A*03:01 and HLA-A*11:01, and that AVEEVSLRK (SEQ ID NO:26) is also presented by HLA-A*01:01.

The inventors have isolated and cloned T cell receptors that are reactive with CLAVEEVSL (SEQ ID NO:1) from the T cell repertoire of healthy HLA-A*02:01 positive individuals. They have demonstrated that these T cell receptors can be used for genetic engineering of peripheral blood lymphocytes and that the genetically modified lymphocytes effectively kill HLA-A*02:01 positive AML having ΔNPM1. Advantageously, these TCRs can be used as an effective immunotherapy in the treatment of HLA-A*02:01 positive patients having a ΔNPM1 positive AML.

The inventors have also isolated a T cell clone that is reactive with CLAVEEVSLRK (SEQ ID NO: 27) (specifically, the cysteinylated variant of this peptide) from the T cell repertoire of healthy HLA-A*03:01 positive individuals. Advantageously, the TCR from this clone can be used as an effective immunotherapy in the treatment of HLA-A*03:01 positive patients having a ΔNPM1 positive AML.

The inventors have also isolated two T cell clones that are reactive with AVEEVSLRK (SEQ ID NO:26) from the T cell repertoire of healthy HLA-A*03:01 and HLA-A*11:01 positive individuals respectively. Advantageously, the TCRs from these clones can be used as an effective immunotherapy in the treatment of HLA-A*03:01 and HLA-A*11:01 positive patients having a ΔNPM1 positive AML.

Nucleic Acid Sequences that Encode TCR Polypeptide Components

The invention provides nucleic acid sequences that encode T cell receptor components that specifically bind to a peptide selected from CLAVEEVSL (SEQ ID NO:1), AVEEVSLRK (SEQ ID NO:26), CLAVEEVSLRK (SEQ ID NO:27), VEEVSLRK (SEQ ID NO:28) and AVEEVSLR (SEQ ID NO:29). The nucleic acid sequences may form part of a larger nucleic acid sequence that encodes a larger component part of a T cell receptor (e.g. TCR α chain variable region, a TCR β chain variable region, a TCR α chain, a TCR β chain etc). The nucleic acid sequences may also form part of a larger nucleic acid sequence that encodes a functioning T cell receptor (i.e. encodes a functional TCR α chain and a functional TCR β chain, optionally separated by a linker sequence that enables coordinate expression of two proteins or polypeptides by the same vector). More details on this are provided below.

The nucleic acid sequences may encode a small component of a T cell receptor e.g. a CDR3 domain of a TCR α chain polypeptide, or a CDR3 domain of a TCR β chain polypeptide only. The nucleic acid sequence may therefore be considered as a "building block" that provides an essential component for peptide specificity. The nucleic acid sequence of the invention may be incorporated into a distinct nucleic acid sequence (e.g. a vector) that encodes the other elements of a TCR variable chain, such that when the nucleic acid sequence of the invention is incorporated, a new nucleic acid sequence is generated that encodes a TCR α chain variable region and/or a TCR β chain variable region that specifically binds to a peptide selected from CLAVEEVSL (SEQ ID NO:1), AVEEVSLRK (SEQ ID NO:26), CLAVEEVSLRK (SEQ ID NO:27), VEEVSLRK (SEQ ID NO:28) and AVEEVSLR (SEQ ID NO:29). A nucleic acid sequence of the invention therefore has utility as an essential component of TCR specificity for the selected ΔNPM1 peptide, and thus can be used to generate a nucleic acid sequence encoding a TCR variable region with the required antigen binding activity and specificity to target ΔNPM1 positive AML.

A T cell receptor (TCR) is a molecule found on the surface of T cells (T lymphocytes) that is responsible for recognising a peptide that is bound to (presented by) a major histocompatibility complex (MHC) molecule on a target cell. The invention is directed to nucleic acid sequences that encode TCRs that interact with a particular peptide in the context of the appropriate serotype of MHC, e.g. CLAVEEVSL (SEQ ID NO:1) in the context of HLA-A*02:01; or one of AVEEVSLRK (SEQ ID NO:26) or CLAVEEVSLRK (SEQ ID NO: 27), each in the context of one of HLA-A*03:01 and HLA-A*11:01, or AVEEVSLRK (SEQ ID NO:26) in the context of HLA-A*01:01.

HLA-A*02:01 is a globally common human leukocyte antigen serotype within the HLA-A serotype group. Peptides that are presented by HLA-A*02:01 to TCRs are described as being "HLA-A*02:01 restricted".

HLA-A*03:01, HLA-A*11:01 and HLA-A*01:01 are also common human leukocyte antigen serotypes within the HLA-A serotype group. Peptides that are presented by HLA-A*03:01 to TCRs are described as being "HLA-A*03:01 restricted". Similarly, peptides that are presented by HLA-A*11:01 to TCRs are described as being "HLA-A*11:01 restricted". Similarly, peptides that are presented by HLA-A*01:01 to TCRs are described as being "HLA-A*01:01 restricted".

The TCR is composed of two different polypeptide chains. In humans, 95% of TCRs consist of an alpha (α) chain and a beta (β) chain (encoded by TRA and TRB respectively). When the TCR engages with peptide in the context of HLA (e.g. in the context of HLA-A*02:01, HLA-A*03:01 or HLA-A*11:01, as appropriate), the T cell is activated through signal transduction.

The alpha and beta chains of the TCR are highly variable in sequence. Each chain is composed of two extracellular domains, a variable region (V) and a constant region (C). The constant region is proximal to the T cell membrane followed by a transmembrane region and a short cytoplasmic tail while the variable region binds to the peptide/HLA-A complex.

The variable region of each chain has three hypervariable regions (also called complementarity determining regions (CDRs)). Accordingly, the TCR alpha chain comprises a CDR1, a CDR2 and a CDR3 and the TCR beta chain also comprises a (different) CDR1, CDR2, and a CDR3. In each of the alpha and beta chains, it is CDR3 that is mainly responsible for recognizing the peptide being presented by HLA-A.

In one aspect, the invention provides an isolated nucleic acid sequence encoding: (a) a polypeptide comprising a CDR3 of a TCR α chain polypeptide that specifically binds to a peptide selected from CLAVEEVSL (SEQ ID NO:1), AVEEVSLRK (SEQ ID NO:26), CLAVEEVSLRK (SEQ ID NO:27), VEEVSLRK (SEQ ID NO:28) and AVEEVSLR (SEQ ID NO:29); and/or (b) a polypeptide comprising a CDR3 of a TCR β chain polypeptide that specifically binds to a peptide selected from CLAVEEVSL (SEQ ID NO:1), AVEEVSLRK (SEQ ID NO:26), CLAVEEVSLRK (SEQ ID NO:27), VEEVSLRK (SEQ ID NO:28) and AVEEVSLR (SEQ ID NO:29).

In a specific embodiment, the encoded polypeptide(s) specifically bind to CLAVEEVSL (SEQ ID NO:1). CLAVEEVSL (SEQ ID NO:1) may be in cysteinylated form. The encoded polypeptide(s) may specifically bind the cysteinylated form only.

In a specific embodiment, the encoded polypeptide(s) specifically bind to AVEEVSLRK (SEQ ID NO:26).

In a specific embodiment, the encoded polypeptide(s) specifically bind to CLAVEEVSLRK (SEQ ID NO:27). CLAVEEVSLRK (SEQ ID NO: 27) may be in cysteinylated form. The encoded polypeptide(s) may specifically bind the cysteinylated form only.

The nucleic acid sequence may encode (a), (b), or (a) and (b). The nucleic acid sequence therefore encodes at least one polypeptide comprising a CDR3 of a T cell receptor polypeptide, wherein the CDR3 specifically binds to one of the following peptides: CLAVEEVSL (SEQ ID NO:1), AVEEVSLRK (SEQ ID NO:26), CLAVEEVSLRK (SEQ ID NO:27), VEEVSLRK (SEQ ID NO:28) or AVEEVSLR (SEQ ID NO:29).

The nucleic acid sequence may include an alpha chain CDR3 and a beta chain CDR3, wherein the alpha chain CDR3 and the beta chain CDR3 together specifically bind to the selected peptide.

The nucleic acid sequence therefore encodes a "CDR3 of a TCR α chain polypeptide" (also referred to herein as an alpha chain CDR3, or an α chain CDR3) and/or a "CDR3 of a TCR β chain polypeptide" (also referred to herein as a beta chain CDR3, or an β chain CDR3).

The alpha chain CDR3 may be that of SEQ ID NO:2 or one of the variants described below. Similarly, the beta chain CDR3 may be that of SEQ ID NO:5 or one of the variants described below. It is noted that these specific CDR3 have been found by the inventors to specifically bind to the peptide of SEQ ID NO:1.

Any of the permutations described below for (a) may be combined with the permutations described below for (b) (e.g. to form an appropriate nucleic acid sequence that encodes a functioning T cell receptor (i.e. encodes a functional TCR α chain and TCR β chain, optionally separated by a linker sequence that enables coordinate expression of two proteins or polypeptides by the same vector).

Polypeptide (a)—Components of the TCR Alpha Chain

In one embodiment, the CDR3 of (a) may have an amino acid sequence of SEQ ID NO:2, or be functional variant thereof (i.e. wherein the variant retains the ability to specifically bind to the peptide of SEQ ID NO:1). Such functional variants may be naturally occurring, synthetic, or synthetically improved functional variants of SEQ ID NO:2. The term "variant" also encompasses homologues. Functional variants will typically contain only conservative substitutions of one or more amino acids of SEQ ID NO:2, or substitution, deletion or insertion of non-critical amino acids in non-critical regions of the protein.

Non-functional variants are amino acid sequence variants of SEQ ID NO: 2 that do not specifically bind to SEQ ID NO:1. Non-functional variants will typically contain a non-conservative substitution, a deletion, or insertion or premature truncation of the amino acid sequence of SEQ ID NO:2 or a substitution, insertion or deletion in critical amino acids or critical regions. Methods for identifying functional and non-functional variants are well known to a person of ordinary skill in the art.

In one embodiment, the CDR3 of (a) may have an amino acid sequence having at least 90% sequence identity to the amino acid sequence of SEQ ID NO:2, whilst retaining the ability to specifically bind to the peptide of SEQ ID NO:1. In other words, a functional CDR3 with one amino acid substitution compared to the sequence of SEQ ID NO:2 is also encompassed. As stated previously, the amino acid substitution may be a conservative amino acid substitution. Suitably, percent identity can be calculated as the percentage of identity to the entire length of the reference sequence (e.g. SEQ ID NO:2).

In examples where the CDR3 of (a) has the amino acid sequence of SEQ ID NO:2, the CDR3 may be encoded by the nucleic acid sequence of SEQ ID NO:3 or SEQ ID NO:4, or a genetically degenerate sequence thereof (i.e. other nucleic acid sequences that encode the same protein as a result of the degeneracy of the genetic code). It is noted that SEQ ID NO:4 is the codon optimised version of the nucleic acid sequence for CDR3 of clone 1A2 (the non-optimised sequence being SEQ ID NO:3). Accordingly, the polypeptide of (a) may be encoded by the nucleic acid sequence of SEQ ID NO:3 or SEQ ID NO:4, or a genetically degenerate sequence thereof (i.e. other nucleic acid sequences that encode the same protein as a result of the degeneracy of the genetic code).

In one embodiment, the polypeptide of (a) comprises the CDR3 (e.g. the CDR3 of SEQ ID NO:2 or a variant thereof as defined above) within a TCR α chain variable region that specifically binds to the peptide of SEQ ID NO:1. In other words, the polypeptide of (a) may comprise a TCR α chain variable region which includes the specified CDR3, wherein the TCR α chain variable region (and the CDR3 within it) specifically binds to the peptide of SEQ ID NO:1. As will be clear to a person of skill in the art, the phrase "TCR α chain variable region" refers to the variable (V) region (extracellular domain) of a TCR alpha chain, and thus includes three hypervariable regions (CDR1, CDR2 and the specified CDR3), as well as the intervening sequences, but does not include the constant (C) region of the alpha chain, which does not form part of the variable chain.

The encoded TCR α chain variable region may comprise, in addition to the specified CDR3, a CDR1 having an amino acid sequence of SEQ ID NO:14, or functional variant thereof (i.e. wherein the variant retains the ability to specifically bind to the N-terminus of the peptide of SEQ ID NO:1). Such functional variants may be naturally occurring, synthetic, or synthetically improved functional variants of SEQ ID NO:14. The term "variant" also encompasses homologues. Functional variants will typically contain only conservative substitutions of one or more amino acids of SEQ ID NO:14, or substitution, deletion or insertion of non-critical amino acids in non-critical regions of the protein.

Non-functional variants are amino acid sequence variants of SEQ ID NO: 14 that do not specifically bind to the N-terminus of the peptide of SEQ ID NO:1. Non-functional variants will typically contain a non-conservative substitution, a deletion, or insertion or premature truncation of the amino acid sequence of SEQ ID NO:14 or a substitution, insertion or deletion in critical amino acids or critical regions. Methods for identifying functional and non-functional variants are well known to a person of ordinary skill in the art.

In one embodiment, the CDR1 of (a) (e.g. within the alpha chain variable region) may have an amino acid sequence having at least 85% sequence identity to the amino acid sequence of SEQ ID NO:14, whilst retaining the ability to specifically bind to the N terminus of the peptide of SEQ ID NO:1. In other words, a functional CDR1 with one amino acid substitution compared to the sequence of SEQ ID NO:14 is also encompassed. As stated previously, the amino acid substitution may be a conservative amino acid substitution. Suitably, percent identity can be calculated as the percentage of identity to the entire length of the reference sequence (e.g. SEQ ID NO:14).

In examples where the CDR1 of (a) (e.g. within the alpha chain variable region) has the amino acid sequence of SEQ ID NO:14, the CDR1 may be encoded by the nucleic acid sequence of SEQ ID NO:18 or SEQ ID NO:19, or a genetically degenerate sequence thereof (i.e. other nucleic acid sequences that encode the same protein as a result of the degeneracy of the genetic code). It is noted that SEQ ID NO:19 is the codon optimised version of the nucleic acid sequence for CDR1 of clone 1A2 (the non-optimised sequence being SEQ ID NO:18). Accordingly, the polypeptide of (a) may be encoded by the nucleic acid sequence of SEQ ID NO:18 or SEQ ID NO:19, or a genetically degenerate sequence thereof (i.e. other nucleic acid sequences that encode the same protein as a result of the degeneracy of the genetic code).

The encoded TCR α chain variable region may also comprise, in addition to the specified CDR3 (and optionally the specified CDR1 above), a CDR2 having an amino acid sequence of SEQ ID NO:15, or functional variant thereof (i.e. wherein the variant retains the ability to specifically bind to HLA-A*02:01). Such functional variants may be naturally occurring, synthetic, or synthetically improved functional variants of SEQ ID NO:15. The term "variant" also encompasses homologues. Functional variants will typically contain only conservative substitutions of one or more amino acids of SEQ ID NO:15, or substitution, deletion or insertion of non-critical amino acids in non-critical regions of the protein.

Non-functional variants are amino acid sequence variants of SEQ ID NO: 15 that do not specifically bind to HLA-A*02:01. Non-functional variants will typically contain a non-conservative substitution, a deletion, or insertion or premature truncation of the amino acid sequence of SEQ ID NO:15 or a substitution, insertion or deletion in critical amino acids or critical regions. Methods for identifying functional and non-functional variants are well known to a person of ordinary skill in the art.

In one embodiment, the CDR2 of (a) (e.g. within the alpha chain variable region) may have an amino acid sequence having at least 85% sequence identity to the amino acid sequence of SEQ ID NO:15, whilst retaining the ability to bind to HLA-A*02:01. In other words, a functional CDR2 with one amino acid substitution compared to the sequence of SEQ ID NO:15 is also encompassed. As stated previously, the amino acid substitution may be a conservative amino acid substitution. Suitably, percent identity can be calculated as the percentage of identity to the entire length of the reference sequence (e.g. SEQ ID NO:15).

In examples where the CDR2 of (a) (e.g. within the alpha chain variable region) has the amino acid sequence of SEQ ID NO:15, the CDR2 may be encoded by the nucleic acid sequence of SEQ ID NO:20 or SEQ ID NO:21, or a genetically degenerate sequence thereof (i.e. other nucleic acid sequences that encode the same protein as a result of the degeneracy of the genetic code). It is noted that SEQ ID NO:21 is the codon optimised version of the nucleic acid sequence for CDR2 of clone 1A2 (the non-optimised sequence being SEQ ID NO:20). Accordingly, the polypeptide of (a) may be encoded by the nucleic acid sequence of SEQ ID NO:20 or SEQ ID NO:21, or a genetically degenerate sequence thereof (i.e. other nucleic acid sequences that encode the same protein as a result of the degeneracy of the genetic code).

The polypeptide of (a) may therefore comprise a TCR alpha chain variable region that comprises the CDRs mentioned in detail above (by SEQ ID specifically, or variants thereof), with appropriate intervening sequences between the CDRs.

The TCR alpha chain variable region of (a) may have an amino acid sequence of SEQ ID NO:8, or a functional variant thereof (i.e. wherein the variant retains the ability to specifically bind to the peptide of SEQ ID NO:1). Such functional variants may be naturally occurring, synthetic, or synthetically improved functional variants of SEQ ID NO:8. The term "variant" also encompasses homologues. Functional variants will typically contain only conservative substitutions of one or more amino acids of SEQ ID NO:8, or substitution, deletion or insertion of non-critical amino acids in non-critical regions of the protein.

Non-functional variants are amino acid sequence variants of SEQ ID NO: 8 that do not specifically bind to SEQ ID NO:1. Non-functional variants will typically contain a non-conservative substitution, a deletion, or insertion or premature truncation of the amino acid sequence of SEQ ID NO:8 or a substitution, insertion or deletion in critical amino acids or critical regions. Methods for identifying functional and non-functional variants are well known to a person of ordinary skill in the art.

In one embodiment, the TCR alpha chain variable region of (a) may have an amino acid sequence having at least 75%, at least 80%, at least 85% or at least 90% (or at least 91%, at least 92%, at least 93%, at least 94%, at least 95%, at least 96%, at least 97%, at least 98%, at least 99%, or 100%) sequence identity to the amino acid sequence of SEQ ID NO:8, whilst retaining the ability to specifically bind to the peptide of SEQ ID NO:1. In other words, a functional TCR alpha chain variable region with one or more amino acid substitutions compared to the sequence of SEQ ID NO:8 is also encompassed. As stated previously, the amino acid substitution may be a conservative amino acid substitution. The variability in sequence compared to SEQ ID NO:8 may all be in regions of the TCR alpha chain variable region that do not form CDRs (i.e. the variant may have the CDRs of SEQ ID NO: 2, SEQ ID NO:14 and/or SEQ ID NO:15, and still have 25% (or less) sequence variability compared to SEQ ID NO:8). In other words, the sequence of the CDRs of SEQ ID NO:8 may be retained whilst the rest of the sequence is varied, as appropriate within the "at least 75% identity" parameters specified above. Suitably, percent identity can be calculated as the percentage of identity to the entire length of the reference sequence (e.g. SEQ ID NO:8).

As an example, the polypeptide of (a) may comprise the CDR3 within a TCR α chain variable region having at least 75% (e.g. at least 75%, at least 80%, at least 85%, at least 90%, at least 95% etc) sequence identity to the amino acid sequence of SEQ ID NO:8, wherein the CDR3 has an amino acid sequence of SEQ ID NO: 2. In this example, the TCR a chain variable region CDR1 may have an amino acid sequence of SEQ ID NO:14 and the TCR α chain variable region CDR2 may have an amino acid sequence of SEQ ID NO:15.

In examples where the TCR alpha chain variable region of (a) has the amino acid sequence of SEQ ID NO:8, the TCR alpha chain variable region may be encoded by the nucleic acid sequence of SEQ ID NO:9 or SEQ ID NO:10, or a genetically degenerate sequence thereof (i.e. other nucleic acid sequences that encode the same protein as a result of the degeneracy of the genetic code). It is noted that SEQ ID NO:10 is the codon optimised version of the nucleic acid sequence for TCR alpha chain variable region of clone 1A2 (the non-optimised sequence being SEQ ID NO:9). Accordingly, the polypeptide of (a) may be encoded by the nucleic acid sequence of SEQ ID NO:9 or SEQ ID NO:10, or a genetically degenerate sequence thereof (i.e. other nucleic acid sequences that encode the same protein as a result of the degeneracy of the genetic code).

For the avoidance of doubt, the polypeptide of (a) may comprise a TCR α chain variable region (as specified above) and a TCR α chain constant region. An example of a suitable constant region is encoded in the MP71-TCR-flex retroviral vector used herein by GenScript. However, the invention is not limited to this specific constant region, and encompasses any appropriate TCR α chain constant region. The constant region may be murine derived, human derived or humanised. Methods for identifying or generating appropriate constant regions are well known to a person of skill in the art and are well within their routine capabilities.

By way of example only, the constant region may be encoded by or derived from a vector, such as a lentiviral, retroviral or plasmid vector but also adenovirus, adeno-associated virus, vaccinia virus, canary poxvirus or herpes virus vectors in which murine or human constant regions are pre-cloned. Recently, minicircles have also been described for TCR gene transfer (non-viral Sleeping Beauty transposition from minicircle vectors as published by R Monjezi, C Miskey, T Gogishvili, M Schleef, M Schmeer, H Einsele, Z Ivics and M Hudecek in Leukemia 2016). Moreover, naked (synthetic) DNA/RNA can also be used to introduce the TCR. As an example, a pMSGV retroviral vector with pre-cloned TCR-Ca and Cb genes as described in LV Coren et al., BioTechniques 2015 may be used to provide an appropriate constant region.

Polypeptide (b)—Components of the TCR Beta Chain

In one embodiment, the CDR3 of (b) may have an amino acid sequence of SEQ ID NO:5, or be functional variant thereof (i.e. wherein the variant retains the ability to specifically bind to the peptide of SEQ ID NO:1). Such functional variants may be naturally occurring, synthetic, or synthetically improved functional variants of SEQ ID NO:5. The term "variant" also encompasses homologues. Functional variants will typically contain only conservative substitutions of one or more amino acids of SEQ ID NO:5, or substitution, deletion or insertion of non-critical amino acids in non-critical regions of the protein.

Non-functional variants are amino acid sequence variants of SEQ ID NO: 5 that do not specifically bind to SEQ ID NO:1. Non-functional variants will typically contain a non-conservative substitution, a deletion, or insertion or premature truncation of the amino acid sequence of SEQ ID NO:5 or a substitution, insertion or deletion in critical amino acids or critical regions. Methods for identifying functional and non-functional variants are well known to a person of ordinary skill in the art.

In one embodiment, the CDR3 of (b) may have an amino acid sequence having at least 90% sequence identity to the amino acid sequence of SEQ ID NO:5, whilst retaining the ability to specifically bind to the peptide of SEQ ID NO:1. In other words, a functional CDR3 with one amino acid substitution compared to the sequence of SEQ ID NO:5 is also encompassed. As stated previously, the amino acid substitution may be a conservative amino acid substitution. Suitably, percent identity can be calculated as the percentage of identity to the entire length of the reference sequence (e.g. SEQ ID NO:5).

In examples where the CDR3 of (b) has the amino acid sequence of SEQ ID NO:5, the CDR3 may be encoded by the nucleic acid sequence of SEQ ID NO:6 or SEQ ID NO:7, or a genetically degenerate sequence thereof (i.e. other nucleic acid sequences that encode the same protein as a result of the degeneracy of the genetic code). It is noted that SEQ ID NO:7 is the codon optimised version of the nucleic acid sequence for CDR3 of clone 1A2 (the non-optimised sequence being SEQ ID NO:6). Accordingly, the polypeptide of (b) may be encoded by the nucleic acid sequence of SEQ ID NO:6 or SEQ ID NO:7, or a genetically degenerate sequence thereof (i.e. other nucleic acid sequences that encode the same protein as a result of the degeneracy of the genetic code).

In one embodiment, the polypeptide of (b) comprises the CDR3 (e.g. the CDR3 of SEQ ID NO:5 or a variant thereof as defined above) within a TCR β chain variable region that specifically binds to the peptide of SEQ ID NO:1. In other words, the polypeptide of (b) comprises a TCR β chain variable region which includes the specified CDR3, wherein the TCR β chain variable region (and the CDR3 within it) specifically binds to the peptide of SEQ ID NO:1. As will be clear to a person of skill in the art, the phrase "TCR β chain variable region" refers to the variable (V) region (extracellular domain) of a TCR beta chain, and thus includes three hypervariable regions (CDR1, CDR2 and the specified CDR3) as well as the intervening sequences, but does not include the constant (C) region of the beta chain, which does not form part of the variable chain.

The encoded TCR β chain variable region may comprise, in addition to the specified CDR3, a CDR1 having an amino acid sequence of SEQ ID NO:16, or functional variant thereof (i.e. wherein the variant retains the ability to specifically bind to the C-terminus of the peptide of SEQ ID NO:1). Such functional variants may be naturally occurring, synthetic, or synthetically improved functional variants of SEQ ID NO:16. The term "variant" also encompasses homologues. Functional variants will typically contain only conservative substitutions of one or more amino acids of SEQ ID NO:16, or substitution, deletion or insertion of non-critical amino acids in non-critical regions of the protein.

Non-functional variants are amino acid sequence variants of SEQ ID NO: 16 that do not specifically bind to the C-terminus of the peptide of SEQ ID NO:1. Non-functional variants will typically contain a non-conservative substitution, a deletion, or insertion or premature truncation of the amino acid sequence of SEQ ID NO:16 or a substitution, insertion or deletion in critical amino acids or critical regions. Methods for identifying functional and non-functional variants are well known to a person of ordinary skill in the art.

In one embodiment, the CDR1 of (b) (e.g. within the beta chain variable region) may have an amino acid sequence having at least 80% sequence identity to the amino acid sequence of SEQ ID NO:16, whilst retaining the ability to specifically bind to the C terminus of the peptide of SEQ ID NO:1. In other words, a functional CDR1 with one amino acid substitution compared to the sequence of SEQ ID NO:16 is also encompassed. As stated previously, the amino acid substitution may be a conservative amino acid substitution. Suitably, percent identity can be calculated as the percentage of identity to the entire length of the reference sequence (e.g. SEQ ID NO:16).

In examples where the CDR1 of (b) (e.g. within the beta chain variable region) has the amino acid sequence of SEQ ID NO:16, the CDR1 may be encoded by the nucleic acid sequence of SEQ ID NO:22 or SEQ ID NO:23, or a genetically degenerate sequence thereof (i.e. other nucleic acid sequences that encode the same protein as a result of the degeneracy of the genetic code). It is noted that SEQ ID NO:23 is the codon optimised version of the nucleic acid sequence for CDR1 of clone 1A2 (the non-optimised sequence being SEQ ID NO:22). Accordingly, the polypeptide of (b) may be encoded by the nucleic acid sequence of SEQ ID NO:22 or SEQ ID NO:23, or a genetically degenerate sequence thereof (i.e. other nucleic acid sequences that encode the same protein as a result of the degeneracy of the genetic code).

The encoded TCR β chain variable region may also comprise, in addition to the specified CDR3 (and optionally the specified CDR1 above), a CDR2 having an amino acid sequence of SEQ ID NO:17, or functional variant thereof (i.e. wherein the variant retains the ability to specifically bind to HLA-A*02:01). Such functional variants may be naturally occurring, synthetic, or synthetically improved functional variants of SEQ ID NO:17. The term "variant" also encompasses homologues. Functional variants will typically contain only conservative substitutions of one or more amino acids of SEQ ID NO:17, or substitution, deletion or insertion of non-critical amino acids in non-critical regions of the protein.

Non-functional variants are amino acid sequence variants of SEQ ID NO: 17 that do not specifically bind to HLA-A*02:01. Non-functional variants will typically contain a non-conservative substitution, a deletion, or insertion or premature truncation of the amino acid sequence of SEQ ID NO:17 or a substitution, insertion or deletion in critical amino acids or critical regions. Methods for identifying functional and non-functional variants are well known to a person of ordinary skill in the art.

In one embodiment, the CDR2 of (b) (e.g. within the beta chain variable region) may have an amino acid sequence having at least 90% sequence identity to the amino acid sequence of SEQ ID NO:17, whilst retaining the ability to bind to HLA-A*02:01. In other words, a functional CDR2 with one amino acid substitution compared to the sequence of SEQ ID NO:17 is also encompassed. As stated previously, the amino acid substitution may be a conservative amino acid substitution. Suitably, percent identity can be calculated as the percentage of identity to the entire length of the reference sequence (e.g. SEQ ID NO:17).

In examples where the CDR2 of (b) (e.g. within the beta chain variable region) has the amino acid sequence of SEQ ID NO:17, the CDR2 may be encoded by the nucleic acid sequence of SEQ ID NO:24 or SEQ ID NO:25, or a genetically degenerate sequence thereof (i.e. other nucleic acid sequences that encode the same protein as a result of the degeneracy of the genetic code). It is noted that SEQ ID NO:25 is the codon optimised version of the nucleic acid sequence for CDR2 of clone 1A2 (the non-optimised sequence being SEQ ID NO:24). Accordingly, the polypeptide of (b) may be encoded by the nucleic acid sequence of SEQ ID NO:24 or SEQ ID NO:25, or a genetically degenerate sequence thereof (i.e. other nucleic acid sequences that encode the same protein as a result of the degeneracy of the genetic code).

The polypeptide of (b) may therefore comprise a TCR beta chain variable region that comprises the CDRs mentioned in detail above (by SEQ ID specifically, or variants thereof), with appropriate intervening sequences between the CDRs.

The TCR beta chain variable region of (b) may have an amino acid sequence of SEQ ID NO:11, or a functional variant thereof (i.e. wherein the variant retains the ability to specifically bind to the peptide of SEQ ID NO:1). Such functional variants may be naturally occurring, synthetic, or synthetically improved functional variants of SEQ ID NO:11. The term "variant" also encompasses homologues. Functional variants will typically contain only conservative substitutions of one or more amino acids of SEQ ID NO:11, or substitution, deletion or insertion of non-critical amino acids in non-critical regions of the protein.

Non-functional variants are amino acid sequence variants of SEQ ID NO:11 that do not specifically bind to SEQ ID NO:1. Non-functional variants will typically contain a non-conservative substitution, a deletion, or insertion or premature truncation of the amino acid sequence of SEQ ID NO:11 or a substitution, insertion or deletion in critical amino acids or critical regions. Methods for identifying functional and non-functional variants are well known to a person of ordinary skill in the art.

In one embodiment, the TCR beta chain variable region of (b) may have an amino acid sequence having at least 75%, at least 80%, at least 85%, or at least 90% (or at least 91%, at least 92%, at least 93%, at least 94%, at least 95%, at least 96%, at least 97%, at least 98%, at least 99%, or 100%) sequence identity to the amino acid sequence of SEQ ID NO:11, whilst retaining the ability to specifically bind to the peptide of SEQ ID NO:1. In other words, a functional TCR beta chain variable region with one or more amino acid substitutions compared to the sequence of SEQ ID NO:11 is also encompassed. As stated previously, the amino acid substitution may be a conservative amino acid substitution. The variability in sequence compared to SEQ ID NO:11 may all be in regions of the TCR beta chain variable region that do not form CDRs (i.e. the variant may have the CDRs of SEQ ID NO: 5, SEQ ID NO:16 and/or SEQ ID NO:17, and still have 25% (or less) sequence variability compared to SEQ ID NO:11). In other words, the sequence of the CDRs of SEQ ID NO:11 may be retained whilst the rest of the sequence is varied, as appropriate within the "at least 75% identity" parameters specified above. Suitably, percent identity can be calculated as the percentage of identity to the entire length of the reference sequence (e.g. SEQ ID NO:11).

As an example, (b) may include the CDR3 within a TCR β chain variable region having at least 75% (e.g. at least 75%, at least 80%, at least 85%, at least 90%, at least 95% etc) sequence identity to the amino acid sequence of SEQ ID NO:11, wherein the CDR3 has an amino acid sequence of SEQ ID NO: 5. In this example, the TCR β chain variable region CDR1 may have an amino acid sequence of SEQ ID NO:16 and the TCR β chain variable region CDR2 may have an amino acid sequence of SEQ ID NO:17.

In examples where the TCR beta chain variable region of (b) has the amino acid sequence of SEQ ID NO:11, the TCR beta chain variable region may be encoded by the nucleic acid sequence of SEQ ID NO:12 or SEQ ID NO:13, or a genetically degenerate sequence thereof (i.e. other nucleic acid sequences that encode the same protein as a result of the degeneracy of the genetic code). It is noted that SEQ ID NO:13 is the codon optimised version of the nucleic acid sequence for TCR beta chain variable region of clone 1A2 (the non-optimised sequence being SEQ ID NO:12). Accordingly, the polypeptide of (b) may be encoded by the nucleic acid sequence of SEQ ID NO:12 or SEQ ID NO:13, or a genetically degenerate sequence thereof (i.e. other nucleic acid sequences that encode the same protein as a result of the degeneracy of the genetic code).

For the avoidance of doubt, (b) may comprise a TCR β chain variable region (as specified above) and a TCR β chain constant region. An example of a suitable constant region is encoded in the MP71-TCR-flex retroviral vector used herein by GenScript. However, the invention is not limited to this specific constant region, and encompasses any appropriate TCR β chain constant region. The constant region may be murine derived, human derived or humanised. Methods for identifying or generating appropriate constant regions are well known to a person of skill in the art and are well within their routine capabilities.

By way of example only, the constant region may be encoded by or derived from a vector, such as a lentiviral, retroviral or plasmid vector but also adenovirus, adeno-associated virus, vaccinia virus, canary poxvirus or herpes virus vectors in which murine or human constant regions are pre-cloned. Recently, minicircles have also been described for TCR gene transfer (non-viral Sleeping Beauty transposition from minicircle vectors as published by R Monjezi, C Miskey, T Gogishvili, M Schleef, M Schmeer, H Einsele, Z Ivics and M Hudecek in Leukemia 2016). Moreover, naked (synthetic) DNA/RNA can also be used to introduce the TCR. As an example, a MP71-TCR-flex retroviral vector with pre-cloned TCR-Ca and Cb genes as used by the inventors or a pMSGV retroviral vector with pre-cloned TCR-Ca and Cb genes as described in LV Coren et al., BioTechniques 2015 may be used to provide an appropriate constant region.

In examples where the nucleic acid molecule of the invention encodes both (a) and (b), the polypeptide of (a) may be joined to the polypeptide of (b) via a linker, e.g. a linker that enables expression of two proteins or polypeptides by the same vector. By way of example, a linker comprising a porcine teschovirus-1 2A (P2A) sequence may be used, such as 2A sequences from foot-and-mouth disease virus (F2A), equine rhinitis A virus (E2A) or *Thosea asigna* virus (T2A) as published by A. L. Szymczak et al., Nature Biotechnology 22, 589-594 (2004) or 2A-like sequences. 2A and 2A-like sequences are linkers that are cleavable once the nucleic acid molecule has been transcribed and translated. Another example of a linker is an internal ribosomal entry sites (IRES) which enables translation of two proteins or polypeptides by the same transcript. Any other appropriate linker may also be used. The identification of appropriate linkers is well within the routine capabilities of a person of skill in the art. As a further example, the nucleic acid sequence encoding (a) and the nucleic acid sequence encoding (b) may be cloned into a vector with dual internal promoters (see e.g. S Jones et al., Human Gene Ther 2009).

Additional appropriate polypeptide domains may also be encoded by the nucleic acid sequence of the invention. By way of example only, the nucleic acid sequence may comprise a membrane targeting sequence that provides for transport of the encoded polypeptide to the cell surface membrane of the modified cell. Other appropriate additional domains are well known and are described, for example, in WO2016/071758.

In one embodiment, the nucleic acid sequence of the invention may encode a soluble TCR. For example, the nucleic acid sequence may encode (a) and (b), wherein (a) and (b) comprise the variable regions of the TCR alpha and beta chains respectively, and optionally an immune-modulator molecule such as a CD3 agonist (e.g. an anti-CD3 scFv). The CD3 antigen is present on mature human T cells, thymocytes and a subset of natural killer cells. It is associated with the TCR and is involved in signal transduction of the TCR. Antibodies specific for the human CD3 antigen are well known. One such antibody is the murine monoclonal antibody OKT3, which is the first monoclonal antibody approved by the FDA. Other antibodies specific for CD3 have also been reported (see e.g. WO2004/106380; U.S. Patent Application Publication No. 2004/0202657; U.S. Pat. No. 6,750,325). Immune mobilising mTCR Against Cancer (ImmTAC; Immunocore Limited, Milton Partk, Abington, Oxon, United Kingdom) are bifunctional proteins that combine affinity monoclonal T-cell receptor (mTCR) targeting with a therapeutic mechanism of action (i.e., an anti-CD3 scFv). In another example, a soluble TCR of the invention may be combined with a radioisotope or a toxic drug. Appropriate radioisotopes and/or toxic drugs are well known in the art and are readily identifiable by a person of ordinary skill in the art.

In one embodiment, the nucleic acid sequence of the invention may encode a chimeric single chain TCR in which the polypeptide of (a) (e.g. the TCR alpha chain variable region) is linked to the polypeptide of (b) (e.g. the TCR beta chain variable region) and a constant region which is e.g. fused to the CD3 zeta signalling domain. In this example, the linker is non-cleavable. In an alternative embodiment, the nucleic acid sequence of the invention may encode a chimeric two chain TCR in which the polypeptide of (a) (e.g. the TCR alpha chain variable region) and the polypeptide of (b) (e.g. the TCR beta chain variable region) are each linked to a CD3 zta signalling domain. Methods for preparing such single chain TCRs and two chain TCRs are well known in the art; see for example R A Willemsen et al, Gene Therapy 2000.

The invention also provides isolated nucleic acid sequences that encode a peptide of the invention (and corresponding vectors). All general statements herein relating to nucleic acid sequences and vectors apply equally. A person of skill in the art would readily identify suitable nucleic acid sequences and vectors on the basis of the peptide sequences provided herein.

Vectors and Modified Cells

In one aspect, the invention provides a vector that comprises a nucleic acid sequence described herein. Any appropriate vector can be used. By way of example only, the vector may be a plasmid or a viral vector, such as a retroviral vector or a lentiviral vector. Adenovirus, adeno-associated virus, vaccinia virus, canary poxvirus, herpes virus, minicircle vectors and naked (synthetic) DNA/RNA may also be used (for details on minicircle vectors, see for example non-viral Sleeping Beauty transposition from minicircle vectors as published by R Monjezi, C Miskey, T Gogishvili, M Schleef, M Schmeer, H Einsele, Z Ivics and M Hudecek in Leukemia 2016).

Optionally, the vector comprises the nucleic acid sequence operably linked to a promoter.

As used herein, the term "vector" refers to a nucleic acid sequence capable of transporting another nucleic acid sequence to which it has been operably linked. The vector can be capable of autonomous replication or it can integrate into a host DNA. The vector may include restriction enzyme sites for insertion of recombinant DNA and may include one or more selectable markers or suicide genes. The vector can be a nucleic acid sequence in the form of a plasmid, a bacteriophage or a cosmid. Preferably the vector is suitable for expression in a cell (i.e. the vector is an "expression vector"). Preferably, the vector is suitable for expression in a human T cell such as a $CD8^+$ T cell or $CD4^+$ T cell. In certain aspects, the vector is a viral vector, such as a retroviral vector, a lentiviral vector or an adeno-associated vector. Optionally, the vector is selected from the group consisting of an adenovirus, vaccinia virus, canary poxvirus, herpes virus, minicircle vector and synthetic DNA or synthetic RNA.

Preferably the (expression) vector is capable of propagation in a host cell and is stably transmitted to future generations.

"Operably linked" as used herein, refers to a single or a combination of the below-described control elements together with a coding sequence in a functional relationship with one another, for example, in a linked relationship so as to direct expression of the coding sequence.

The vector may comprise regulatory sequences. "Regulatory sequences" as used herein, refers to, DNA or RNA elements that are capable of controlling gene expression. Examples of expression control sequences include promoters, enhancers, silencers, TATA-boxes, internal ribosomal entry sites (IRES), attachment sites for transcription factors, transcriptional terminators, polyadenylation sites etc. Optionally, the vector includes one or more regulatory sequences operatively linked to the nucleic acid sequence to be expressed. Regulatory sequences include those which direct constitutive expression, as well as tissue-specific regulatory and/or inducible sequences.

The vector may comprise a promoter. "Promoter", as used herein, refers to the nucleotide sequences in DNA to which RNA polymerase binds to start transcription. The promoter may be inducible or constitutively expressed. Alternatively, the promoter is under the control of a repressor or stimulatory protein. The promoter may be one that is not naturally found in the host cell (e.g. it may be an exogenous promoter). The skilled person in the art is well aware of appropriate promoters for use in the expression of target proteins, wherein the selected promoter will depend on the host cell.

The vector may comprise a transcriptional terminator. "Transcriptional terminator" as used herein, refers to a DNA element, which terminates the function of RNA polymerases responsible for transcribing DNA into RNA. Preferred transcriptional terminators are characterized by a run of T residues preceded by a GC rich dyad symmetrical region.

The vector may comprise a translational control element. "Translational control element", as used herein, refers to DNA or RNA elements that control the translation of mRNA. Preferred translational control elements are ribosome binding sites. Preferably, the translational control element is from a homologous system as the promoter, for example a promoter and its associated ribozyme binding site. Preferred ribosome binding sites are known, and will depend on the chosen host cell.

The vector may comprise restriction enzyme recognition sites. "Restriction enzyme recognition site" as used herein, refers to a motif on the DNA recognized by a restriction enzyme.

The vector may comprise a selectable marker. "Selectable marker" as used herein, refers to proteins that, when expressed in a host cell, confer a phenotype onto the cell which allows a selection of the cell expressing said selectable marker gene. Generally this may be a protein that confers a new beneficial property onto the host cell (e.g. antibiotic resistance) or a protein that is expressed on the cell surface and thus accessible for antibody binding. Appropriate selectable markers are well known in the art.

Optionally, the vector may also comprise a suicide gene. "Suicide gene" as used herein, refers to proteins that induce death of the modified cell upon treatment with specific drugs. By way of example, suicide can be induced of cells modified by the herpes simplex virus thymidine kinase gene upon treatment with specific nucleoside analogs including ganciclovir, cells modified by human CD20 upon treatment with anti-CD20 monoclonal antibody and cells modified with inducible Caspase9 (iCasp9) upon treatment with AP1903 (reviewed by B S Jones, L S Lamb, F Goldman, A Di Stasi; Improving the safety of cell therapy products by suicide gene transfer. Front Pharmacol. (2014) 5:254. Appropriate suicide genes are well known in the art.

Preferably the vector comprises those genetic elements which are necessary for expression of the polypeptides described herein by a host cell. The elements required for transcription and translation in the host cell include a promoter, a coding region for the protein(s) of interest, and a transcriptional terminator.

A person of skill in the art will be well aware of the molecular techniques available for the preparation of (expression) vectors and how the (expression) vectors may be transduced or transfected into an appropriate host cell (thereby generating a modified cell of the invention). The (expression) vector of the present invention can be introduced into cells by conventional techniques such as transformation, transfection or transduction. "Transformation", "transfection" and "transduction" refer generally to techniques for introducing foreign (exogenous) nucleic acid sequences into a host cell, and therefore encompass methods such as electroporation, microinjection, gene gun delivery, transduction with retroviral, lentiviral or adeno-associated vectors, lipofection, superfection etc. The specific method used typically depends on both the type of vector and the cell. Appropriate methods for introducing nucleic acid sequences and vectors into host cells such as human cells are well known in the art; see for example Sambrook et al (1989) Molecular Cloning, A Laboratory Manual, Cold Spring Harbor Laboratory, Cold Spring Harbor, N.Y; Ausubel et al (1987) Current Protocols in Molecular Biology, John Wiley and Sons, Inc., NY; Cohen et al (1972) Proc. Natl. Acad. Sci. USA 69, 2110; Luchansky et al (1988) Mol. Microbiol. 2, 637-646. Further conventional methods that are suitable for preparing expression vectors and introducing them into appropriate host cells are described in detail in WO2016/071758 for example.

It is understood that it some embodiments, the host cell is contacted with the vector (e.g. viral vector) in vitro, ex vivo, and in some embodiments, the host cell is contacted with the vector (e.g. viral vector) in vivo.

The term "host cell" includes any cell into which the nucleic acid sequences or vectors of the invention cell may be introduced (e.g. transduced). Once a nucleic acid molecule or vector has been introduced into the cell, it may be referred to as a "modified cell" herein. Once the nucleic acid molecule or vector is introduced into the host cell, the resultant modified cell should be capable of expressing the encoded polypeptide (and e.g. correctly localising the encoded polypeptide for its intended function e.g. transporting the encoded TCR to the cell surface).

The term "modified cell" refers to a genetically altered (e.g. transformed or transfected) cell. The term refers to the particular subject cell and also to the progeny or potential progeny of such a cell. Because certain modifications may occur in succeeding generations due to either mutation or environmental influences, such progeny may not, in fact, be identical to the parent cell, but are still included within the scope of the term as used herein.

The host cell (and thus the modified cell) is typically a eukaryotic cell, and particularly a human cell (e.g. a T cell such as a $CD8^+$ T cell or a $CD4^+$ T cell, or a mixture thereof). The host cell (and thus the modified cell) may be an autologous cell (e.g. an autologous T cell such as a $CD8^+$ T cell or a $CD4^+$ T cell, or a mixture thereof), which refers to a cell derived from the same individual to which it is later administered. In other words, the host cell (and thus the modified cell) may be an isolated T cell from a subject to be treated. Suitably, the host cell (and thus the modified cell) may be isolated from a blood sample e.g. by leukapheresis.

The host cell (and thus the modified cell) may be any cell that is able to confer anti-tumour immunity after TCR gene transfer. Non limiting examples of appropriate cells include autologous or allogeneic Natural Killer (NK) cells, NKT cells, gamma-delta T cells, hematopoietic stem cells or other progenitor cells and any other autologous or allogeneic cell or cell line (NK-92 for example or T cell lines) that is able to confer anti-tumor immunity after TCR gene transfer.

Advantageously, the modified cell is capable of expressing the polypeptide encoded by the nucleic acid sequence or vector of the invention (e.g. the TCR or TCR component parts) such that the modified cell provides an immunotherapy that specifically targets ΔNPM1 malignant cells, and thus can be used to treat or prevent haematological malignancies having ΔNPM1. More details on this use are given below.

Immunogenic Peptides

The inventors have identified five peptides that are present in the HLA class I ligandome of ΔNPM1 positive primary AML patients, namely CLAVEEVSL (SEQ ID NO:1), AVEEVSLRK (SEQ ID NO:26), CLAVEEVSLRK (SEQ ID NO: 27), VEEVSLRK (SEQ ID NO:28) and AVEEVSLR (SEQ ID NO:29).

For the avoidance of doubt, unless specifically stated otherwise, a general reference to "SEQ ID NO:1" herein encompasses both the cysteinylated and non-cysteinylated forms of the peptide CLAVEEVSL (SEQ ID NO:1).

In the context of an isolated peptide, the invention specifically provides for an isolated peptide comprising the amino acid sequence CLAVEEVSL (SEQ ID NO:1), wherein the cysteine amino acid in CLAVEEVSL (SEQ ID NO:1) may or may not be cysteinylated.

In a specific embodiment, the cysteine amino acid in CLAVEEVSL (SEQ ID NO:1) is cysteinylated.

For the avoidance of doubt, unless specifically stated otherwise, a general reference to "SEQ ID NO:27" herein encompasses both the cysteinylated and non-cysteinylated forms of the peptide CLAVEEVSLRK (SEQ ID NO: 27).

In the context of an isolated peptide, the invention specifically provides for an isolated peptide comprising the amino acid sequence CLAVEEVSLRK (SEQ ID NO:27), wherein the cysteine amino acid in CLAVEEVSLRK (SEQ ID NO:27) may or may not be cysteinylated.

In a specific embodiment, the cysteine amino acid in CLAVEEVSLRK (SEQ ID NO: 27) is cysteinylated.

The invention therefore provides an isolated peptide comprising an amino acid sequence selected from: (i) CLAVEEVSL (SEQ ID NO:1), wherein the cysteine amino acid may or may not be cysteinylated; (ii) AVEEVSLRK (SEQ ID NO:26); (iii) CLAVEEVSLRK (SEQ ID NO: 27), wherein the cysteine amino acid may or may not be cysteinylated; (iv) VEEVSLRK (SEQ ID NO:28); and (v) AVEEVSLR (SEQ ID NO:29).

In a specific embodiment, the cysteine amino acid in CLAVEEVSL (SEQ ID NO:1) or CLAVEEVSLRK (SEQ ID NO: 27) is cysteinylated.

As used herein, an "isolated peptide" refers to a peptide that is not in its natural environment. The peptide may therefore be of synthetic origin (or alternatively, of natural original, but isolated from its natural environment).

The isolated peptide may be relatively short (i.e. no more than 20 amino acids; e.g. no more than 19, 18, 17, 16, 15, 14, 13, 12, 11, or 10 amino acids). The peptide may consist of the amino acid sequence of SEQ ID NO:1 (wherein the cysteine amino acid may or may not be cysteinylated), SEQ ID NO:26, SEQ ID NO:27 (wherein the cysteine amino acid may or may not be cysteinylated), SEQ ID NO:28 or SEQ ID NO:29 only.

In a specific embodiment, the cysteine amino acid in CLAVEEVSL (SEQ ID NO:1) or CLAVEEVSLRK (SEQ ID NO: 27) is cysteinylated.

The isolated peptide may be administered to a human subject in order to treat or prevent a ΔNPM1 positive haematological malignancy. For example, the isolated peptide may be administered to the subject in order to induce or enhance their immune response. The peptide may therefore be administered to the subject to induce T cell activation (e.g. in vivo T cell activation) in the subject, wherein the activated T cells are specific for the peptide (and thus will specifically target ΔNPM1 positive malignant cells).

The isolated peptide may be administered as a peptide vaccine for treating or preventing ΔNPM1 positive AML. The isolated peptide may be administered to induce or enhance activation of T cells specific for ΔNPM1 positive malignant cells.

The inventors have shown that (i) CLAVEEVSL (SEQ ID NO:1), (ii) AVEEVSLRK (SEQ ID NO:26); and (iii) CLAVEEVSLRK (SEQ ID NO: 27) are ΔNPM1 peptides that bind to T cells. These peptides are presented to the T cell repertoire of a ΔNPM1 positive subject in vivo. Binding of these peptides to T cells has been demonstrated herein. These peptides therefore represent bonafide immunogenic ΔNPM1-specific antigens that may be further exploited in the development of personalized vaccines, which may be particularly useful as an adjunct to other therapies (e.g. ACT as described herein). These immunogenic peptides can therefore be used as an immunotherapy in the form of peptide, RNA, DNA, dendritic cell based therapies, and adoptive TCR transgenic T cell-based therapies (for a suitable review, see ref 23).

The inventors have also shown that (iv) VEEVSLRK (SEQ ID NO:28) and (v) AVEEVSLR (SEQ ID NO:29) are HLA binding peptides presented on the surface of primary AML.

An isolated peptide comprising an amino acid sequence selected from: (i) CLAVEEVSL (SEQ ID NO:1), wherein the cysteine amino acid may or may not be cysteinylated; (ii) AVEEVSLRK (SEQ ID NO:26); (iii) CLAVEEVSLRK (SEQ ID NO: 27), wherein the cysteine amino acid may or may not be cysteinylated; (iv) VEEVSLRK (SEQ ID NO:28); and (v) AVEEVSLR (SEQ ID NO:29) may therefore be useful as an immunotherapy. For example, such isolated peptides may be used as an immunotherapy for subjects with, at risk of developing, or suspected of having ΔNPM1 positive AML. Nucleic acid sequences and vectors encoding these peptides may also be useful for this purpose.

The particular peptide for administration may be chosen based on the HLA-A status of the subject. As explained elsewhere herein, a peptide comprising the sequence of SEQ ID NO:1 may be particularly suitable for administration to a subject that is HLA-A*02:01 positive, whereas a peptide comprising the sequence of SEQ ID NO:26 or SEQ ID NO:27 may be particularly suitable for administration to a subject that is positive for HLA-A*03:01 or HLA-A*11:01.

Isolated peptides of the invention may also be provided in compositions that comprise more than one of the peptides discussed above. By way of example, an isolated peptide may be provided (and/or administered) as a composition that comprises a mixture of (a) an isolated peptide comprising the amino acid sequence CLAVEEVSL (SEQ ID NO:1), wherein the cysteine amino acid in CLAVEEVSL (SEQ ID NO:1) is cysteinylated; and (b) an isolated peptide comprising the amino acid sequence CLAVEEVSL (SEQ ID NO:1), wherein the cysteine amino acid in CLAVEEVSL (SEQ ID NO:1) is not cysteinylated. This composition may be particularly useful in treating or preventing a ΔNPM1 positive haematological malignancy in a subject that is positive for HLA-A*02:01 because it can be used to induce T cell activation (e.g. in vivo T cell activation in the subject), wherein the activated T cells have TCRs that are specific to one (or both) of the cysteinylated and/or non-cysteinylated forms of the peptide of SEQ ID NO:1.

As an alternative example, a peptide composition may be provided which comprises a mixture of (a) an isolated peptide comprising the amino acid sequence of SEQ ID NO:26 and (b) an isolated peptide comprising the amino acid sequence of SEQ ID NO:27. This composition may be particularly useful in treating or preventing a ΔNPM1 positive haematological malignancy in a subject that is positive for HLA-A*03:01 or HLA-A*11:01, as these peptides are both presented by any one of these HLA-A serotypes.

Similar to the peptide CLAVEEVSL (SEQ ID NO:1), the peptide of SEQ ID NO:27 can also be used for vaccination in its cysteinylated as well as uncysteinylated form. Therefore, as an alternative example, an isolated peptide may be provided (and/or administered) as a composition that comprises a mixture of (a) an isolated peptide comprising the amino acid sequence of SEQ ID NO:27, wherein the cysteine amino acid is cysteinylated; and (b) an isolated peptide comprising the amino acid sequence of SEQ ID NO:27, wherein the cysteine amino acid is not cysteinylated. This composition may be particularly useful in treating or preventing a ΔNPM1 positive haematological malignancy in a subject that is positive for HLA-A*03:01 or HLA-A*11:01 because it can be used to induce T cell activation (e.g. in vivo T cell activation in the subject), wherein the activated T cells have TCRs that are specific to one (or both) of the cysteinylated and/or non-cysteinylated forms of the peptide of SEQ ID NO:27.

Pharmaceutical Compositions

A nucleic acid sequence, vector, modified cell, isolated protein or peptide as described herein may be provided as part of a pharmaceutical composition. Advantageously, such compositions may be administered to a human subject having a ΔNPM1 positive haematological malignancy in order to treat or prevent the ΔNPM1 positive haematological malignancy (e.g. by inducing or enhancing a ΔNPM1-target specific immune response). A particularly suitable composition may be selected based on the HLA-A serotype of the human subject, as described in detail elsewhere herein.

A pharmaceutical composition may comprise a nucleic acid sequence, vector, modified cell or isolated protein or peptide described herein along with a pharmaceutically acceptable excipient, adjuvant, diluent and/or carrier.

Compositions may routinely contain pharmaceutically acceptable concentrations of salt, buffering agents, preservatives, compatible carriers, supplementary immune potentiating agents such as adjuvants and cytokines and optionally other therapeutic agents or compounds.

As used herein, "pharmaceutically acceptable" refers to a material that is not biologically or otherwise undesirable, i.e., the material may be administered to an individual along with the selected nucleic acid sequence, vector, modified cell or isolated peptide without causing any undesirable biological effects or interacting in a deleterious manner with any of the other components of the pharmaceutical composition in which it is contained.

Excipients are natural or synthetic substances formulated alongside an active ingredient (e.g. a nucleic acid sequence, vector, modified cell or isolated peptide as provided herein), included for the purpose of bulking-up the formulation or to confer a therapeutic enhancement on the active ingredient in the final dosage form, such as facilitating drug absorption or solubility. Excipients can also be useful in the manufacturing process, to aid in the handling of the active substance concerned such as by facilitating powder flowability or non-stick properties, in addition to aiding in vitro stability such as prevention of denaturation over the expected shelf life. Pharmaceutically acceptable excipients are well known in the art. A suitable excipient is therefore easily identifiable by one of ordinary skill in the art. By way of example, suitable pharmaceutically acceptable excipients include water, saline, aqueous dextrose, glycerol, ethanol, and the like.

Adjuvants are pharmacological and/or immunological agents that modify the effect of other agents in a formulation. Pharmaceutically acceptable adjuvants are well known in the art. A suitable adjuvant is therefore easily identifiable by one of ordinary skill in the art.

Diluents are diluting agents. Pharmaceutically acceptable diluents are well known in the art. A suitable diluent is therefore easily identifiable by one of ordinary skill in the art.

Carriers are non-toxic to recipients at the dosages and concentrations employed and are compatible with other ingredients of the formulation. The term "carrier" denotes an organic or inorganic ingredient, natural or synthetic, with which the active ingredient is combined to facilitate the application. Pharmaceutically acceptable carriers are well known in the art. A suitable carrier is therefore easily identifiable by one of ordinary skill in the art.

Treatment of a Subject

Compositions of the invention may advantageously be used to treat or prevent a ΔNPM1 positive haematological malignancy in a human subject. An appropriate composition may be selected on the basis of the HLA-A serotype of the human subject, as discussed in detail elsewhere herein.

In one embodiment, the method of treatment or prevention of a ΔNPM1 positive haematological malignancy described herein results in an induced or enhanced immune response (e.g. a cell mediated response) in the subject (e.g. a targeted immune response to malignant cells that present the HLA-A restricted peptide).

The phrase "induced or enhanced immune response" refers to an increase in the immune response (e.g. cell mediated immune response such as a T cell mediated immune response) of the subject during or after treatment compared to their immune response prior to treatment. An "induced or enhanced" immune response therefore encompasses any measurable increase in the immune response that is directly or indirectly targeted to the ΔNPM1 positive haematological malignancy being treated.

Compositions of the invention may be used to treat or prevent a ΔNPM1 positive haematological malignancy in a human subject, particularly a ΔNPM1 positive myeloid malignancy, and more particularly ΔNPM1 positive AML.

A person of skill in the art will be fully aware of haematological malignancies that may be ΔNPM1 positive and thus may be treated in accordance with the invention. Similarly, a person of skill in the art will be fully aware of myeloid malignancies that may be ΔNPM1 positive and thus may be treated in accordance with the invention.

As used herein, the terms "treat", "treating" and "treatment" are taken to include an intervention performed with the intention of preventing the development or altering the pathology of a condition, disorder or symptom (i.e. in this case a haematological malignancy). Accordingly, "treatment" refers to both therapeutic treatment and prophylactic or preventative measures, wherein the object is to prevent or slow down (lessen) the targeted condition, disorder or symptom. "Treatment" therefore encompasses a reduction, slowing or inhibition of the amount or concentration of malignant cells, for example as measured in a sample obtained from the subject, of at least 5%, 10%, 20%, 30%, 40%, 50%, 60%, 70%, 80%, 90% or 100% when compared to the amount or concentration of malignant cells before treatment. Methods of measuring the amount or concentration of malignant cells include, for example, qRT-PCR, and quantification of ΔNPM1 positive haematological malignancy specific biomarkers, such as CLAVEEVSL (SEQ ID NO:1), AVEEVSLRK (SEQ ID NO:26), CLAVEEVSLRK (SEQ ID NO: 27), VEEVSLRK (SEQ ID NO:28), and/or AVEEVSLR (SEQ ID NO:29) in a sample obtained from the subject.

As used here in the term "subject" refers to an individual, e.g., a human, having or at risk of having a specified condition, disorder or symptom. The subject may be a patient i.e. a subject in need of treatment in accordance with the invention. The subject may have received treatment for the condition, disorder or symptom. Alternatively, the subject has not been treated prior to treatment in accordance with the present invention.

The compositions described herein can be administered to the subject by any conventional route, including injection or by gradual infusion over time. The administration may, for example, be by infusion or by intramuscular, intravascular, intracavity, intracerebral, intralesional, rectal, subcutaneous, intradermal, epidural, intrathecal, percutaneous administration.

The compositions described herein may be in any form suitable for the above modes of administration. For example, compositions comprising modified cells may in any form suitable for infusion. As further examples, suitable forms for parenteral injection (including, subcutaneous, intramuscular, intravascular or infusion) include a sterile solution, suspension or emulsion; suitable forms for topical administration include an ointment or cream; and suitable forms for rectal administration include a suppository. Alternatively, the route of administration may be by direct injection into the target area, or by regional delivery or by local delivery. The identification of suitable dosages of the compositions of the invention is well within the routine capabilities of a person of skill in the art.

Advantageously, the compositions of the invention may be formulated for use in T cell receptor (TCR) gene transfer, an approach that is rapid, reliable and capable of generating large quantities of T cells with specificity for the ΔNPM1-specific peptide (e.g. CLAVEEVSL (SEQ ID NO:1), AVEEVSLRK (SEQ ID NO:26), CLAVEEVSLRK (SEQ ID NO:27), VEEVSLRK (SEQ ID NO:28), or AVEEVSLR (SEQ ID NO:29)), regardless of the patient's pre-existing immune repertoire. Using TCR gene transfer, modified autologous cells suitable for infusion may be generated within a few days.

Advantageously, the compositions of the invention may be formulated for use as a vaccine (e.g. a composition comprising one or more peptides selected from CLAVEEVSL (SEQ ID NO:1), AVEEVSLRK (SEQ ID NO:26), CLAVEEVSLRK (SEQ ID NO:27), VEEVSLRK (SEQ ID NO:28), or AVEEVSLR (SEQ ID NO:29) may be formulated as a pharmaceutical composition that is suitable for use as a peptide vaccine. Suitable peptide vaccine formulations are well known in the art.

Preferably, the pharmaceutical composition of the invention is a vaccine, preferably a peptide-based vaccine. Such a peptide-based vaccine may be used for the prevention or treatment of ΔNPM1 positive haematological malignancies such as AML.

The pharmaceutical composition is preferably for, and therefore formulated to be suitable for, administration to a subject, preferably a human or animal subject. Preferably, the administration is parenteral, e.g. intravenous, subcutaneous, intramuscular, intradermal intracutaneous and/or intratumoral administration, i.e. by injection.

Preferably, the pharmaceutical composition comprises or consists of an amount of peptide that constitutes a pharmaceutical dosage unit. A pharmaceutical dosage unit is defined herein as the amount of active ingredients (i.e. the total amount of peptide in a peptide-based vaccine) that is applied to a subject at a given time point. A pharmaceutical dosage unit may be applied to a subject in a single volume, i.e. a single shot, or may be applied in 2, 3, 4, 5 or more separate volumes or shots that are applied preferably at different locations of the body, for instance in the right and the left limb. It is to be understood herein that the separate volumes of a pharmaceutical dosage may differ in composition, i.e. may comprise different kinds or composition of active ingredients and/or adjuvants.

A single injection volume or shot (i.e. volume applied on one location at a certain time point), comprising a total pharmaceutical dosage, or part thereof in case multiple shots applied at substantially the same time point, may between 100 and 2 mL, or between 100 and 1 mL. The single injection volume may be 100 µl, 200 µl, 300 µl, 400 µl, 500 µl, 600 µl, 700 µl, 800 µl, 900 µl, 1 mL, 1.1 mL, 1.2 mL, 1.3 mL, 1.4 mL, 1.5 mL, 1.6 mL, 1.7 mL, 1.8 mL, 1.9 mL, 2 mL, 3 mL or any value in between.

Preferably, pharmaceutical dosage unit, or total amount of peptide applied to a subject at a given time point, either in a single or in multiple injections at a certain time point, comprises an amount of peptide in the range from 0.1 µg to 20 mg, such as about 0.1 µg, 0.5 µg, 1 µg, 5 µg, 10 µg, 15 µg, 20 µg, 30 µg, 40 µg, 50 µg, 60 µg, 70 µg, 80 µg, 90 µg, 100 µg, 150 µg, 200 µg, 250 µg, 300 µg, 350 µg, 400 µg, 450 µg, 500 µg, 650 µg, 700 µg, 750 µg, 800 µg, 850 µg, 900 µg, 1 mg, 1.5 mg, 2 mg, 2.5 mg, 3 mg, 3.5 mg, 4 mg, 4.5 mg, 5 mg, 5.5 mg, 6 mg, 6.5 mg, 7 mg, 7.5 mg, 8 mg, 8.5 mg, 9 mg, 9.5 mg, 10 mg, 15 mg or about 20 mg or any value in between. Preferred ranges of pharmaceutical dosage units are from 0.1 µg to 20 mg, 1 µg to 10 mg, 10 µg to 5 mg, 0.5 mg to 2 mg, 0.5 mg to 10 mg or 1 mg to 5 mg or 2 to 4 mg.

The compositions described herein are for administration in an effective amount. An "effective amount" is an amount that alone, or together with further doses, produces the desired (therapeutic or non-therapeutic) response. The effective amount to be used will depend, for example, upon the therapeutic (or non-therapeutic) objectives, the route of administration, and the condition of the patient/subject. For example, the suitable dosage of the composition of the invention for a given patient/subject will be determined by the attending physician (or person administering the composition), taking into consideration various factors known to modify the action of the composition of the invention for example severity and type of haematological malignancy, body weight, sex, diet, time and route of administration, other medications and other relevant clinical factors. The dosages and schedules may be varied according to the particular condition, disorder or symptom the overall condition of the patient/subject. Effective dosages may be determined by either in vitro or in vivo methods.

The compositions of the present invention are advantageously presented in unit dosage form.

Methods of Generating TCRs

In one aspect, the invention provides a method of generating a T cell receptor that specifically binds to a peptide selected from CLAVEEVSL (SEQ ID NO:1), AVEEVSLRK (SEQ ID NO:26), CLAVEEVSLRK (SEQ ID NO:27), VEEVSLRK (SEQ ID NO:28), and AVEEVSLR (SEQ ID NO:29), the method comprising contacting a nucleic acid sequence of the invention (or vector) with a host cell under conditions in which the nucleic acid sequence (or vector) is incorporated and expressed by the cell to generate the T cell receptor.

The method may be carried out on the host cell ex vivo or in vitro. Alternatively, the method may be performed in vivo, wherein the nucleic acid sequence (or vector) is administered to the subject and is contacted with the host cell in vivo, under conditions in which the nucleic acid sequence is incorporated and expressed by the host cell to generate the T cell receptor. In one embodiment, the method is not a method of treatment of the human or animal body.

Appropriate in vivo, in vitro and ex vivo methods for contacting a nucleic acid sequence (or vector) with a host cell under conditions in which the nucleic acid sequence (or vector) is incorporated and expressed by the cell are well known, as described elsewhere herein.

General Definitions

As used herein "nucleic acid sequence", "polynucleotide", "nucleic acid" and "nucleic acid molecule" are used interchangeably to refer to an oligonucleotide sequence or polynucleotide sequence. The nucleotide sequence may be of genomic, synthetic or recombinant origin, and may be double-stranded or single-stranded (representing the sense or antisense strand). The term "nucleotide sequence" includes genomic DNA, cDNA, synthetic DNA, and RNA (e.g. mRNA) and analogs of the DNA or RNA generated, e.g., by the use of nucleotide analogs.

As used herein, "isolated nucleic acid sequence" refers to a nucleic acid sequence that is not in its natural environment when it is linked to its naturally associated sequence(s) that is/are also in its/their natural environment. In other words, an isolated nucleic acid sequence is not a native nucleotide sequence, wherein "native nucleotide sequence" means an entire nucleotide sequence that is in its native environment and when operatively linked to an entire promoter with which it is naturally associated, which promoter is also in its native environment.

As used herein, "specifically binds to CLAVEEVSL" (SEQ ID NO:1) refers to selective binding of the CLAVEEVSL (SEQ ID NO:1) peptide. Under certain conditions, for example in an immunoassay as described herein, a polypeptide that "specifically binds to CLAVEEVSL" (SEQ ID NO:1) will selectively bind to this peptide and will not bind in a significant amount to other peptides. Thus the polypeptide may bind to CLAVEEVSL (SEQ ID NO:1) with at least 10, 20, 30, 40, 50, or 100 fold more affinity than it binds to a control antigenic peptide. Selective binding may also be determined indirectly in the context of a modified cell that expresses a nucleic acid or vector of the invention. In assays such as, for example, an assay discussed herein, the modified cell is specifically reactive against a cell presenting CLAVEEVSL (SEQ ID NO:1) in the context of HLA-A*02:01 (e.g. primary ΔNPM1 HLA-A*02:01 positive AML cells, or any HLA-A*02:01 positive cell line in which the ΔNPM1 gene is introduced). Thus, the modified cell may bind to a cell presenting CLAVEEVSL (SEQ ID NO:1) in the context of HLA-A*02:01 with at least 10, 20, 30, 40, 50, or 100 fold more reactivity when compared to its reactivity against a control cell line that does not present CLAVEEVSL (SEQ ID NO:1) in the context of HLA-A*02:01.

The selective binding may be in the context of CLAVEEVSL (SEQ ID NO:1) presentation by HLA-A*02:01. In other words, in certain embodiments, a polypeptide that "specifically binds to CLAVEEVSL (SEQ ID NO:1)" may only do so when it is being presented (i.e. it is bound by) HLA-A*02:01, or is in an equivalent structural formation as when it is being presented by HLA-A*02:01.

Unless stated to the contrary, a polypeptide that "specifically binds CLAVEEVSL" (SEQ ID NO:1) may bind to either (i) the cysteinylated form of CLAVEEVSL (SEQ ID NO:1), (ii) the non-cysteinylated form of CLAVEEVSL (SEQ ID NO:1), or (iii) both the cysteinylated form of CLAVEEVSL (SEQ ID NO:1) and the non-cysteinylated form of CLAVEEVSL (SEQ ID NO:1). Likewise, unless specifically stated otherwise, a general reference herein to "SEQ ID NO:1" or "CLAVEEVSL" encompasses both the cysteinylated and non-cysteinylated forms of the peptide CLAVEEVSL (SEQ ID NO:1).

As used herein, "specifically binds to AVEEVSLRK" (SEQ ID NO:26) refers to selective binding of the AVEEVSLRK (SEQ ID NO:26) peptide. Under certain conditions, for example in an immunoassay as described herein, a polypeptide that "specifically binds to AVEEVSLRK (SEQ ID NO:26)" will selectively bind to this peptide and will not bind in a significant amount to other peptides. Thus the polypeptide may bind to AVEEVSLRK (SEQ ID NO:26) with at least 10, 20, 30, 40, 50, or 100 fold more affinity than it binds to a control antigenic peptide. Selective binding may also be determined indirectly in the context of a modified cell that expresses a nucleic acid or vector of the invention. In assays such as, for example, an assay discussed herein, the modified cell is specifically reactive against a cell presenting AVEEVSLRK (SEQ ID NO:26) in the context of HLA-A*03:01, HLA-A*11:01 or HLA-A*01:01 (e.g. primary ΔNPM1 HLA-A*03:01, HLA-A*11:01 or HLA-A*01:01 positive AML cells, or any HLA-A*03:01, HLA-A*11:01 or HLA-A*01:01 positive cell line in which the ΔNPM1 gene is introduced). Thus, the modified cell may bind to a cell presenting AVEEVSLRK (SEQ ID NO:26) in the context of HLA-A*03:01, HLA-A*11:01 or HLA-A*01:01 with at least 10, 20, 30, 40, 50, or 100 fold more reactivity when compared to its reactivity against a control cell line that does not present AVEEVSLRK (SEQ ID NO:26) in the context of HLA-A*03:01, HLA-A*11:01 or HLA-A*01:01.

The selective binding may be in the context of AVEEVSLRK (SEQ ID NO:26) presentation by HLA-A*03:01, HLA-A*11:01 or HLA-A*01:01 only. In other words, in certain embodiments, a polypeptide that "specifically binds to AVEEVSLRK" (SEQ ID NO:26) may only do so when it is being presented (i.e. it is bound by) HLA-A*03:01, HLA-A*11:01 or HLA-A*01:01, or is in an equivalent structural formation as when it is being presented by HLA-A*03:01, HLA-A*11:01 or HLA-A*01:01.

Similarly, as used herein, "specifically binds to CLAVEEVSLRK" (SEQ ID NO:27) refers to selective binding of the CLAVEEVSLRK (SEQ ID NO: 27) peptide. Under certain conditions, for example in an immunoassay as described herein, a polypeptide that "specifically binds to CLAVEEVSLRK" (SEQ ID NO:27) will selectively bind to this peptide and will not bind in a significant amount to other peptides. Thus the polypeptide may bind to CLAVEEVSLRK (SEQ ID NO: 27) with at least 10, 20, 30, 40, 50, or 100 fold more affinity than it binds to a control antigenic peptide. Selective binding may also be determined indirectly in the context of a modified cell that expresses a nucleic acid or vector of the invention. In assays such as, for example, an assay discussed herein, the modified cell is specifically reactive against a cell presenting CLAVEEVSLRK (SEQ ID NO: 27) in the context of HLA-A*03:01 or HLA-A*11:01 (e.g. primary ΔNPM1 HLA-A*03:01 or HLA-A*11:01 positive AML cells, or any HLA-A*03:01 or HLA-A*11:01 positive cell line in which the ΔNPM1 gene is introduced). Thus, the modified cell may bind to a cell presenting CLAVEEVSLRK (SEQ ID NO: 27) in the context of HLA-A*03:01 or HLA-A*11:01 with at least 10, 20, 30, 40, 50, or 100 fold more reactivity when compared to its reactivity against a control cell line that does not present CLAVEEVSLRK (SEQ ID NO: 27) in the context of HLA-A*03:01 or HLA-A*11:01.

The selective binding may be in the context of CLAVEEVSLRK (SEQ ID NO: 27) presentation by HLA-A*03:01 or HLA-A*11:01 only. In other words, in certain embodiments, a polypeptide that "specifically binds to CLAVEEVSLRK" (SEQ ID NO:27) may only do so when it is being presented (i.e. it is bound by) HLA-A*03:01 or HLA-A*11:01, or is in an equivalent structural formation as when it is being presented by HLA-A*03:01 or HLA-A*11:01.

Unless stated to the contrary, a polypeptide that "specifically binds CLAVEEVSLRK (SEQ ID NO: 27)" may bind to either (i) the cysteinylated form of CLAVEEVSLRK (SEQ ID NO: 27), (ii) the non-cysteinylated form of CLAVEEVSLRK (SEQ ID NO: 27), or (iii) both the cysteinylated form of CLAVEEVSLRK (SEQ ID NO: 27) and the non-cysteinylated form of CLAVEEVSLRK (SEQ ID NO: 27). Likewise, unless specifically stated otherwise, a general reference herein to "SEQ ID NO:27" or "CLAVEEVSLRK" encompasses both the cysteinylated and non-cysteinylated forms of the peptide CLAVEEVSLRK (SEQ ID NO: 27).

As used herein, "specifically binds to VEEVSLRK" (SEQ ID NO:28) refers to selective binding of the VEEVSLRK (SEQ ID NO:28) peptide. Under certain conditions, for example in an immunoassay as described herein, a polypeptide that "specifically binds to VEEVSLRK" (SEQ ID NO:28) will selectively bind to this peptide and will not bind in a significant amount to other peptides. Thus the polypeptide may bind to VEEVSLRK (SEQ ID NO:28) with at least 10, 20, 30, 40, 50, or 100 fold more affinity than it binds to a control antigenic peptide. Selective binding may also be determined indirectly in the context of a modified cell that expresses a nucleic acid or vector of the invention. In assays such as, for example, an assay discussed herein, the modified cell is specifically reactive against a cell presenting VEEVSLRK (SEQ ID NO:28) in the context of the appropriate HLA-A (e.g. primary ΔNPM1 positive AML cells, or any appropriate HLA-A positive cell line in which the ΔNPM1 gene is introduced). Thus, the modified cell may bind to a cell presenting VEEVSLRK (SEQ ID NO:28) in the context of and appropriate HLA-A with at least 10, 20, 30, 40, 50, or 100 fold more reactivity when compared to its reactivity against a control cell line that does not present VEEVSLRK (SEQ ID NO:28) in the context of the appropriate HLA-A.

The selective binding may be in the context of VEEVSLRK (SEQ ID NO:28) presentation by an appropriate HLA-A only. In other words, in certain embodiments, a polypeptide that "specifically binds to VEEVSLRK" (SEQ ID NO:28) may only do so when it is being presented (i.e. it is bound by) an appropriate HLA-A, or is in an equivalent structural formation as when it is being presented by an appropriate HLA-A.

As used herein, "specifically binds to AVEEVSLR" (SEQ ID NO:29) refers to selective binding of the AVEEVSLR (SEQ ID NO:29) peptide. Under certain conditions, for example in an immunoassay as described herein, a polypeptide that "specifically binds to AVEEVSLR" (SEQ ID NO:29) will selectively bind to this peptide and will not bind in a significant amount to other peptides. Thus the polypeptide may bind to AVEEVSLR (SEQ ID NO:29) with at least 10, 20, 30, 40, 50, or 100 fold more affinity than it binds to a control antigenic peptide. Selective binding may also be determined indirectly in the context of a modified cell that expresses a nucleic acid or vector of the invention. In assays such as, for example, an assay discussed herein, the modified cell is specifically reactive against a cell presenting AVEEVSLR (SEQ ID NO:29) in the context of the appropriate HLA-A (e.g. primary ΔNPM1 positive AML cells, or any appropriate HLA-A positive cell line in which the ΔNPM1 gene is introduced). Thus, the modified cell may bind to a cell presenting AVEEVSLR (SEQ ID NO:29) in the context of and appropriate HLA-A with at least 10, 20, 30, 40, 50, or 100 fold more reactivity when compared to its reactivity against a control cell line that does not present AVEEVSLR (SEQ ID NO:29) in the context of the appropriate HLA-A.

The selective binding may be in the context of AVEEVSLR (SEQ ID NO:29) presentation by an appropriate HLA-A only. In other words, in certain embodiments, a polypeptide that "specifically binds to AVEEVSLR" may only do so when it is being presented (i.e. it is bound by) an appropriate HLA-A, or is in an equivalent structural formation as when it is being presented by an appropriate HLA-A.

A "non-essential" (or "non-critical") amino acid residue is a residue that can be altered from the wild-type sequence of (e.g., the sequence identified by SEQ ID NO herein) without abolishing or, more preferably, without substantially altering a biological activity, whereas an "essential" (or "critical") amino acid residue results in such a change. For example, amino acid residues that are conserved are predicted to be particularly non-amenable to alteration, except that amino acid residues within the hydrophobic core of domains can generally be replaced by other residues having approximately equivalent hydrophobicity without significantly altering activity.

A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), non-polar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Thus, a nonessential (or non-critical) amino acid residue in a protein is preferably replaced with another amino acid residue from the same side chain family. Alternatively, in another embodiment, mutations can be introduced randomly, and the resultant mutants can be screened for activity to identify mutants that retain activity.

Calculations of sequence homology or identity (the terms are used interchangeably herein) between sequences are performed as follows.

To determine the percent identity of two amino acid sequences, or of two nucleic acid sequences, the sequences are aligned for optimal comparison purposes (e.g., gaps can be introduced in one or both of a first and a second amino acid or nucleic acid sequence for optimal alignment and non-homologous sequences can be disregarded for comparison purposes). In a preferred embodiment, the length of a reference sequence aligned for comparison purposes is at least 30%, preferably at least 40%, more preferably at least 50%, even more preferably at least 60%, and even more preferably at least 70%, 75%, 80%, 82%, 84%, 85%, 86%, 87%, 88%, 89%, 90%, 91%, 92%, 93%, 94%, 95%, 96%, 97%, 98%, 99%, or 100% of the length of the reference sequence. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position (as used herein amino acid or nucleic acid "identity" is equivalent to amino acid or nucleic acid "homology"). The percent identity between the two sequences is a function of the number of identical positions shared by the sequences, taking into account the number of gaps, and the length of each gap, which need to be introduced for optimal alignment of the two sequences.

The comparison of sequences and determination of percent identity between two sequences can be accomplished using a mathematical algorithm. In a preferred embodiment, the percent identity between two amino acid sequences is determined using the Needleman et al. (1970) *J. Mol. Biol.* 48:444-453) algorithm which has been incorporated into the GAP program in the GCG software package (available at the GCG website), using either a BLOSUM 62 matrix or a PAM250 matrix, and a gap weight of 16, 14, 12, 10, 8, 6, or 4 and a length weight of 1, 2, 3, 4, 5, or 6. In yet another preferred embodiment, the percent identity between two nucleotide sequences is determined using the GAP program in the GCG software package (available at the GCG website), using a NWSgapdna.CMP matrix and a gap weight of 40, 50, 60, 70, or 80 and a length weight of 1, 2, 3, 4, 5, or 6. A particularly preferred set of parameters (and the one that should be used if the practitioner is uncertain about what parameters should be applied to determine if a molecule is within a sequence identity or homology limitation of the invention) are a BLOSUM 62 scoring matrix with a gap penalty of 12, a gap extend penalty of 4, and a frameshift gap penalty of 5.

Alternatively, the percent identity between two amino acid or nucleotide sequences can be determined using the algorithm of Meyers et al. (1989) CABIOS 4:11-17) which has been incorporated into the ALIGN program (version 2.0), using a PAM120 weight residue table, a gap length penalty of 12 and a gap penalty of 4.

The nucleic acid and protein sequences described herein can be used as a "query sequence" to perform a search against public databases to, for example, identify other family members or related sequences. Such searches can be performed using the NBLAST and XBLAST programs (version 2.0) of Altschul, et al. (1990) *J. Mol. Biol.* 215: 403-410). BLAST nucleotide searches can be performed with the NBLAST program, score=100, wordlength=12 to obtain nucleotide sequences homologous to nucleic acid molecules of the invention. BLAST protein searches can be performed with the XBLAST program, score=50, wordlength=3 to obtain amino acid sequences homologous to protein molecules of the invention. To obtain gapped alignments for comparison purposes, gapped BLAST can be utilized as described in Altschul et al. (1997, *Nucl. Acids Res.* 25:3389-3402). When using BLAST and gapped BLAST programs, the default parameters of the respective programs (e.g., XBLAST and NBLAST) can be used. See the NCBI website.

The polypeptides and nucleic acid molecules described herein can have amino acid sequences or nucleic acid sequences sufficiently or substantially identical to the sequences identified by SEQ ID NO. The terms "sufficiently identical" or "substantially identical" are used herein to refer to a first amino acid or nucleotide sequence that contains a sufficient or minimum number of identical or equivalent (e.g. with a similar side chain) amino acid residues or nucleotides to a second amino acid or nucleotide sequence such that the first and second amino acid or nucleotide sequences have a common structural domain or common functional activity. For example, amino acid or nucleotide sequences that contain a common structural domain having at least about 60%, or 65% identity, likely 75% identity, more likely 85%, 90%, 91%, 92%, 93%, 94%, 95%, 96%, 97%, 98% or 99% identity are defined herein as sufficiently or substantially identical.

Unless defined otherwise herein, all technical and scientific terms used herein have the same meaning as commonly understood by one of ordinary skill in the art to which this invention pertains. For example, Singleton and Sainsbury, Dictionary of Microbiology and Molecular Biology, 2d Ed., John Wiley and Sons, NY (1 94); and Hale and Marham, The Harper Collins Dictionary of Biology, Harper Perennial, NY (1991) provide those of skill in the art with a general dictionary of many of the terms used in the invention. Although any methods and materials similar or equivalent to those described herein find use in the practice of the present invention, the preferred methods and materials are described herein. Accordingly, the terms defined immediately below are more fully described by reference to the Specification as a whole. Also, as used herein, the singular terms "a", "an," and "the" include the plural reference unless the context clearly indicates otherwise. Unless otherwise indicated, nucleic acids are written left to right in 5' to 3' orientation; amino acid sequences are written left to right in amino to carboxy orientation, respectively. It is to be understood that this invention is not limited to the particular methodology, protocols, and reagents described, as these may vary, depending upon the context they are used by those of skill in the art.

Aspects of the invention are demonstrated by the following non-limiting examples.

EXAMPLES

Materials and Methods
Study Design

The objectives of this study were (1) to identify HLA class I ligands from ΔNPM1 on primary AML, (2) to isolate CD8 cells with TCRs specific for HLA class I ligands from ΔNPM1 and (3) to identify TCRs for HLA class I ligands from ΔNPM1 that are capable of mediating specific recognition and lysis of primary AML after gene transfer. HLA class I ligandome data were generated for 12 primary AML using tandem mass spectrometry and searched for peptides matching the alternative reading frame of ΔNPM1. HLA-A*02:01 pMHC tetramers were produced for one identified peptide and used to isolate specific CD8 cells from 6 HLA-A*02:01 positive AML patients and 6 healthy HLA-A*02:01 positive individuals. T cell clones isolated from healthy individuals were screened for pMHC tetramer staining and tetramer positive T cell clones were tested for reactivity against peptide-loaded T2 cells and primary AML with ΔNPM1 or wtNPM1 by IFN-γ ELISA. From one strongly reactive T cell clone, the TCR was sequenced and cloned into the retroviral MP71-TCR-flex vector. This vector was used to introduce the TCR into CD8 and CD4 cells from two healthy HLA-A*02:01 positive individuals and the purity of TCR-transduced T cells was assessed by flow cytometry. TCR-transduced T cells were tested for recognition of HLA-A*02:01 positive AML cell lines and primary AML with ΔNPM1 or wtNPM1 by IFN-γ ELISA and specific lysis was measured by $^{51}$Cr release assays.

Sample Collection and Cell Culture

Peripheral blood and bone marrow samples were collected from patients with AML and healthy individuals after approval by the Institutional Review Board of the Leiden University Medical Center with informed consent according to the Declaration of Helsinki. Peripheral blood and bone marrow mononuclear cells were isolated by Ficoll-Isopaque separation and cryopreserved. For isolation of PBMC from HLA-A*02:01-typed healthy individuals, buffy coats were ordered from Sanquin (Amsterdam, the Netherlands). T cells were cultured in T cell medium (TCM) consisting of Iscove's Modified Dulbecco's Medium (IMDM; Lonza, Basel, Switzerland) supplemented with 5% heat-inactivated fetal bovine serum (FBS; Gibco, Thermo Fisher Scientific, Waltham, Mass., United States), 5% human serum, 1.5% L-glutamine (Lonza), 1% penicillin/streptomycin (Lonza) and 100 IU/ml IL-2 (Novartis, Basel, Switzerland). AML cell lines expressing wild type NPM1 (OCI-AML2) and ΔNPM1 (OCI-AML3) were ordered from DSMZ (Braunschweig, Germany) and cultured in minimum essential medium alpha (MEMα; Gibco) with 20% FBS and 1% penicillin/streptomycin. Primary AML and T2 cells were cultured in IMDM containing 10% FBS, 1.5% L-glutamine and 1% penicillin/streptomycin. Monocytes were isolated from PBMC by magnetic-activated cell sorting (MACS; Miltenyi Biotec, Bergisch Gladbach, Germany) with CliniMACS CD14 beads (Miltenyi Biotec). Isolated monocytes were cultured to immature dendritic cells (DC) in medium with 100 ng/mL GM-CSF (Novartis, Basel, Switzerland)

and 500 IU/mL IL-4 (Schering-Plough, Kenilworth, N.J.) for 7 days. During the final two days 100 ng/mL GM-CSF, 10 ng/mL TNF-α (Cellgenix, Freiburg, Germany), 10 ng/mL IL-1β (Cellgenix), 10 ng/mL IL-6 (Cellgenix), 1 µg/mL prostaglandin E2 (Sigma-Aldrich, St. Louis, Mo.), and 500 IU/mL IFN-γ (Boehringer-Ingelheim, Ingelheim, Germany) were added to induce maturation.

HLA Class I Ligandome of Primary AML

Cell pellets of 12 primary AML samples were lysed in 50 mM Tris-HCl, 150 mM NaCl, 5 mM ethylenediaminetetraacetate and 0.5% Zwittergent 3-12 (pH 8.0) and supplemented with Complete protease inhibitor (Sigma-Aldrich, St. Louis, Mo., United States). After 2 hrs. incubation with tumbling of cells in lysis buffer at 4° C., the preparation was centrifuged for 10 min. at 1000 g at 4° C. The supernatant was transferred to a new tube and centrifuged for 35 min. at 13,000 g at 4° C. The supernatant was pre-cleared with Protein A Sepharose CL-4B beads (GE Healthcare Life Sciences, Chicago, Ill., United States) and subjected to an immunoaffinity column with dimethyl pimelidate (DMP) immobilized W6/32 antibody (3 mg/ml resin) on Protein A Sepharose CL-4B beads with a flow rate of 1 ml/min. After washing of 5-10 column volumes with lysis buffers and 10 mM Tris-HCl (pH 8.0) buffers with 1 M, 120 mM and no NaCl, bound HLA class I-peptide complexes were eluted from the column and dissociated with 3-4 column volumes 10% acetic acid. Peptides were separated from the HLA class I molecules via passage through a 10 kDa membrane (Macrosep Advance Centrifugal Devices With Supor Membrane, Pall Corporation, Port Washington, N.Y., United States). The filtrate was freeze dried.

Eluted peptide pools were fractionated by strong cation exchange chromatography (SCX) with a homemade SCX column (320 µm inner diameter, 15 cm, polysulfoethyl A 3 µm, Poly LC) run at 4 µl/min. Gradients were run for 10 min. at 100% solvent A (100/0.1 water/trifluoroacetic acid v/v), after which a linear gradient started to reach 100% solvent B (65/35/0.1 250 mM KCl/acetonitrile/trifluoroacetic acid v/v/v) over 15 min., followed by 100% solvent C (65/35/0.1 500 mM KCl/acetonitrile/trifluoroacetic acid v/v/v) over the next 15 min. The gradient remained at 100% solvent C for 5 min. and then switched again to 100% solvent A. Twenty 4 µl fractions were collected in vials prefilled with 20 µl 95/3/0.1 water/acetonitrile/FA v/v/v. Peptide fractions were lyophilized, dissolved in 95/3/0.1 water/acetonitril/formic acid v/v/v and subsequently analyzed by data dependent tandem mass spectrometry (MS) on either a LTQ-FTUltra equipped with a nanoflow liquid chromatography 1100 HPLC system (Agilent Technologies, Santa Clara, Calif., United States), as previously described (38), or a Q-Exactive equipped with an easy-nLC1000. Peptides were trapped at 6-10 µl/min on a 1.5 cm column (100-µm internal diameter; ReproSil-Pur C18-AQ, 3 µm, Dr. Maisch HPLC GmbH, Ammerbuch-Entringen, Germany) and eluted to a 20 cm column (50-µm internal diameter; ReproSil-Pur C18-AQ, 3 µm) at 150 nl/min. The column was developed with a 120 min. gradient from 0 to 40% acetonitrile in 0.1% formic acid. The end of the column was drawn to a tip (internal diameter about 5 µm) from which the eluent was sprayed into the mass spectrometer. Full scan MS spectra were acquired in the FT-ICR with a resolution of 25,000 at a target value of 3,000,000. The two most intense ions were isolated for accurate mass measurements by a selected ion monitoring scan in FT-ICR with a resolution of 50,000 at a target accumulation value of 50,000. The selected ions were then fragmented in the linear ion trap using collision-induced dissociation at a target value of 10,000. The Q-Exactive mass spectrometer was operated in tool 0-mode. Parameters were resolution 70,000 at an AGC target value of 3,000,000/maximum fill time of 20 ms (full scan) and resolution 17,500 at an AGC target value of 100,000/maximum fill time of 60 ms for MS/MS at an intensity threshold of 17,000. Apex trigger was set to 1 to 10 s. and allowed charges were 2-6. Proteome Discoverer version 2.1 (Thermo Fisher Scientific) was used for peptide and protein identification, using the mascot node for identification, using mascot version 2.2.04 with the UniProt *Homo sapiens* database (UP000005640; January 2015; 67911 entries). Methionine oxidation and cysteinylation of cysteine were set as a variable modification. Peptide assignments were made with a precursor tolerance of 10 ppm and MS/MS fragment tolerance of 20 mmu for the Q-Exactive data and 2 ppm and 0.5 Da for LTQ-FTUltra data. Identification of the ΔNPM1-derived peptide was confirmed by its synthetic counterpart.

Peptide Synthesis and pMHC Tetramer Production

Peptides were synthesized by standard Fmoc chemistry and dissolved in dimethyl sulfoxide. Cysteinylation of peptides was performed by treating 1 mM peptide with 2 mM 1,4-Dithiothreitol in 50 mM ammonium bicarbonate for 15 min. at 50° C., followed by addition of 10 mM free cysteine and 15 mM $H_2O_2$ for 30 min. at RT. pMHC tetramers were produced as outlined previously (7, 8). In brief, monomers consisting of recombinant HLA-A*02:01 heavy chain and human β2-microglobulin were purified by gel-filtration HPLC and biotinylated. After folding with the appropriate peptide, pMHC tetramers were generated by adding PE-conjugated streptavidin (Invitrogen, Thermo Fisher Scientific). UV-exchange pMHC tetramers were produced by exposing biotinylated HLA-A*02:01 monomers containing UV-sensitive peptide to 366 nm UV light in the presence of cysteinylated ΔNPM1 peptide. After 1 hour of peptide exchange, monomers were incubated for 1 hour at 4° C. followed by centrifugation at 4000 g for 10 min. at 15° C. Tetramers were produced by adding streptavidin-conjugated PE to supernatants. pMHC tetramers were stored at 4° C.

Antibodies and FACS Analysis

T cells were stained with FITC-conjugated antibodies against CD3, CD4, CD8 (BD Biosciences, San Jose, Calif., United States) and TCR-Vβ5.1 (Beckman Coulter, Brea, Calif., United States), APC-conjugated antibodies against CD3, CD4, CD8 and mouse TCR-Cβ and PE-conjugated pMHC tetramers and antibodies against CD3, CD4 and CD8 (BD Biosciences). Cells were measured on a BD FACSCalibur II (BD Biosciences) using BD CellQuest Pro software (BD Biosciences) and analysis was performed with FlowJo software (Flowjo, LLC, Ashland, Oreg., United States).

T Cell Isolation and Culture pMHC tetramer positive CD8 T cells were isolated from PBMC from patients with AML and healthy individuals as previously described (9). In short, PBMC from HLA*02:01 positive AML patients and healthy individuals were stained with PE-conjugated pMHC tetramers containing ΔNPM1 peptides for 1 hour at 4° C. followed by MACS isolation using anti-PE MicroBeads (Miltenyi Biotec). Isolated cells were stained with CD8-Alexa Fluor 700 (Invitrogen), CD4-FITC, CD14-FITC and CD19-FITC (BD Biosciences) antibodies and pMHC tetramer positive CD8 T cells were single cell sorted by a BD FACSAria III cell sorter (BD Biosciences) using BD FACSDiva v6 software (BD Biosciences). Single T cells were stimulated with 50,000 irradiated allogeneic PBMC, 5000 irradiated allogeneic EBV-LCL and 0.8 µg/ml PHA (Oxoid Microbiology Products, Thermo Fisher Scientific) in 100 µl TCM per well in 96-wells U-bottom culture plates (Costar, Sigma-Aldrich). Growing T cell clones were restimulated every 10-14 days with irradiated feeder cells and PHA.

T Cell Reactivity Assays

T cell recognition was measured by IFN-γ ELISA (Sanquin). Stimulator cells (30,000 cells) were co-incubated with T cells (2000 cells) in 40 μl TCM per well in 384-wells flat-bottom plates (Greiner Bio One, Kremsmünster, Austria). After overnight co-incubation, culture supernatants were harvested to measure IFN-γ release. In peptide recognition assays, T2 cells (15,000 cells) were pre-incubated for 30 min. at 37° C. with titrated peptide concentrations and washed twice before co-incubation with T cells. In blocking assays, target cells (10,000 cells) were pre-incubated for 60 min. at RT with saturating concentrations of antibodies blocking HLA class I (W6/32) or HLA class II (PdV5.2) before addition of T cells. T cell mediated cytotoxicity was measured in $^{51}$chromium release assays. Primary AML cells were labelled with 100 μCi Na$_2$$^{51}$CrO$_4$ for 1 hour at 37° C., washed and co-incubated with T cells at various E:T ratios in 100 μl TCM per well in 96-wells U-bottom culture plates (Costar). Spontaneous and maximum $^{51}$Cr release were measured in separate plates containing 100 μl TCM or 100 μl TCM with 1% Triton-X100 per well (Sigma-Aldrich), respectively. After 9 hrs of co-incubation, 25 μl culture supernatants were harvested and transferred to 96-wells LumaPlates (PerkinElmer, Waltham, Mass., United States). $^{51}$Cr release in counts per minute (cpm) was measured on a 2450 Microbeta$^2$ plate counter (PerkinElmer).

TCR Cloning and Production of Retroviral Supernatants

TCR α and β chain usage of clone 1A2 was determined as previously described (9) with minor modifications. In brief, T cells were lysed and mRNA was isolated by the Dynabeads mRNA DIRECT kit (Invitrogen). TCR-specific cDNA was generated using two TCR-Cβ specific primers, a TCR-Cα specific primer, a SA.rt anchor template-switching oligonucleotide (TSO) and SMARTScribe Reverse Transcriptase (Takara, Clontech, Mountain View, Calif., United States). During first strand cDNA synthesis, SMARTScribe reverse transcriptase adds a 3' non-templated polycytosine terminus, which allows for annealing of the TSO and 2$^{nd}$ strand cDNA synthesis. TCR amplification was performed by PCR using Phusion Flash (Thermo Fisher Scientific), an anchor-specific primer and nested primers annealing to TCR-Cα or -Cβ regions. TCR sequences for clone 1A2 were identified as TRAV12-2 and TRBV5-1 by Sanger sequencing (Macrogen, Amsterdam, the Netherlands) and the ImMunoGeneTics (IMGT) database (10). Codon-optimized TRAV12-2 and TRBV5-1 sequences were synthesized and cloned in the MP71-TCR-flex retroviral vector (11) by GenScript (Piscataway, N.J., United States). In MP71-TCR-flex, murine TCR-Cα and -Cβ regions contain additional cysteine residues to promote preferential pairing and expression of the TCR, linked by a porcine teschovirus-derived P2A sequence. The construct was transfected into packaging cells φ-NX-A (ATCC, Manassas, Va., United States) and retroviral supernatants 48 and 72 hrs after transfection were harvested and frozen at −80° C. MP71-TCR-flex encoding the TCR for the CMV-derived HLA-A*02:01-restricted peptide NLVPMVATV (SEQ ID NO:31) was kindly provided by Prof. Dr. T. N. Schumacher (Division of Immunology, Netherlands Cancer Institute, Amsterdam, the Netherlands).

TCR Gene Transfer

PBMC from two HLA-A*02:01 positive healthy individuals (donor 1 and 2) were thawed and CD4 and CD8 cells were isolated by MACS using anti-CD4 MicroBeads (Miltenyi Biotec) followed by the CD8 T Cell Isolation Kit (Miltenyi Biotec). CD8 and CD4 cells were stimulated with irradiated autologous feeders and 0.8 μg/ml PHA in 24-wells flat bottom culture plates (Costar). Two days after stimulation, T cells were transferred to 24-wells flat bottom suspension culture plates (Greiner Bio-One) for retroviral transduction as described previously (9, 12). Prior to addition of T cells, the plates were coated with 30 mg/mL retronectin (Takara, Clontech) and blocked with 2% human serum albumin (Sanquin).

Retroviral supernatants were added and plates were centrifuged at 3000 g for 20 min. at 4° C. T cells were added to the plates with viral supernatants at 300,000 cells per well. After overnight incubation, T cells were transferred to 24-wells flat bottom culture plates. At day 6 after transduction, TCR-transduced T cells were stained with an APC-conjugated antibody against mouse TCR-Cβ for 15 min. at 4° C. followed by MACS isolation using anti-APC MicroBeads (Miltenyi Biotec). TCR-transduced T cells were re-stimulated every 10-14 days with irradiated allogeneic PBMC and EBV-LCL and 0.8 μg/ml PHA. Prior to analysis, re-stimulated TCR-transduced T cells were enriched by MACS using anti-mouse TCR-CR-APC and anti-APC MicroBeads as described above.

Results

Presence of ΔNPM1 in the HLA Class I Ligandome of Primary AML

To investigate whether ΔNPM1 peptides are processed and presented in HLA class I, the inventors immunoprecipitated HLA class I surface molecules from 12 primary AML samples, eluted the peptides from the binding groove and analyzed the peptidome by mass spectrometry. Table I shows the HLA class I typing of the 12 AML samples as well as their mutational status for NPM1. The 4-bp frameshift insertion in exon 12 of the NPM1 gene is a recurrent mutation that occurs in 30% of primary AML. In 8 out of 12 primary AML, the presence of ΔNPM1 was demonstrated by PCR fragment analysis. All patients had normal karyotypes by cytogenetics with the exception of one AML, which carried the known chromosomal rearrangement inv(16) (p13q22). Blast percentages as measured in the peripheral blood or bone marrow samples ranged between 55-98%.

TABLE 1

Presence of ΔNPM1 in the HLA class I-ligandome of primary AML

| Patient | HLA class I | ΔNPM1[a] | Karyotype | Blasts (%)[b] | Eluted peptide | # Spectra |
|---|---|---|---|---|---|---|
| AML10197 | A*01:01 | + | 46, XX | 98% | CLAVEEVSL | 11,232 |
|  | A*02:01 |  |  |  |  |  |
|  | B*08:01 |  |  |  |  |  |
|  | B*44:03 |  |  |  |  |  |
|  | C*07:01 |  |  |  |  |  |
|  | C*16:01 |  |  |  |  |  |

TABLE 1-continued

Presence of ΔNPM1 in the HLA class I-ligandome of primary AML

| Patient | HLA class I | ΔNPM1[a] | Karyotype | Blasts (%)[b] | Eluted peptide | # Spectra |
|---|---|---|---|---|---|---|
| AML3361 | A*02:01 A*11 B*13 B*35 C*04 C*06 | + | 46, XX | 79% | CLAVEEVSL AVEEVSLRK VEEVSLRK | 7,992 |
| AML6395 | A*02:01 A*24:03 B*38:01 B*51:01 C*02:02 C*12:03 | + | 46, XY | 80% | — | 3,915* |
| AML9448 | A*03:01 A*32:01 B*07:02 B*08:01 C*07:01 C*07:10 | + | 46, XX | 77% | CLAVEEVSLRK AVEEVSLRK | 10,352 |
| AML5444 | A*03:01 B*07:02 B*35:01 C*04:01 C*07:02 | + | 46, XX | 55% | AVEEVSLRK | 6,209 |
| AML5518 | A*01:01 A*24:02 B*35:03 B*44:03 C*04:01 C*16:01 | + | 46, XX | 95% | AVEEVSLRK AVEEVSLR | 8,479 |
| AML6498 | A*11:01 A*68:01 B*35:01 B*35:03 C*04:01 | + | 46, XX | 94% | CLAVEEVSLRK AVEEVSLRK | 12,233 |
| AML4443 | A*01:01 B*08:01 C*07:01 | + | 46, XX | 82% | AVEEVSLRK | 4,037 |
| AML1775 | A*24 A*02:01 B*51 B*40:01 C*10 C*03 | − | 46, XY, inv(16)(p13 q22) | 89% | — | 524* |
| AML2250 | A*02:01 A*01:01 B*62 B*15:01 C*10 C*03 | − | 46, XY | 95% | — | 4,286* |
| AML1143 | A*02:01 A*03:01 B*07:02 B*35:01 C*04:01 C*07:02 | − | 46, XY | 90% | — | 5,571 |
| AML3009 | A*11 A*02:01 B*15:01 B*07:02 C*03 C*07 | − | 46, XY | 70% | — | 4,466* |

[a]ΔNPM1 patients harbour a 4-bp insertion in exon 12 of the NPM1 gene causing a frameshift at the C-terminus of the protein.
[b]Blast percentages as measured in peripheral blood and bone marrow samples from patients with AML.
*AML samples for which peptide elution was performed using the anti-HLA-A*02:01 antibody BB7.2.

The recurrent 4-bp insertion in exon 12 results in a ΔNPM1 protein which is 4 AA longer than its wild type counterpart with 11 AA (CLAVEEVSLRK (SEQ ID NO: 27)) at the C-terminus translated in an alternative reading frame. From this alternative ΔNPM1 protein, a protein region spanning 10 N-terminal residues in the normal reading frame followed by the 11 C-terminal AA in the alternative reading frame (MTDQEAIQDLCLAVEEVSLRK (SEQ ID NO:34)) was searched for matching peptides in the HLA class I ligandomes as analyzed from the 12 primary AML. This revealed the presence of two 8-mer peptides (VEEVSLRK (SEQ ID NO:28) and AVEEVSLR), two 9-mer peptides (CLAVEEVSL (SEQ ID NO:1) and AVEEVSLRK (SEQ ID NO:26)) and one 11-mer peptide (CLAVEEVSLRK (SEQ ID NO: 27)) in AML with ΔNPM1, but not in AML with wtNPM1 (Table 1). All 5 ligands as eluted from 7 primary AML were validated with synthetic peptides by mass spectrometry (FIGS. 1 and 2). Validation of the tandem mass spectra of CLAVEEVSL (SEQ ID NO:1) and CLAVEEVSLRK (SEQ ID NO: 27) with synthetic peptides was performed upon cysteinylation of the first residue in vitro. Prediction of HLA class I binding affinity by NetMHCpan 3.0 suggested binding of the epitope CLAVEEVSL (SEQ ID NO:1) to HLA-A*02:01, whereas the epitopes AVEEVSLRK (SEQ ID NO:26) and CLAVEEVSLRK (SEQ ID NO: 27) were most likely to bind HLA-A*03:01 as well as HLA-A*11:01 and possibly HLA-A*01:01 for AVEEVSLRK (SEQ ID NO:26) (Table 2). Binding of CLAVEEVSL (SEQ ID NO:1) to HLA-A*02:01 as well as binding of AVEEVSLRK (SEQ ID NO:26) and CLAVEEVSLRK (SEQ ID NO: 27) to HLA-A*03:01 and A*11:01 was confirmed by monomer refolding. Since HLA-A*02:01 is expressed in 50% of the Caucasian population, the inventors focused their research on CLAVEEVSL (SEQ ID NO:1), which was detected in 2 out of 3 HLA-A*02:01 positive AML with ΔNPM1 (AML10197 and AML3361).

TABLE 2

Peptide binding affinity to HLA class I alleles as predicted by NetMHCpan3.0.

| | Predicted HLA class I binding affinity (nM) | | | | |
|---|---|---|---|---|---|
| Peptide | HLA-A*01:01 | HLA-A*02:01 | HLA-A*03:01 | HLA-A*11:01 | Other HLA class I alleles[a] |
| CLAVEEVSL | 27798.0 | 592.2 | N.A. | 33678.3 | ≥3562.6 |
| AVEEVSLRK | 16147.9 | 36154.8 | 534.4 | 58.2 | ≥1755.9 |
| CLAVEEVSLRK | N.A. | N.A. | 498.2 | 1111.8 | ≥5404.5 |
| AVEEVSLR | 31753.2 | N.A. | N.A. | N.A. | ≥39787.9 |
| VEEVSLRK | N.A. | 44597.1 | N.A. | 15474.5 | ≥38325.9 |

[a]Lower limit of predicted binding affinity (nM) for all other HLA class I alleles that are expressed by primary AML samples from which the peptide is eluted.
N.A. Not applicable.

T Cell Recognition of ΔNPM1 on Primary AML

To examine whether the HLA-A*02:01-restricted epitope CLAVEEVSL (SEQ ID NO:1) is a neoantigen that can be targeted by immunotherapy, the inventors searched for specific T-cells in patients with AML. PE-conjugated pMHC tetramers were produced for CLAVEEVSL (SEQ ID NO:1) (ΔNPM1-CLA) and its cysteinylated variant C*LAVEEVSL (cysteinylated form of SEQ ID NO:1) (ΔNPM1-C*LA) and a mix of these tetramers was used to isolate specific T cells from PBMC from 6 HLA-A*02:01 positive patients with ΔNPM1 AML who were in remission after chemotherapy. T cells binding to one or both pMHC tetramers were enriched by magnetic anti-PE beads and single tetramer positive CD8 cells were isolated by flow cytometry (Table 3).

TABLE 3

T cell isolations from patients with HLA-A*02:01 positive ΔNPM1 AML.

| Patient | Days after diagnosis[a] | PBM[b] (*10^6) | Sorted T cells[c] | Growing clones | Tetramer+ clones[d] |
|---|---|---|---|---|---|
| AML10833 | 89 | 10 | 21 | 1 | 0 |
| AML9559 | 107 | 8 | 2 | 2 | 0 |
| AML6395 | 69 | 13 | 6 | 2 | 0 |
| AML11282 | 86 | 11 | 12 | 0 | — |
| AML9423 | 3751 | 7 | 0 | — | — |
| AML10418 | 108 | 8 | 0 | — | — |

[a]Number of days after diagnosis.
[b]PBMC, peripheral blood mononuclear cells. Indicated are the numbers of PBMC from HLA-A*02:01 positive patients with ΔNPM1 AML that are used for T cell isolation.
[c]PBMC were stained with anti-CD8-ALX700 and a mix of PE-conjugated pMHC tetramers for CLAVEEVSL and its cysteinylated variant C*LAVEEVSL. Indicated are the numbers of tetramer positive CD8 cells that are sorted.
[d]Number of T cell clones that are positive for ΔNPM1-CLA or ΔNPM1-C*LA tetramers.

A total number of 41 tetramer positive CD8 cells were isolated from 42*10^6 PBMC from 4 patients, of which 5 T cells from 3 patients clonally expanded. None of the 5 T cell clones, however, could be stained with either the ΔNPM1-CLA tetramer or the ΔNPM1-C*LA tetramer, demonstrating that T cells for CLAVEEVSL (SEQ ID NO:1) do not exist or that frequencies are below the threshold of detection. Therefore, the same strategy was followed to search for specific T cells in large numbers of PBMC from 6 HLA-A*02:01 positive healthy individuals (Table 4). A variable number of 8-55 tetramer positive CD8 cells were isolated from 460-1970×10^6 total PBMC from each healthy individual. Of these cells, 31 T cells from 5 individuals clonally expanded and 13 T cell clones from 4 individuals were positive for the ΔNPM1-CLA tetramer. Of these 13 clones, 3 T cell clones could also be stained with the ΔNPM1-C*LA tetramer (Table 4 and FIG. 3A).

TABLE 4

T cell isolation for ΔNPM1 from healthy individuals

| Donor | PBMC[a] (*10^6) | Tetramer+ CD8 T cells[b] | Growing clones | ΔNPM1-CLA tetramer+[c] | ΔNPM1-C*LA tetramer+[d] | Reactive clones |
|---|---|---|---|---|---|---|
| 1 | 460 | 14 | 4 | 2 | 1 | 1 |
| 2 | 700 | 8 | 6 | 4 | n.d. | 0 |
| 3 | 970 | 20 | 7 | 3 | 0 | 0 |
| 4 | 560 | 24 | 8 | 0 | 0 | — |
| 5 | 545 | 13 | 0 | — | — | — |
| 6 | 1970 | 55 | 6 | 4 | 2 | 1 |

[a]PBMC, peripheral blood mononuclear cells. Indicated are the numbers of PBMC from HLA-A*02:01 positive healthy individuals that are used for T cell isolation.
[b]PBMC were stained with anti-CD8-ALX700 and a mix of PE-conjugated pMHC tetramers for CLAVEEVSL and its cysteinylated variant C*LAVEEVSL. Indicated are the numbers of tetramer positive CD8 cells that are sorted.
[c]Number of growing T cell clones positive for ΔNPM1-CLA tetramer.
[d]Number of growing T cell clones positive for ΔNPM1-C*LA tetramer.
n.d. Not done.

Figure 3:
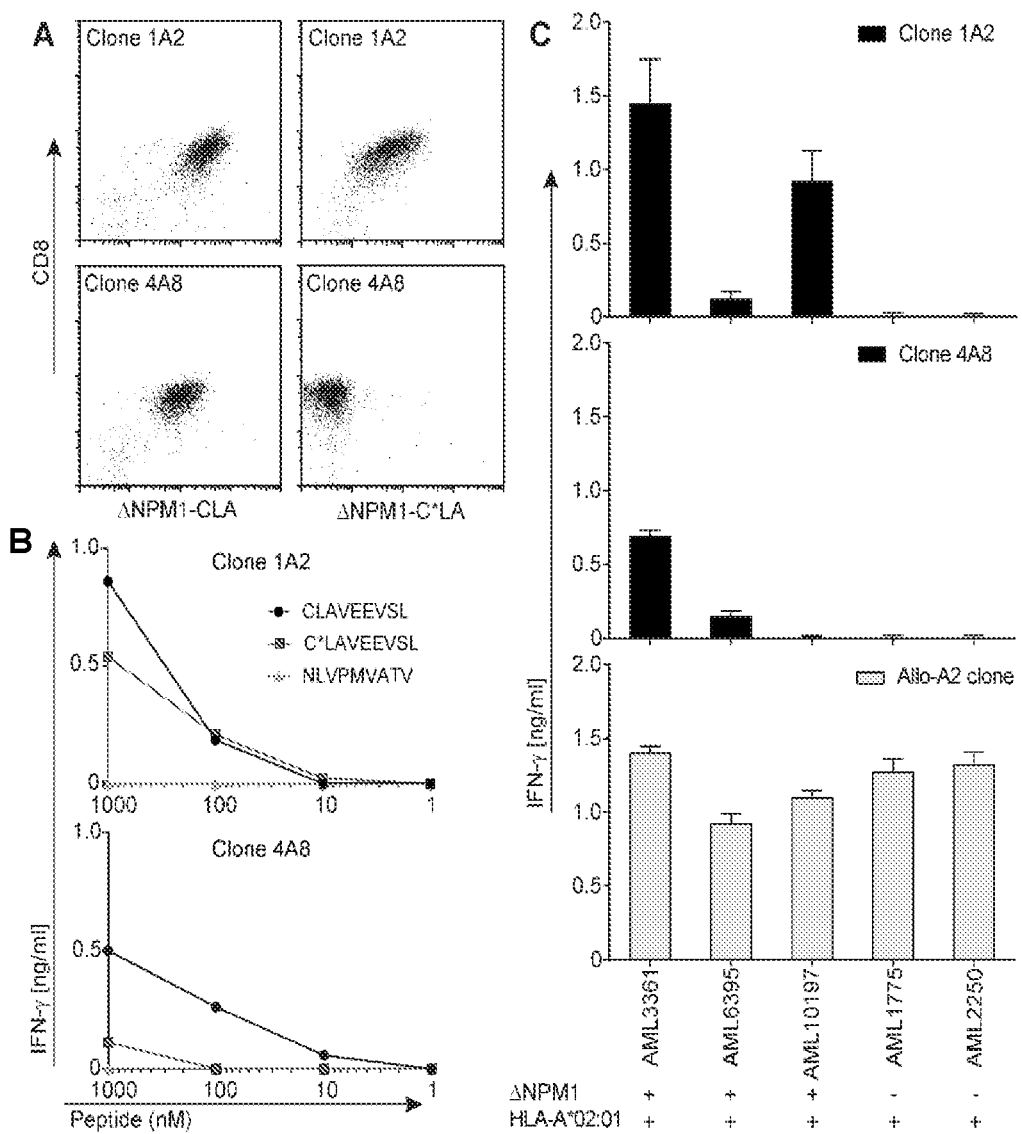
FIG. 3 shows that CD8 cells for ΔNPM1 were single cell isolated from PBMC from HLA-A*02:01 positive healthy individuals using a mix of ΔNPM1-CLA and ΔNPM1-C*LA pMHC tetramers. A. Growing T cell clones were tested for staining with pMHC tetramers. T cell clones 1A2 (top) and 4A8 (bottom) were both positive for the ΔNPM1-CLA tetramer, whereas only clone 1A2 stained with ΔNPM1-C*LA. B. Tetramer positive T cell clones 1A2 (top) and 4A8 (bottom) were tested for reactivity against HLA-A*02:01 positive T2 cells exogenously loaded with titrated concentrations of uncysteinylated ΔNPM1 peptide CLAVEEVSL (SEQ ID NO:1) (circles), cysteinylated ΔNPM1 peptide C*LAVEEVSL (SEQ ID NO:1 in cysteinylated form) (squares) or an irrelevant HLA-A*02:01-restricted CMV peptide NLVPMVATV (SEQ ID NO:31) (triangles) by IFN-γ ELISA. Only clone 1A2 showed recognition of both the cysteinylated and uncysteinylated ΔNPM1 peptide. No reactivity was seen against the irrelevant NLVPMVATV (SEQ ID NO:31) peptide. Mean release of IFN-γ (ng/ml) in duplicate wells is shown. C. Clones 1A2 (top) and 4A8 (middle) were tested for reactivity against 5 HLA-A*02:01 positive primary AML by IFN-γ ELISA. The panel included 3 AML with ΔNPM1 and 2 AML with wtNPM1. T cell clone 1A2 reacted against all 3 AML with ΔNPM1 to different extents, whereas clone 4A8 recognized only 2 out of 3 AML. Both T cell clones failed to recognize AML with wtNPM1. An HLA-A*02:01-specific allo-reactive T cell clone (Allo-A2 clone; bottom) was included as positive control. Mean release of IFN-γ (ng/ml) in duplicate wells is shown.

To determine whether the 13 tetramer positive CD8 clones were reactive against their target peptide, clones were tested for recognition of HLA-A*02:01 positive T2 cells exogenously loaded with CLAVEEVSL (SEQ ID NO:1), the cysteinylated variant C*LAVEEVSL (cysteinylated form of SEQ ID NO:1) or an irrelevant HLA-A*02:01-restricted CMV peptide NLVPMVATV (SEQ ID NO:31). Of the 13 ΔNPM1-CLA tetramer positive clones, 2 T cell clones (1A2 and 4A8) showed specific reactivity against T2 cells loaded with CLAVEEVSL (SEQ ID NO:1), but not the control peptide NLVPMVATV (SEQ ID NO:31) (FIG. 3B). Clone 1A2 also showed recognition of T2 cells loaded with C*LAVEEVSL (cysteinylated form of SEQ ID NO:1). These results are in line with tetramer data and demonstrate that cysteinylation of the first residue abolishes T cell recognition by clone 4A8. Peptide recognition by clone 1A2, however, is independent of cysteinylation as illustrated by its specific reactivity against CLAVEEVSL (SEQ ID NO:1) as well as C*LAVEEVSL (cysteinylated form of SEQ ID NO:1).

To investigate the anti-tumor potential of clone 1A2 and 4A8, T cell reactivity was measured against a panel of 5 HLA-A*02:01 positive primary AML including 3 samples with ΔNPM1 and 2 samples with wtNPM1. T cell clone 1A2 showed reactivity against all 3 AML with ΔNPM1 to different extents, whereas clone 4A8 showed relatively low reactivity against 2 of 3 samples with ΔNPM1 (FIG. 3C). Strong T cell reactivity against AML by clone 1A2 may be explained by its capacity to recognize cysteinylated ΔNPM1 as eluted from the cell surface of primary AML as well as uncysteinylated ΔNPM1. No T cell reactivity was observed against HLA-A*02:01 positive AML with wtNPM1 (FIG. 3C) or HLA-A*02:01 negative AML with ΔNPM1 (data not shown). These data indicate that T cells with a TCR specific for ΔNPM1 exist in the T cell repertoire of healthy individuals and that these T cells can specifically recognized CLAVEEVSL (SEQ ID NO:1) as endogenous neoantigen presented by HLA-A*02:01 on primary AML with ΔNPM1.

TCR Gene Transfer to Target ΔNPM1 on Primary AML

Figure 4:
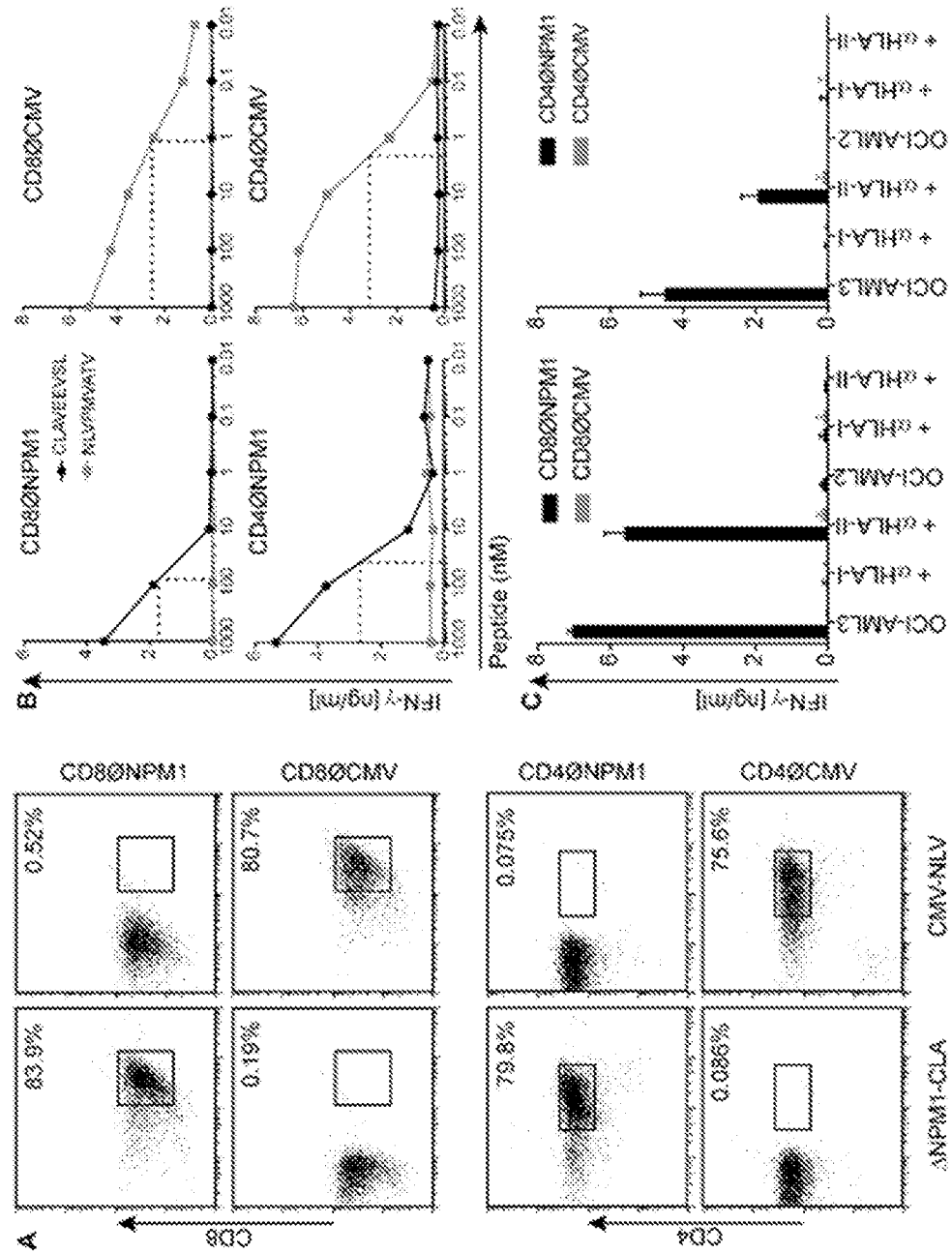
FIG. 4 shows specificity for ΔNPM1 after TCR gene transfer. The genes for the ΔNPM1-specific TCR α and β chains of clone 1A2 were cloned into a modified MP71-TCR-flex retroviral vector for TCR gene transfer. CD8 and CD4 cells isolated from HLA-A*02:01 positive healthy individuals were retrovirally transduced with the TCR for ΔNPM1 and, as a control, with the TCR for the HLA-A*02: 01-restricted CMV peptide NLVPMVATV (SEQ ID NO:31). At day 6 after transduction, TCR-transduced T cells were purified using an APC-conjugated antibody against mouse TCR-Cβ and magnetic anti-APC beads. A. TCR-transduced T cells were analyzed by flow cytometry at day 7 after transduction using antibodies against CD8 or CD4 and pMHC tetramers for CLAVEEVSL (SEQ ID NO:1) (ΔNPM1-CLA; left) or NLVPMVATV (SEQ ID NO:31) (CMV-NLV; right). CD8 (CD8ØNPM1) and CD4 (CD4ØNPM1) cells transduced with the TCR for ΔNPM1 stained with the ΔNPM1-CLA tetramer, but not with the CMV-NLV tetramer. In contrast, CD8 (CD8ØCMV) and CD4 (CD4ØCMV) T cells transduced with the CMV-specific TCR showed binding to the CMV-NLV tetramer, but not to the ΔNPM1-CLA tetramer. Results are shown for donor 1, but results were similar for donor 2. B. TCR-transduced T cells were analyzed for reactivity against their target peptides by IFN-γ ELISA. TCR-transduced CD8 and CD4 cells were co-incubated with T2 cells exogenously loaded with titrated concentrations of ΔNPM1 peptide CLAVEEVSL (SEQ ID NO:1) (circles) or CMV-derived peptide NLVPMVATV (SEQ ID NO:31) (squares). CD8ØNPM1 (upper left) and CD4ØNPM1 (lower left) showed half maximum recognition of T2 cells loaded with CLAVEEVSL (SEQ ID NO:1) at concentrations of 30-100 nM (dotted lines), but no recognition of T2 cells loaded with NLVPMVATV (SEQ ID NO:31). Conversely, CD8ØCMV (upper right) and CD4ØCMV (lower right) reacted against T2 cells loaded with NLVPMVATV (SEQ ID NO:31), but not with CLAVEEVSL (SEQ ID NO:1). Mean release of IFN-γ (ng/ml) in duplicate wells is shown for donor 1, but results were similar for donor 2. C. TCR-transduced T cells (CD8ØNPM1 and CD4ØNPM1 represented by black bars; CD8ØCMV and CD4ØCMV represented by grey bars) were tested for recognition of HLA-A*02:01 positive AML cell lines with ΔNPM1 (OCI-AML3) or wtNPM1 (OCI-AML2) in the absence or presence of blocking antibodies against HLA class I (W6/32) or HLA class II (PdV5.1) by IFN-γ ELISA. Recognition of OCI-AML3 by CD8 and CD4 cells transduced with the TCR for ΔNPM1 is mediated by HLA class I. Mean release of IFN-γ (ng/ml) in duplicate wells is shown for donor 2.

Since ΔNPM1 is a recurrent 4-bp insertion that occurs in 30% of primary AML and HLA-A*02:01 is expressed in 50% of the Caucasian population, the inventors consider CLAVEEVSL (SEQ ID NO:1) an ideal target for TCR gene transfer. Since primary AML were most strongly recognized by clone 1A2, mRNA was isolated from this clone and cDNA was generated to sequence the variable regions of the TCR α and β chains for ΔNPM1. Codon-optimized gene sequences for TRAV12-2 and TRBV5-1 as expressed by T cell clone 1A2 were synthesized and cloned into a modified MP71-TCR-flex retroviral vector. To facilitate preferential binding and expression of the TCR α and β chains, the variable regions of the TCR were cloned in-frame with murine constant regions linked by a P2A sequence. The TCR for ΔNPM1 and, as a control, the TCR for the HLA-A*02:01-restricted CMV peptide NLVPMVATV (SEQ ID NO:31) were introduced into CD8 and CD4 cells that were isolated from PBMC from healthy HLA-A*02:01 positive individuals (donor 1 and 2). At day 6 after transduction, TCR-transduced CD8 and CD4 cells were purified using an APC-conjugated antibody against mouse TCR-Cβ and magnetic anti-APC beads. Flow cytometric analysis demonstrated specific binding of the ΔNPM1-CLA tetramer to CD8 cells transduced with the TCR for ΔNPM1 (CD8ØNPM1) (FIG. 4A). In contrast, the CMV-NLV tetramer did not bind to CD8 cells transduced with the TCR for ΔNPM1, whereas CD8 cells transduced with the CMV-specific TCR (CD8ØCMV) could be stained with the CMV-NLV tetramer, but not with the ΔNPM1-CLA tetramer. For TCR-transduced CD4 cells (CD4ØNPM1 and CD4ØCMV), results were similar as for CD8 cells, indicating that binding of the ΔNPM1-CLA tetramer to TCR-transduced T cells occurs independent of the CD8 co-receptor. TCR-transduced CD8 and CD4 cells could also be stained with an antibody against mouse TCR-Cβ and CD8 and CD4 cells transduced with the TCR for ΔNPM1 also showed specific binding to an antibody against human TCR-Vβ5.1 (data not shown).

The inventors then analyzed the functionality of CD8 and CD4 cells transduced with the TCR for ΔNPM1 and demonstrated specific release of IFN-γ upon co-incubation with HLA-A*02:01 positive T2 cells loaded with CLAVEEVSL (SEQ ID NO:1), but not upon co-incubation with the CMV peptide NLVPMVATV (SEQ ID NO:31) (FIG. 4B). Specific release of IFN-γ was also observed upon co-incubation with AML cell line OCI-AML3 with ΔNPM1, but not upon stimulation with AML cell line OCI-AML2 with wtNPM1 (FIG. 4C).

Figure 5:
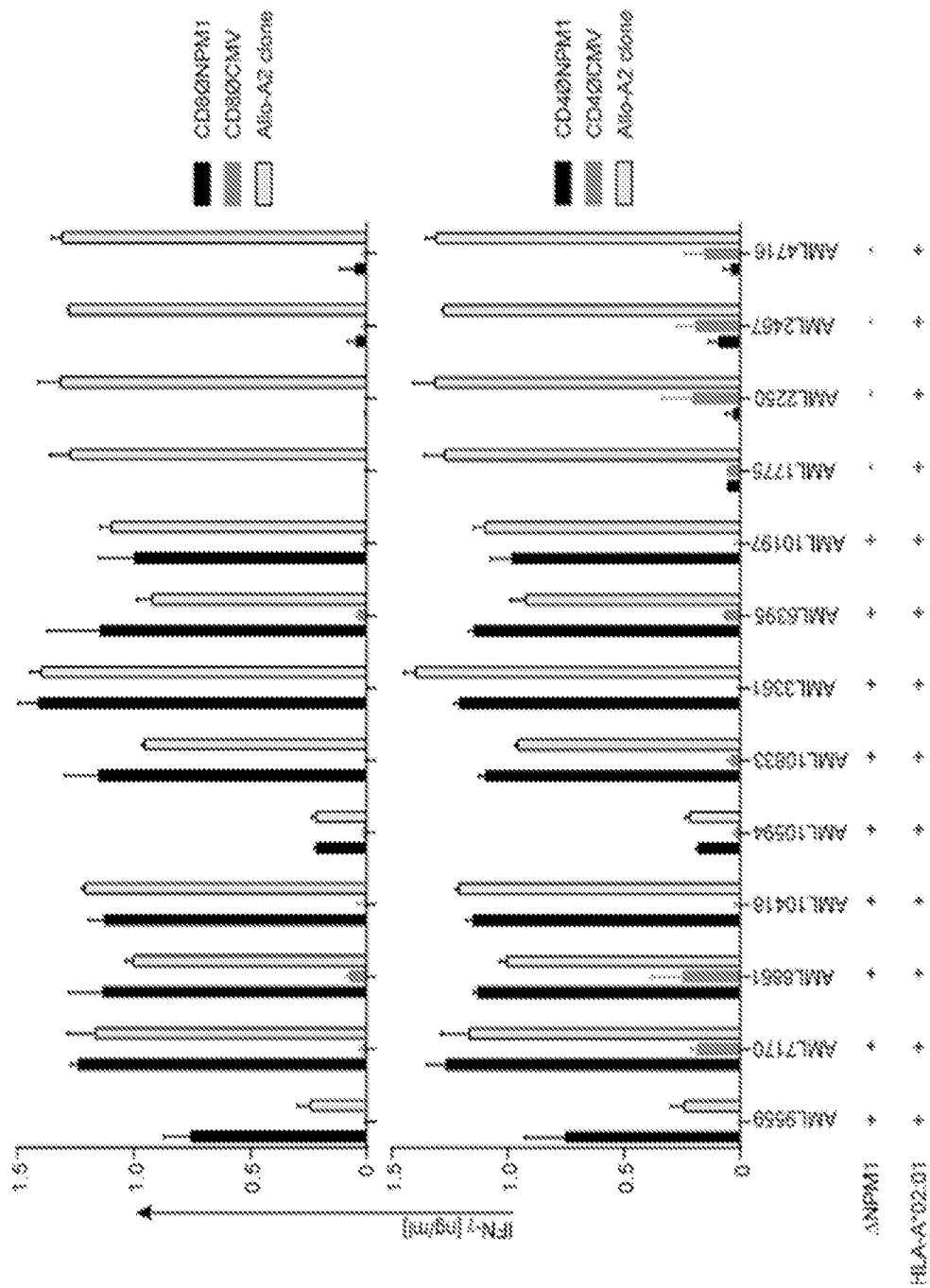
FIG. 5 shows recognition of ΔNPM1 on primary AML after TCR gene transfer. TCR-transduced CD8 and CD4 cells were tested for reactivity against a panel of 13 HLA-A*02:01 positive primary AML including 9 samples with ΔNPM1 and 4 samples with wtNPM1 by IFN-γ ELISA. CD8 (CD8ØNPM1; top panel; black bars) and CD4 (CD4ØNPM1; bottom panel; black bars) cells transduced with the TCR for ΔNPM1 reacted against all 9 AML with ΔNPM1, but not against AML with wtNPM1, whereas none of the 13 AML samples were specifically recognized by CD8 (CD8ØCMV; top panel; dark grey bars) or CD4 (CD4ØCMV; bottom panel; dark grey bars) cells after transfer of the CMV-specific TCR. TCR-transduced CD8 and CD4 cells also failed to recognize HLA-A*02:01 negative AML with ΔNPM1 (data not shown). The allo-A2 clone (light grey bars) is included as positive control. Mean release of IFN-γ (ng/ml) in duplicate wells is shown for donor 1.
Figure 6:
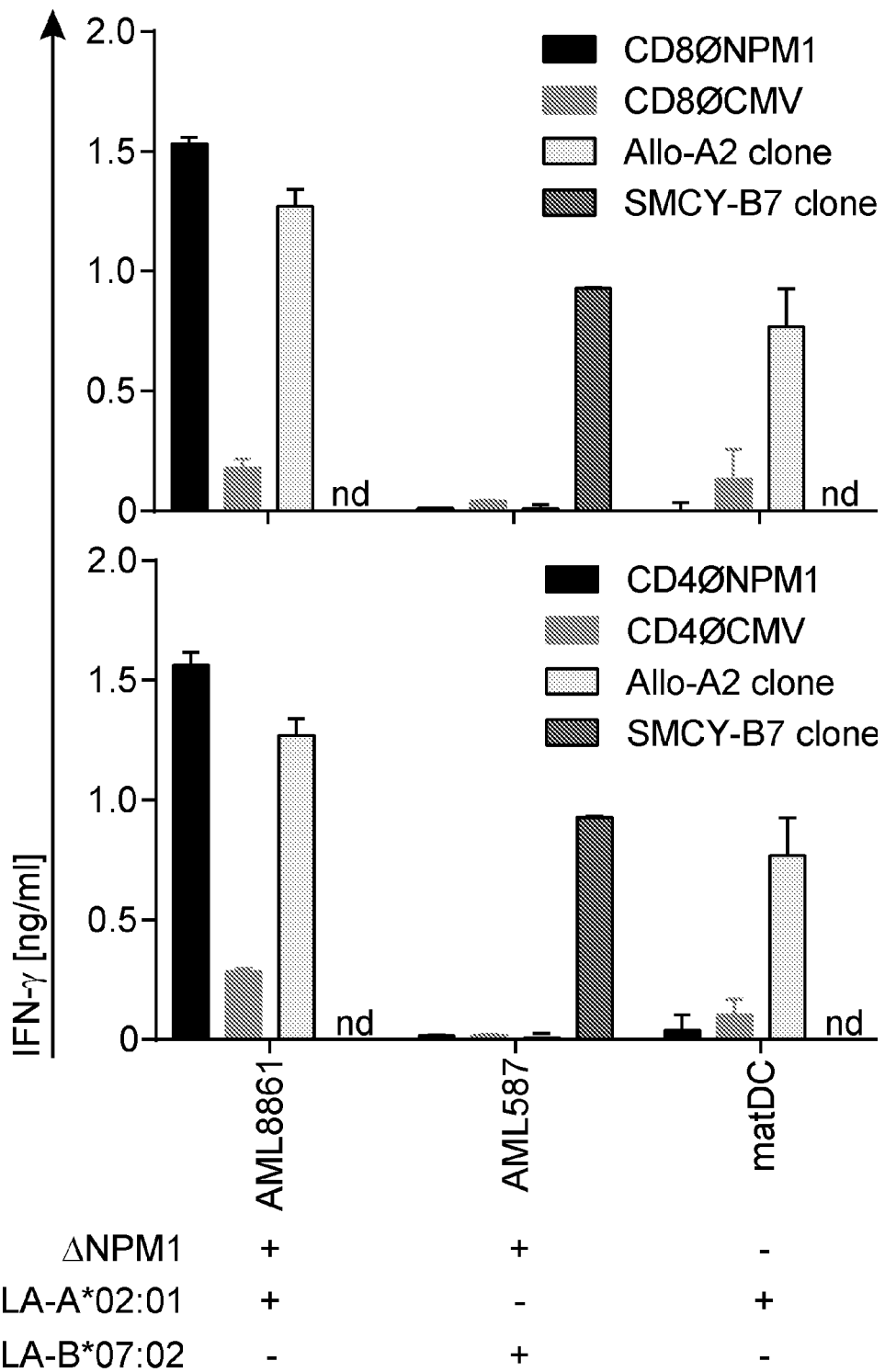
FIG. 6 shows TCR-transduced T cells tested on monocyte-derived mature DC by IFN-γ ELISA. T cells from donor 2 transduced with the TCR for ΔNPM1 (CD8ØNPM1 and CD4ØNPM1; black bars) or CMV (CD8ØCMV and CD4ØCMV; middle grey bars) were tested for reactivity against autologous monocyte-derived mature DC as well as ΔNPM1 positive AML that were HLA-A*02:01 positive (AML8861) or negative (AML587). For the autologous mature DC and AML8861, the allo-A2 clone (light grey bars) was included as positive control, whereas AML587 was loaded with an HLA-B*07:02 binding SMCY peptide and tested for recognition by an SMCY-specific CD8 T cell clone as positive control (dark grey bars). Mean release of IFN-γ (ng/ml) in duplicate wells is shown.

TCR-transduced CD8 and CD4 cells were subsequently tested for reactivity against a panel of 13 HLA-A*02:01 positive primary AML including 9 samples with ΔNPM1 and 4 samples with wtNPM1. Upon transduction with the TCR for ΔNPM1, CD8 and CD4 cells both showed recognition of all 9 primary AML with ΔNPM1, whereas no specific recognition of AML with wtNPM1 was observed (FIG. 5). CD8 and CD4 cells transduced with the TCR for ΔNPM1 also lacked reactivity against HLA-A*02:01 negative AML with ΔNPM1 and mature DC with wtNPM1 (FIG. 6). Next, transduced T cells were tested for reactivity against monocyte-derived mature DC from donor 1 and 2 and a panel of 40 HLA-A*02:01 positive third-party EBV-LCL as non-malignant cell types with strong antigen processing and presentation capacity. CD8 and CD4 cells transduced with the TCR for ΔNPM1 failed to recognize mature DC or EBV-LCL, indicating that alternative translation of the wtNPM1 gene does not occur and that this gene does not produce a peptide resembling CLAVEEVSL (SEQ ID NO:1). In summary, the data show that the TCR for ΔNPM1 upon gene transfer to CD8 and CD4 cells results in specific recognition of CLAVEEVSL (SEQ ID NO:1) as endogenous neoantigen presented by HLA-A*02:01 on primary AML with ΔNPM1.

Figure 7:
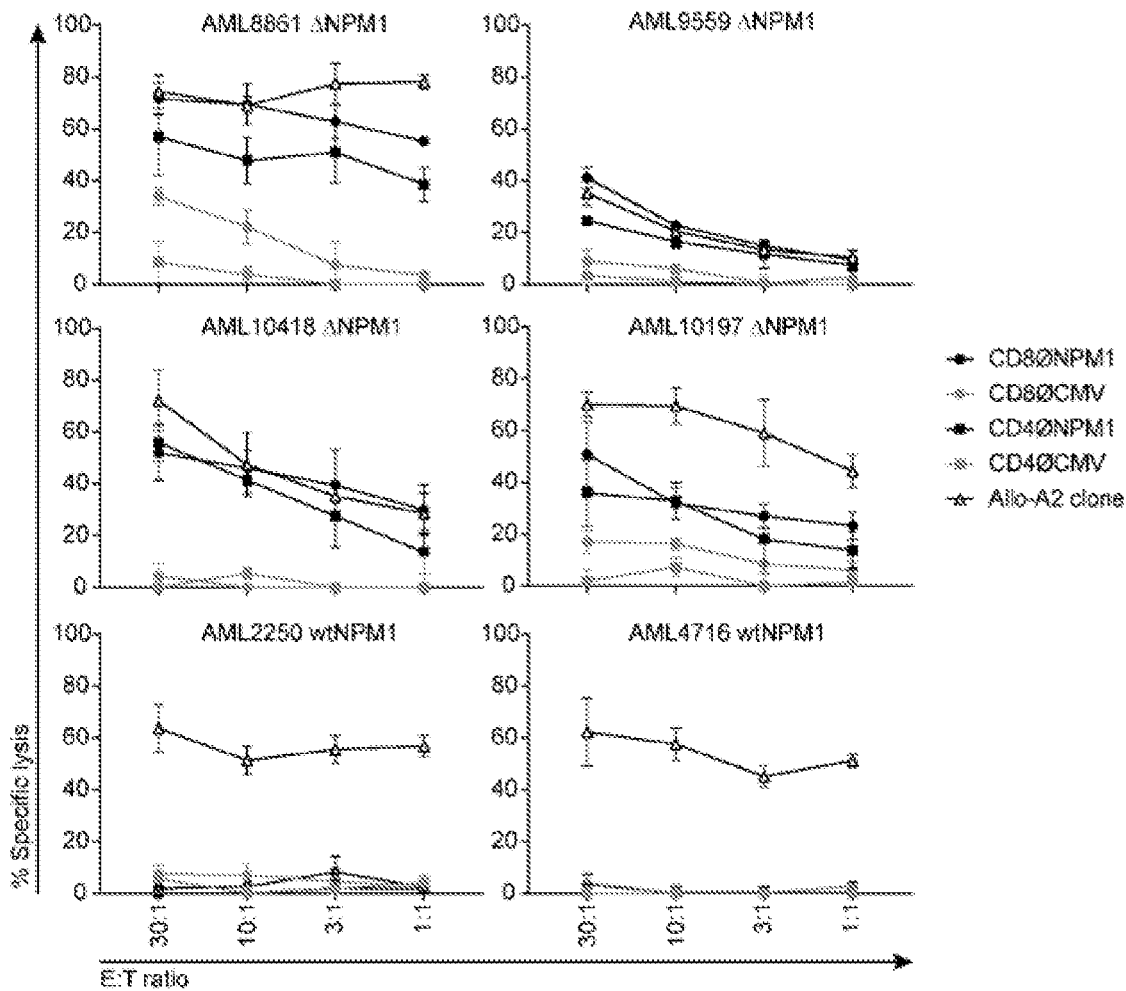
FIG. 7 shows lysis of primary AML with ΔNPM1 after TCR gene transfer in $^{51}$Cr release assays. TCR-transduced CD8 and CD4 cells were tested for cytolytic capacity by 9 hrs $^{51}$Cr-release assay on a panel of 6 HLA-A*02:01 positive primary AML including 4 samples with ΔNPM1 and 2 samples with wtNPM1. CD8 (CD8ØNPM1; black circles) and CD4 (CD4ØNPM1; black squares) cells transduced with the TCR for ΔNPM1 showed specific lysis of all 4 AML with ΔNPM1, but not of AML with wtNPM1, whereas none of the 6 AML samples were specifically lysed by CD8 (CD8ØCMV; grey circles) or CD4 (CD4ØCMV; bottom panel; grey squares) cells after transfer of the CMV-specific TCR. The allo-A2 clone (grey triangles) is included as positive control. Mean percentage of specific lysis in triplicate wells is shown at an E:T ratio of 30:1 for donor 2, but results were similar for donor 1.
Figure 37:
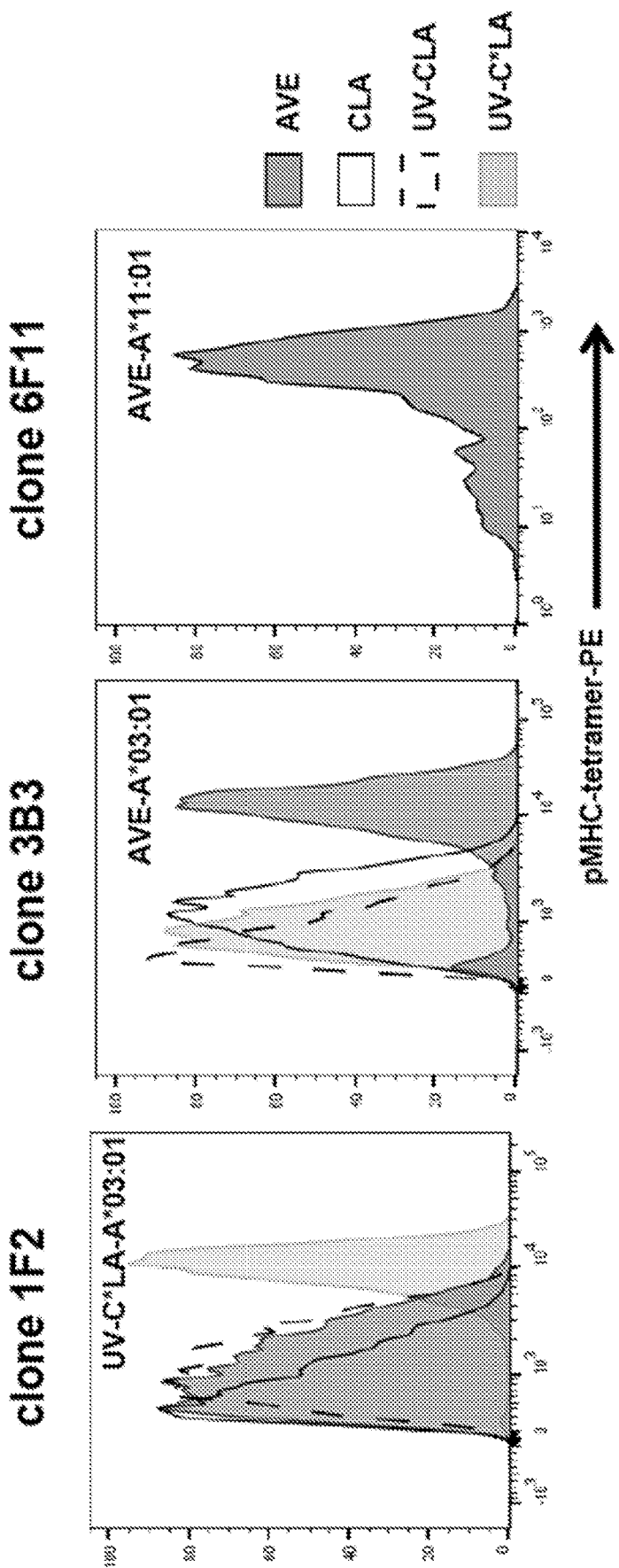
FIGS. 37 to 39 show T cells for ΔNPM1 peptides in A*03;01 and A*11:01. A mix of PE-conjugated HLA-A*03:01 tetramers with ΔNPM1 peptides AVEEVSLRK (SEQ ID NO:26) (AVE), CLAVEEVSLRK (SEQ ID NO:27) (CLA) and C*LAVEEVSLRK (SEQ ID NO:27 in cysteinylated form) (C*LA; first residue cysteinylated) or a single HLA-A*11:01 tetramer with AVEEVSLRK (SEQ ID NO:26) were used to isolate specific T-cells from HLA-A*03:01 and/or HLA-A*11:01 positive healthy individuals, respectively. The HLA-A*03:01 tetramer with C*LAVEEVSLRK (SEQ ID NO:27 in cysteinylated form) and, as a control CLAVEEVSLRK (SEQ ID NO: 27), were produced by UV exchange (UV-C*LA and UV-CLA, respectively).
Figure 38:
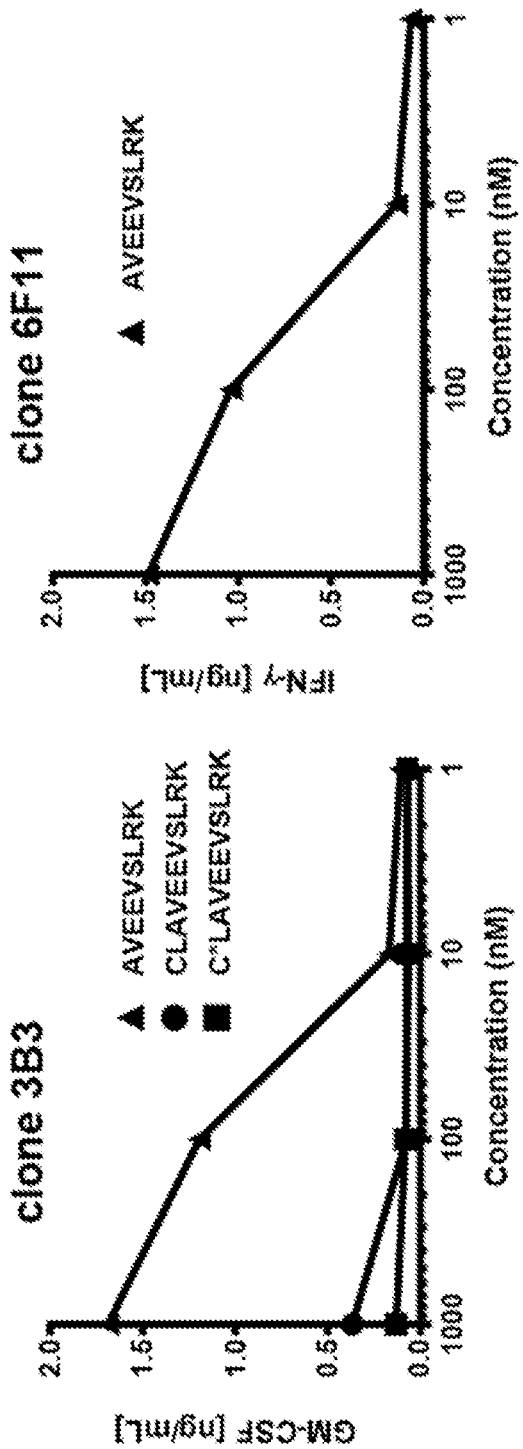
Figure 39:
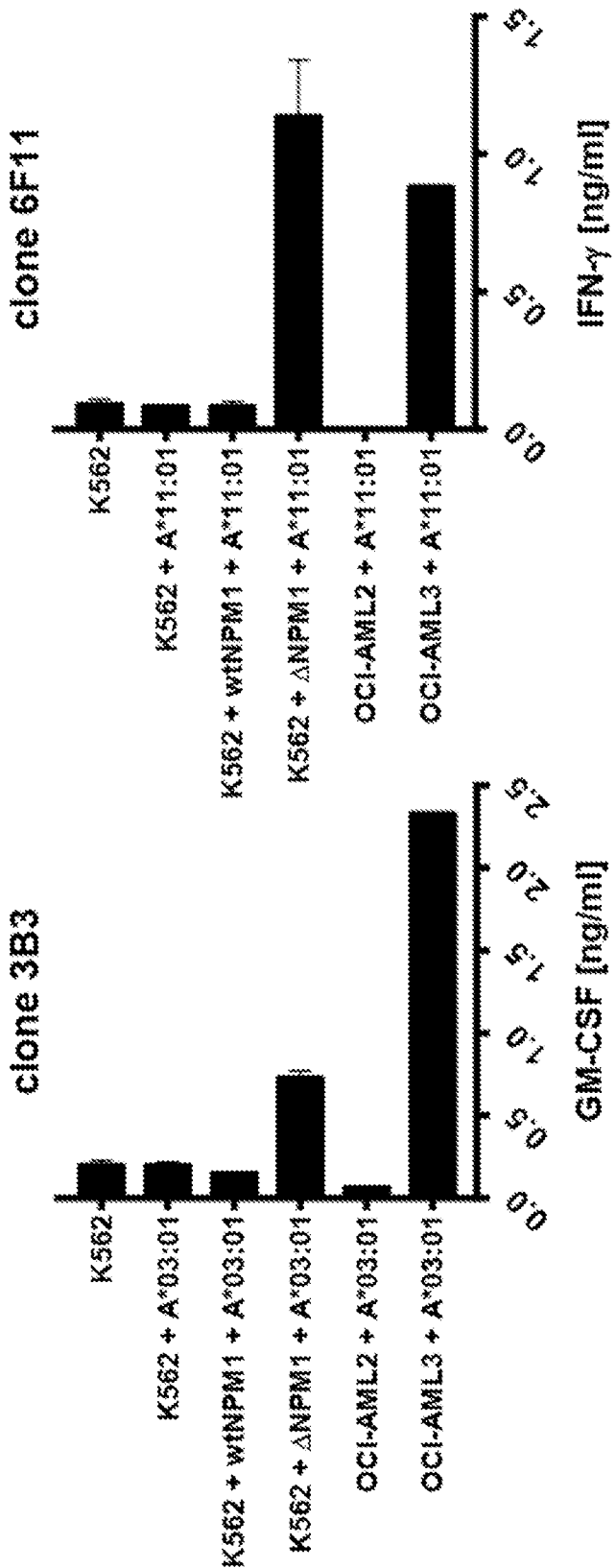

Finally, the inventors tested the cytolytic capacity of TCR-transduced CD8 and CD4 cells against primary AML. TCR-transduced T cells were tested against a panel of 6 HLA-A*02:01 positive primary AML including 4 samples with ΔNPM1 and 2 samples with wtNPM1 in a 9 hrs $^{51}$chromium release assay. Both CD8 and CD4 cells transduced with the TCR for ΔNPM1 showed specific lysis of AML with ΔNPM1, but not of AML with wtNPM1 (FIG. 7). In conclusion, the results show that CLAVEEVSL (SEQ ID NO:1) is a therapeutic neoantigen expressed on primary AML with ΔNPM1 that can be efficiently targeted by TCR gene transfer in a co-receptor independent fashion.

DISCUSSION

The inventors have identified an HLA-A*02:01-restricted 9-mer peptide encoded by ΔNPM1 (CLAVEEVSL (SEQ ID NO:1)) in the HLA class I ligandome of primary AML. T cell clones with a TCR specific for this peptide were isolated from healthy individuals and the TCR from one of the clones was shown to mediate specific recognition and lysis of primary AML with ΔNPM1 upon retroviral introduction in CD8 and CD4 cells, indicating that CLAVEEVSL (SEQ ID NO:1) is a therapeutic neoantigen on AML that can be targeted by TCR gene transfer in a co-receptor independent fashion.

Using HLA class I ligandome data of 12 primary AML, the inventors identified C*LAVEEVSL (cysteinylated form of SEQ ID NO:1) as a peptide that is endogenously processed and presented on AML with ΔNPM1. Although no match was found between the eluted and synthetic peptide in the absence of cysteinylation, the data provide strong evidence that also the uncysteinylated CLAVEEVSL (SEQ ID NO:1) peptide is presented on AML. Clone 1A2, which was selected for TCR cloning and gene transfer, was shown to recognize both synthetic C*LAVEEVSL (cysteinylated form of SEQ ID NO:1) and CLAVEEVSL (SEQ ID NO:1) peptides. The clone could also be stained with both pMHC tetramers, although binding to the tetramer with the cysteinylated peptide was weaker. Experiments in which synthetic peptides with serine substitutions were tested confirmed that the first residue of the epitope is not essential for reactivity of clone 1A2. For clone 4A8, however, results were different. Clone 4A8 recognized CLAVEEVSL (SEQ ID NO:1), but not C*LAVEEVSL (cysteinylated form of SEQ ID NO:1), and only the pMHC tetramer with the uncysteinylated peptide could bind to the T cell clone. The importance of the first residue of the peptide for T cell recognition was confirmed by lack of reactivity of clone 4A8 against a synthetic peptide in which the first residue was substituted by a serine. Strikingly, despite its failure to recognize the cysteinylated peptide, clone 4A8 showed reactivity against 2 of 3 AML with ΔNPM1. Based on the reactivity patterns of clone 1A2 and 4A8, the inventors suggest that cysteinylated as well as uncysteinylated ΔNPM1 peptide variants are presented on the cell surface, but that expression levels of the epitopes may vary between AML. The reason for the absence of CLAVEEVSL (SEQ ID NO:1) in the HLA class I ligandome is unknown, but may be explained by low surface expression or poor quality of the mass spectrum of the eluted peptide.

Interestingly, patients carrying ΔNPM1 in the absence of concomitant internal tandem duplications in the fms-related tyrosine kinase 3 gene (FLT3-ITD) show improved survival after chemotherapy, thereby often abolishing the need for allogeneic stem cell transplantation.[1,2,5,13] An in vivo immune response against peptides derived from ΔNPM1 may underlie this favorable prognosis, especially since the ΔNPM1 protein is dislocated from the nucleolus to the cytoplasm where it is susceptible to proteasomal degradation and subsequent processing by the HLA class I antigen presentation pathway.[6] Greiner et al.[14] searched in vitro for T cell responses against 9 HLA-A*02:01-restricted peptides derived from ΔNPM1, including CLAVEEVSL (SEQ ID NO:1), in healthy volunteers and patients with AML. After co-culture of CD8 cells with peptide-loaded PBMC, T cell responses against 2 of 9 peptides were demonstrated in both healthy volunteers and patients, but no immune response was measured against CLAVEEVSL (SEQ ID NO:1). They subsequently screened 25 patients with ΔNPM1 AML and revealed that overall survival for patients with immune responses against these 2 ΔNPM1-derived peptides was significantly higher than for patients without immune responses.[15] However, the number of patients screened in this study was low and FLT3 mutational status was not determined. Recent data shows that patients with FLT3-ITD, especially patients with a high allelic ratio of expression of the mutated versus wild type FLT3 gene, have a worse prognosis as compared to patients without FLT3-ITD, irrespective of NPM1 mutational status.[13] This observation may argue against in vivo induction of immune responses against ΔNPM1 underlying the favorable prognosis, but underline the importance of intrinsic factors for AML tumor growth and the relevance of ΔNPM1 TCR gene therapy to treat AML with unfavorable prognosis.

AML arises from a single founding clone harboring hundreds of somatic mutations with only a few driver mutations. Subclones can emerge from the founding clone through accumulation of additional mutations that confer survival advantage to the cell. As a result, the majority of mutations in subclones are shared with the founding clone and a minority is clone-specific. This heterogeneous composition of AML increases the chance for clonal evolution in persistent or relapsed disease after induction or consolidation therapy. Targeting neoantigens arising from shared mutations is an attractive immunotherapeutic strategy to eradicate the founding clone as well as subclones. Neoantigens arising from passenger mutations can be easily lost as a result of immune editing of the tumor by T cells, resulting in tumor immune evasion. Immune escape is less likely to occur when neoantigens produced by driver mutations are targeted, since these are essential for malignant transformation and present in all tumor cells.[16] Thus far, only a few neoantigens arising from driver mutations have been identified of which mutant KRAS leads to an antigen that is expressed in 45% of pancreatic cancers and 13% of colorectal cancers.[17] Although immune evasion for neoantigens arising from driver mutations is less likely, Tran et al. demonstrated escape from TCR gene therapy for mutant KRAS in a patient with metastatic colorectal cancer via loss of HLA-C*08:02. Still, ΔNPM1 as clonal driver mutation occurring early in leukemogenesis remains an attractive target for immunotherapy. ΔNPM1 is also an ideal target based on its high mutation frequency in 30% of primary AML.[6] The characteristic 4 bp frameshift insertion occurs at a restricted number of positions in the coding sequence (859, 860 and 861) and although the exact 4-bp sequence can differ, the majority of mutations encode the same 11 amino acids alternative reading frame (CLAVEEVSLRK (SEQ ID NO: 27)). The inventors have identified a TCR targeting the first 9 residues of this alternative reading frame in HLA-A*02:01. This TCR can be used for future gene therapy to treat patients with AML with ΔNPM1. Clinical studies will show efficacy and potential toxicity of ΔNPM1 TCR gene therapy and whether immune evasion by loss of HLA-A*02:01 is of any significance in hampering long-term remission of AML.

The TCR isolated from clone 1A2 was shown to mediate specific recognition and lysis of HLA-A*02:01 positive AML cells with ΔNPM1 upon transfer to CD8 as well as CD4 cells, demonstrating that the TCR is able to redirect immune reactivity to AML in a co-receptor independent manner. The key role of CD4 cells in anti-tumor immunity has become more apparent over the last few decades. Traditionally, CD4 cells are known to provide help to CD8 cells, resulting in improved tumor clearance and induction of immunological memory. However, growing evidence suggests that CD4 cells can also mediate tumor rejection in the absence of CD8 cells. Patients with hematological malignancies who received CD8-depleted allogeneic bone marrow grafts or donor lymphocyte infusions developed similar graft-versus-leukemia responses as patients receiving unmodified stem cell grafts or donor lymphocytes, whereas the incidence and severity of graft-versus-host disease was reduced. In the autologous setting, adoptive transfer of CD4 cells directed against HLA class II-restricted tumor-associated antigens or neoantigens resulted in tumor regression in patients with metastatic melanoma and cholangiocarcinoma, respectively.[18] However, since tumors often do not express HLA class II, administration of a mix of CD8 and CD4 cells expressing antigen-receptors that are independent of HLA class II may be preferable and result in superior anti-tumor immunity. Indeed, Turtle et al.[19,20] demonstrated that administration of a defined ratio of CD8 and CD4 cells expressing the same CD19-specific chimeric antigen receptor resulted in complete remission in a substantial number of patients with relapsed or refractory B cell non-Hodgkin's lymphoma and B cell acute lymphoblastic leukemia. Likewise, as previously demonstrated in mice, adoptive transfer of CD8 and CD4 cells expressing identical TCRs directed at HLA class I-restricted epitopes, like CLAVEEVSL (SEQ ID NO:1), may lead to potent anti-tumor immunity.

Recently, ΔNPM1 has been described as reliable marker for measuring minimal residual disease in patients with AML.[21] Persistence of ΔNPM1 transcripts as detected by quantitative RT-PCR in peripheral blood of patients after chemotherapy was associated with disease relapse within 3 years of follow-up. The prognostic value of ΔNPM1 was shown to be independent of other risk factors such as presence of FLT3-ITD or mutated DNA methyltransferase 3 alpha (DNMT3A).[1,2,5,13] Importantly, the authors reported that presence of ΔNPM1 transcripts after the second chemotherapy cycle in patients with a favorable molecular signature at diagnosis (no FLT3-ITD or mutated DNMT3A) marked a group of patients with relatively poor outcome, whereas absence of ΔNPM1 transcripts after the second chemotherapy cycle in patients with unfavorable molecular profiles (FLT3-ITD, mutated DNMT3A or both) distinguished patients with relatively good prognosis.[21] Therefore, ΔNPM1 as marker for disease status can be used to select patients eligible for alloSCT and allows optimal timing and selection of patients for ΔNPM1 TCR gene therapy to treat persistent or relapsed disease after chemotherapy. Eventually, when clinical studies show that AML can be effectively treated by ΔNPM1 TCR gene transfer with low treatment-related mortality, it may replace alloSCT as standard therapy for patients with ΔNPM1 AML with poor prognosis based on adverse molecular abnormalities at diagnosis or detectable persistent or relapsed disease after chemotherapy, thereby improving overall survival of patients with AML.

REFERENCES

1. Döhner H, Weisdorf D J, Bloomfield C D. Acute Myeloid Leukemia. N Engl J Med. 2015 Sep. 17; 373(12):1136-52.
2. Döhner H, Estey E H, Amadori S, Appelbaum F R, Büchner T, Burnett A K et al; European LeukemiaNet. Diagnosis and management of acute myeloid leukemia in adults: recommendations from an international expert panel, on behalf of the European LeukemiaNet. Blood. 2010 Jan. 21; 115(3):453-74.
3. Schumacher T N, Schreiber R D. Neoantigens in cancer immunotherapy. Science. 2015 Apr. 3; 348(6230):69-74.
4. Tran E, Robbins P F, Rosenberg S A. 'Final common pathway' of human cancer immunotherapy: targeting random somatic mutations. Nat Immunol. 2017 Feb. 15; 18(3):255-262.
5. Papaemmanuil E, Gerstung M, Bullinger L, Gaidzik V I, Paschka P, Roberts N D et al. Genomic Classification and Prognosis in Acute Myeloid Leukemia. N Engl J Med. 2016 Jun. 9; 374(23):2209-21.
6. Falini B, Mecucci C, Tiacci E, Alcalay M, Rosati R, Pasqualucci L et al. Cytoplasmic nucleophosmin in acute myelogenous leukemia with a normal karyotype. N Engl J Med. 2005 Jan. 20; 352(3):254-66.
7. Burrows S R, Kienzle N, Winterhalter A, Bharadwaj M, Altman J D, Brooks A. Peptide-MHC class I tetrameric complexes display exquisite ligand specificity. J Immunol. 2000 Dec. 1; 165(11):6229-34.
8. Rodenko B, Toebes M, Hadrup S R, van Esch W J, Molenaar A M, Schumacher T N, Ovaa H. Generation of peptide-MHC class I complexes through U V-mediated ligand exchange. Nat Protoc. 2006; 1(3):1120-32.
9. Jahn L, Hombrink P, Hagedoorn R S, Kester M G, van der Steen D M, Rodriguez T et al. TCR-based therapy for multiple myeloma and other B-cell malignancies targeting intracellular transcription factor BOB1. Blood. 2017 Jan. 4.
10. Lefranc M P, Giudicelli V, Ginestoux C, Bodmer J, Müller W, Bontrop R et al. IMGT, the international ImMunoGeneTics database. Nucleic Acids Res. 1999 Jan. 1; 27(1):209-12.
11. Linnemann C, Heemskerk B, Kvistborg P, Kluin R J, Bolotin D A, Chen X et al. High-throughput identification of antigen-specific TCRs by TCR gene capture. Nat Med. 2013 November; 19(11):1534-41.
12. Heemskerk M H, Hoogeboom M, de Paus R A, Kester M G, van der Hoorn M A, Goulmy E et al. Redirection of antileukemic reactivity of peripheral T lymphocytes using gene transfer of minor histocompatibility antigen HA-2-specific T-cell receptor complexes expressing a conserved alpha joining region. Blood. 2003 Nov. 15; 102(10):3530-40.
13. Versluis J, In't Hout F E, Devillier R, van Putten W L, Manz M G, Vekemans M C et al. Comparative value of post-remission treatment in cytogenetically normal AML subclassified by NPM1 and FLT3-ITD allelic ratio. Leukemia. 2017 January; 31(1):26-33.
14. Greiner J, Ono Y, Hofmann S, Schmitt A, Mehring E, Gotz M et al. Mutated regions of nucleophosmin 1 elicit both CD4(+) and CD8(+) T-cell responses in patients with acute myeloid leukemia. Blood. 2012 Aug. 9; 120(6): 1282-9.
15. Greiner J, Schneider V, Schmitt M, Gotz M, Döhner K, Wiesneth M et al. Immune responses against the mutated region of cytoplasmatic NPM1 might contribute to the favorable clinical outcome of AML patients with NPM1 mutations (NPM1$^{mut}$). Blood. 2013 Aug. 8; 122(6):1087-8.
16. Blankenstein T, Leisegang M, Uckert W, Schreiber H. Targeting cancer-specific mutations by T cell receptor gene therapy. Curr Opin Immunol. 2015 April; 33:112-9.
17. Tran E, Robbins P F, Lu Y C, Prickett T D, Gartner J J, Jia L et al. T-Cell Transfer Therapy Targeting Mutant KRAS in Cancer. N Engl J Med. 2016 Dec. 8; 375(23): 2255-2262.
18. Tran E, Turcotte S, Gros A, Robbins P F, Lu Y C, Dudley M E et al. Cancer immunotherapy based on mutation-specific CD4$^+$ T cells in a patient with epithelial cancer. Science. 2014 May 9; 344(6184):641-5.
19. Turtle C J, Hanafi L A, Berger C, Hudecek M, Pender B, Robinson E et al. Immunotherapy of non-Hodgkin's lymphoma with a defined ratio of CD8+ and CD4+CD19-specific chimeric antigen receptor-modified T cells. Sci Transl Med. 2016 Sep. 7; 8(355):355ra116.
20. Turtle C J, Hanafi L A, Berger C, Gooley T A, Cherian S, Hudecek M et al. CD19 CAR-T cells of defined CD4+:CD8+ composition in adult B cell ALL patients. J Clin Invest. 2016 Jun. 1; 126(6):2123-38.

21. Ivey A, Hills R K, Simpson M A, Jovanovic J V, Gilkes A, Grech A et al; U K National Cancer Research Institute AML Working Group. Assessment of Minimal Residual Disease in Standard-Risk AML. N Engl J Med. 2016 Feb. 4; 374(5):422-33.

22. H. D. Meiring, E. van der Heeft, G. J. ten Hove, A. P. J. M. de Jong, Nanoscale LC MS(n): technical design and applications to peptide and protein analysis. J Sep Sci 25, 557-568 (2002).

23. Michal Bassani-Sternberg and George Coukos: Mass spectrometry-based antigen discovery for cancer immunotherapy. Current opinion in Immunology (2016) 41:9-17.

The invention claimed is:

1. An isolated nucleic acid sequence comprising a promoter operably linked to a nucleic acid sequence encoding:
   (a) a polypeptide comprising a CDR3 of a TCR α chain polypeptide that specifically binds to the peptide CLAVEEVSL (SEQ ID NO:1) and/or
   (b) a polypeptide comprising a CDR3 of a TCR β chain polypeptide that specifically binds to the peptide CLAVEEVSL (SEQ ID NO:1),
   wherein the isolated nucleic acid sequence is cDNA.

2. The isolated nucleic acid sequence of claim 1, wherein the nucleic acid sequence encodes both (a) and (b), and wherein (a) and (b) together specifically bind to the peptide CLAVEEVSL (SEQ ID NO:1).

3. The isolated nucleic acid sequence of claim 1, wherein:
   (i) the CDR3 of (a) has an amino acid sequence having at least 90% sequence identity to CAVTGARLMF (SEQ ID NO:2);
   (ii) the CDR3 of (a) is encoded by the nucleic acid sequence of SEQ ID NO: 3 or SEQ ID NO:4;
   (iii) the CDR3 of (b) has an amino acid sequence having at least 90% sequence identity to CASSPGGLSNEQF (SEQ ID NO:5);
   (iv) the CDR3 of (b) is encoded by the nucleic acid sequence of SEQ ID NO: 6 or SEQ ID NO:7;
   (v) the CDR3 of (a) is within a TCR α chain variable region that specifically binds to SEQ ID NO:1, optionally wherein (a) further comprises a TCR α chain constant region; optionally wherein the TCR α chain variable region has an amino acid sequence having at least 90% sequence identity to SEQ ID NO:8, and optionally wherein the TCR α chain variable region of (a) is encoded by the nucleic acid sequence of SEQ ID NO: 9 or SEQ ID NO:10;
   (vi) the CDR3 of (b) is within a TCR β chain variable region that specifically binds to SEQ ID NO:1, optionally wherein (b) further comprises a TCR β chain constant region, optionally wherein the TCR β chain variable region has an amino acid sequence having at least 90% sequence identity to SEQ ID NO:11, and optionally wherein the TCR β chain variable region of (b) is encoded by the nucleic acid sequence of SEQ ID NO: 12 or SEQ ID NO:13;
   (vii) the CDR3 of (a) is within a TCR α chain variable region having at least 90% sequence identity to SEQ ID NO:8, wherein the CDR3 has an amino acid sequence of SEQ ID NO: 2; and optionally wherein (a) comprises a TCR α chain constant region, and optionally wherein the TCR α chain variable region CDR1 has an amino acid sequence of SEQ ID NO:14 and the TCR α chain variable region CDR2 has an amino acid sequence of SEQ ID NO:15; and/or
   (viii) the CDR3 of (b) is within a TCR β chain variable region having at least 90% sequence identity to SEQ ID NO:11, wherein the CDR3 has an amino acid sequence of SEQ ID NO: 5; and optionally wherein (b) comprises a TCR β chain constant region, and optionally wherein the TCR β chain variable region CDR1 has an amino acid sequence of SEQ ID NO:16 and the TCR β chain variable region CDR2 has an amino acid sequence of SEQ ID NO:17.

4. The isolated nucleic acid sequence of claim 1, wherein the peptide CLAVEEVSL (SEQ ID NO:1) is cysteinylated.

5. The isolated nucleic acid sequence of claim 1, wherein the nucleic acid sequence encodes a T cell receptor.

6. A vector comprising the nucleic acid sequence of claim 1.

7. The vector of claim 6, wherein the vector is a plasmid or a viral vector, optionally wherein the vector is selected from the group consisting of a retrovirus, lentivirus, adeno-associated virus, adenovirus, vaccinia virus, canary poxvirus, herpes virus, minicircle vector, synthetic DNA, and synthetic RNA.

8. A modified cell transfected or transduced with the nucleic acid sequence of claim 1 or a vector comprising the nucleic acid sequence of claim 1.

9. The modified cell of claim 8, wherein the modified cell is selected from the group consisting of a CD8 T cell, a CD4 T cell, a NK cell, a NKT cell, a gamma-delta T cell, a hematopoietic stem cell, a progenitor cell, a T cell line and a NK-92 cell line, and optionally wherein the modified cell is a human cell.

10. A pharmaceutical composition for treating or preventing a ΔNPM1 positive haematological malignancy, comprising (a) the nucleic acid sequence of claim 1, a vector comprising the nucleic acid sequence of claim 1, or a modified cell comprising the nucleic acid sequence of claim 1, and (b) a pharmaceutically acceptable excipient, adjuvant, diluent and/or carrier.

11. A method of treating or preventing a ΔNPM1 positive haematological malignancy in a human subject, the method comprising administering to the subject a therapeutically effective amount of the pharmaceutical composition of claim 10.

12. The method of claim 11, wherein the haematological malignancy is a myeloid malignancy, and optionally wherein the myeloid malignancy is acute myeloid leukemia.

13. The method of claim 11, wherein the method induces or enhances a cell mediated immune response in the subject.

14. A method of generating a T cell receptor, comprising contacting a nucleic acid sequence of claim 1 with a cell under conditions in which the nucleic acid sequence is incorporated and expressed by the cell to generate the T cell receptor that specifically binds to the peptide of SEQ ID NO:1.

15. The method of claim 14, wherein the method is ex vivo.

\* \* \* \* \*

SEQUENCE LISTING

```
<160> NUMBER OF SEQ ID NOS: 34

<210> SEQ ID NO 1
<211> LENGTH: 9
<212> TYPE: PRT
<213> ORGANISM: Homo sapiens

<400> SEQUENCE: 1

Cys Leu Ala Val Glu Glu Val Ser Leu
1               5

<210> SEQ ID NO 2
<211> LENGTH: 10
<212> TYPE: PRT
<213> ORGANISM: Homo sapiens

<400> SEQUENCE: 2

Cys Ala Val Thr Gly Ala Arg Leu Met Phe
1               5                   10

<210> SEQ ID NO 3
<211> LENGTH: 30
<212> TYPE: DNA
<213> ORGANISM: Homo sapiens

<400> SEQUENCE: 3
tgtgccgtta cggggggccag actcatgttt                                          30

<210> SEQ ID NO 4
<211> LENGTH: 30
<212> TYPE: DNA
<213> ORGANISM: Artificial Sequence
<220> FEATURE:
<223> OTHER INFORMATION: optimised nucleic acid sequence encoding CDR3
      (TCR alpha chain)

<400> SEQUENCE: 4
tgcgcagtga caggagcaag gctgatgttc                                           30

<210> SEQ ID NO 5
<211> LENGTH: 13
<212> TYPE: PRT
<213> ORGANISM: Homo sapiens

<400> SEQUENCE: 5

Cys Ala Ser Ser Pro Gly Gly Leu Ser Asn Glu Gln Phe
1               5                   10

<210> SEQ ID NO 6
<211> LENGTH: 39
<212> TYPE: DNA
<213> ORGANISM: Homo sapiens

<400> SEQUENCE: 6
```
tgcgccagca gccctggcgg cttgtccaat gagcagttc                      39

<210> SEQ ID NO 7
<211> LENGTH: 39
<212> TYPE: DNA
<213> ORGANISM: Artificial Sequence
<220> FEATURE:
<223> OTHER INFORMATION: optimised nucleic acid sequence encoding CDR3
      (TCR beta chain)

<400> SEQUENCE: 7
tgcgcaagct ccccaggagg cctgtccaac gagcagttc                      39

<210> SEQ ID NO 8
<211> LENGTH: 129
<212> TYPE: PRT
<213> ORGANISM: Homo sapiens

<400> SEQUENCE: 8

Met Lys Ser Leu Arg Val Leu Leu Val Ile Leu Trp Leu Gln Leu Ser
1               5                   10                  15

Trp Val Trp Ser Gln Gln Lys Glu Val Glu Gln Asn Ser Gly Pro Leu
            20                  25                  30

Ser Val Pro Glu Gly Ala Ile Ala Ser Leu Asn Cys Thr Tyr Ser Asp
        35                  40                  45

Arg Gly Ser Gln Ser Phe Phe Trp Tyr Arg Gln Tyr Ser Gly Lys Ser
    50                  55                  60

Pro Glu Leu Ile Met Phe Ile Tyr Ser Asn Gly Asp Lys Glu Asp Gly
65                  70                  75                  80

Arg Phe Thr Ala Gln Leu Asn Lys Ala Ser Gln Tyr Val Ser Leu Leu
                85                  90                  95

Ile Arg Asp Ser Gln Pro Ser Asp Ser Ala Thr Tyr Leu Cys Ala Val
            100                 105                 110

Thr Gly Ala Arg Leu Met Phe Gly Asp Gly Thr Gln Leu Val Val Lys
        115                 120                 125

Pro

<210> SEQ ID NO 9
<211> LENGTH: 387
<212> TYPE: DNA
<213> ORGANISM: Homo sapiens

<400> SEQUENCE: 9
atgaaatcct tgagagtttt actagtgatc ctgtggcttc agttgagctg ggtttggagc      60
caacagaagg aggtggagca gaattctgga cccctcagtg ttccagaggg agccattgcc     120
tctctcaact gcacttacag tgaccgaggt tcccagtcct cttctggta cagacaatat     180 tctgggaaaa gccctgagtt gataatgttc atatactcca atggtgacaa agaagatgga     240
aggtttacag cacagctcaa taagccagc cagtatgttt ctctgctcat cagagactcc     300
cagcccagtg attcagccac ctacctctgt gccgttacgg gggccagact catgtttgga     360
gatggaactc agctggtggt gaagccc                                        387

<210> SEQ ID NO 10
<211> LENGTH: 387
<212> TYPE: DNA
<213> ORGANISM: Artificial Sequence
<220> FEATURE:
<223> OTHER INFORMATION: optimised nucleic acid sequence encoding ?

chain variable region

<400> SEQUENCE: 10

| atgaaatcct | tgagagtttt | actagtgatc | ctgtggcttc | aattgagctg | ggtgtggtcc | 60 |
| cagcagaagg | aggtggagca | gaactctgga | ccactgagcg | tgccagaggg | agccatcgcc | 120 |
| agcctgaatt | gcacctactc | cgaccggggc | agccagtcct | tcttttggta | cagacagtat | 180 |
| tccggcaagt | ctcccgagct | gatcatgttc | atctattcta | acggcgacaa | ggaggatggc | 240 |
| aggtttacag | cccagctgaa | taaggcctcc | cagtacgtgt | ctctgctgat | ccgcgactcc | 300 |
| cagccttctg | atagcgccac | ctacctgtgc | gcagtgacag | agcaaggct | gatgttcggc | 360 |
| gacggaaccc | agctggtggt | gaagcca | | | | 387 |

<210> SEQ ID NO 11
<211> LENGTH: 132
<212> TYPE: PRT
<213> ORGANISM: Homo sapiens

<400> SEQUENCE: 11

Met Gly Ser Arg Leu Leu Cys Trp Val Leu Cys Leu Leu Gly Ala
1               5                   10                  15

Gly Pro Val Lys Ala Gly Val Thr Gln Thr Pro Arg Tyr Leu Ile Lys
            20                  25                  30

Thr Arg Gly Gln Gln Val Thr Leu Ser Cys Ser Pro Ile Ser Gly His
        35                  40                  45

Arg Ser Val Ser Trp Tyr Gln Gln Thr Pro Gly Gln Gly Leu Gln Phe
    50                  55                  60

Leu Phe Glu Tyr Phe Ser Glu Thr Gln Arg Asn Lys Gly Asn Phe Pro
65                  70                  75                  80

Gly Arg Phe Ser Gly Arg Gln Phe Ser Asn Ser Arg Ser Glu Met Asn
                85                  90                  95

Val Ser Thr Leu Glu Leu Gly Asp Ser Ala Leu Tyr Leu Cys Ala Ser
            100                 105                 110

Ser Pro Gly Gly Leu Ser Asn Glu Gln Phe Phe Gly Pro Gly Thr Arg
        115                 120                 125

Leu Thr Val Leu
    130

<210> SEQ ID NO 12
<211> LENGTH: 396
<212> TYPE: DNA
<213> ORGANISM: Homo sapiens

<400> SEQUENCE: 12

| atgggctcca | ggctgctctg | ttgggtgctg | ctttgtctcc | tgggagcagg | cccagtaaag | 60 |
| gctggagtca | ctcaaactcc | aagatatctg | atcaaaacga | gaggacagca | agtgacactg | 120 |
| agctgctccc | ctatctctgg | cataggagt | gtatcctggt | accaacagac | cccaggacag | 180 |
| ggccttcagt | tcctctttga | atacttcagt | gagacacaga | gaaacaaagg | aaacttccct | 240 |
| ggtcgattct | cagggcgcca | gttctctaac | tctcgctctg | agatgaatgt | gagcaccttg | 300 |
| gagctggggg | actcggccct | ttatctttgc | gccagcagcc | ctggcggctt | gtccaatgag | 360 |
| cagttcttcg | ggccagggac | acggctcacc | gtgcta | | | 396 |

<210> SEQ ID NO 13
<211> LENGTH: 396
<212> TYPE: DNA

<213> ORGANISM: Artificial Sequence
<220> FEATURE:
<223> OTHER INFORMATION: optimised nucleic acid sequence encoding beta
      chain variable region

<400> SEQUENCE: 13

```
atgggctcca ggctgctgtg ctgggtgctg ctgtgcctgc tgggagcagg accagtgaag      60
gcaggcgtga cccagacacc taggtacctg atcaagaccc gcggccagca ggtgacactg     120
tcttgcagcc ctatctctgg ccaccgctcc gtgtcttggt accagcagac ccaggacag     180 ggcctgcagt tcctgtttga gtatttctct gagacacagc ggaacaaggg caatttcccc     240
ggccggttta gcggcagaca gtttagcaac tccagatctg agatgaatgt gagcaccctg     300
gagctgggcg actccgccct gtacctgtgc gcaagctccc caggaggcct gtccaacgag     360
cagttctttg gaccaggaac caggctgaca gtgctg                                396
```

<210> SEQ ID NO 14
<211> LENGTH: 7
<212> TYPE: PRT
<213> ORGANISM: Homo sapiens

<400> SEQUENCE: 14

```
Ser Asp Arg Gly Ser Gln Ser
1               5
```

<210> SEQ ID NO 15
<211> LENGTH: 7
<212> TYPE: PRT
<213> ORGANISM: Homo sapiens

<400> SEQUENCE: 15

```
Phe Ile Tyr Ser Asn Gly Asp
1               5
```

<210> SEQ ID NO 16
<211> LENGTH: 5
<212> TYPE: PRT
<213> ORGANISM: Homo sapiens

<400> SEQUENCE: 16

```
Ser Gly His Arg Ser
1               5
```

<210> SEQ ID NO 17
<211> LENGTH: 13
<212> TYPE: PRT
<213> ORGANISM: Homo sapiens

<400> SEQUENCE: 17

```
Glu Tyr Phe Ser Glu Thr Gln Arg Asn Lys Gly Asn Phe
1               5                   10
```

<210> SEQ ID NO 18
<211> LENGTH: 21
<212> TYPE: DNA
<213> ORGANISM: Homo sapiens

<400> SEQUENCE: 18

```
agtgaccgag gttcccagtc c                                                 21
```

<210> SEQ ID NO 19
<211> LENGTH: 21
<212> TYPE: DNA

```
<213> ORGANISM: Artificial Sequence
<220> FEATURE:
<223> OTHER INFORMATION: optimised nucleic acid sequence encoding CDR1
      (TCR alpha chain)

<400> SEQUENCE: 19
tccgaccggg gcagccagtc c                                                   21

<210> SEQ ID NO 20
<211> LENGTH: 21
<212> TYPE: DNA
<213> ORGANISM: Homo sapiens

<400> SEQUENCE: 20
ttcatatact ccaatggtga c                                                   21

<210> SEQ ID NO 21
<211> LENGTH: 21
<212> TYPE: DNA
<213> ORGANISM: Artificial Sequence
<220> FEATURE:
<223> OTHER INFORMATION: optimised nucleic acid sequence encoding CDR2
      (TCR alpha chain)

<400> SEQUENCE: 21
ttcatctatt ctaacggcga c                                                   21

<210> SEQ ID NO 22
<211> LENGTH: 15
<212> TYPE: DNA
<213> ORGANISM: Homo sapiens

<400> SEQUENCE: 22
tctgggcata ggagt                                                          15

<210> SEQ ID NO 23
<211> LENGTH: 15
<212> TYPE: DNA
<213> ORGANISM: Artificial Sequence
<220> FEATURE:
<223> OTHER INFORMATION: optimised nucleic acid sequence encoding CDR1
      (TCR beta chain)

<400> SEQUENCE: 23
tctggccacc gctcc                                                          15

<210> SEQ ID NO 24
<211> LENGTH: 39
<212> TYPE: DNA
<213> ORGANISM: Homo sapiens

<400> SEQUENCE: 24
gaatacttca gtgagacaca gagaaacaaa ggaaacttc                                39

<210> SEQ ID NO 25
<211> LENGTH: 39
<212> TYPE: DNA
<213> ORGANISM: Artificial Sequence
<220> FEATURE:
<223> OTHER INFORMATION: optimised nucleic acid sequence encoding CDR2
      (TCR beta chain)

<400> SEQUENCE: 25
gagtatttct ctgagacaca gcggaacaag ggcaatttc                                39
```

```
<210> SEQ ID NO 26
<211> LENGTH: 9
<212> TYPE: PRT
<213> ORGANISM: Homo sapiens

<400> SEQUENCE: 26

Ala Val Glu Glu Val Ser Leu Arg Lys
1               5

<210> SEQ ID NO 27
<211> LENGTH: 11
<212> TYPE: PRT
<213> ORGANISM: Homo sapiens

<400> SEQUENCE: 27

Cys Leu Ala Val Glu Glu Val Ser Leu Arg Lys
1               5                   10

<210> SEQ ID NO 28
<211> LENGTH: 8
<212> TYPE: PRT
<213> ORGANISM: Homo sapiens

<400> SEQUENCE: 28

Val Glu Glu Val Ser Leu Arg Lys
1               5

<210> SEQ ID NO 29
<211> LENGTH: 8
<212> TYPE: PRT
<213> ORGANISM: Homo sapiens

<400> SEQUENCE: 29

Ala Val Glu Glu Val Ser Leu Arg
1               5

<210> SEQ ID NO 30
<211> LENGTH: 21
<212> TYPE: PRT
<213> ORGANISM: Homo sapiens

<400> SEQUENCE: 30

Met Thr Asp Gln Glu Ala Ile Gln Asp Leu Cys Leu Ala Val Glu Glu
1               5                   10                  15

Val Ser Leu Arg Lys
            20

<210> SEQ ID NO 31
<211> LENGTH: 9
<212> TYPE: PRT
<213> ORGANISM: Cytomegalovirus

<400> SEQUENCE: 31

Asn Leu Val Pro Met Val Ala Thr Val
1               5

<210> SEQ ID NO 32
<211> LENGTH: 9
<212> TYPE: PRT
<213> ORGANISM: Homo sapiens

<400> SEQUENCE: 32

Ala Ile Gln Asp Leu Cys Leu Ala Val
1               5
```

```
<210> SEQ ID NO 33
<211> LENGTH: 9
<212> TYPE: PRT
<213> ORGANISM: Homo sapiens

<400> SEQUENCE: 33

Ala Ile Gln Asp Leu Cys Val Ala Val
1               5

<210> SEQ ID NO 34
<211> LENGTH: 21
<212> TYPE: PRT
<213> ORGANISM: Homo sapiens

<400> SEQUENCE: 34

Met Thr Asp Gln Glu Ala Ile Gln Asp Leu Cys Leu Ala Val Glu Glu
1               5                   10                  15

Val Ser Leu Arg Lys
            20
```